United States Patent
Agarwal et al.

(10) Patent No.: US 9,642,623 B2
(45) Date of Patent: May 9, 2017

(54) METHODS, DEVICES AND APPARATUS FOR PERFORMING A VASCULAR ANASTOMOSIS

(75) Inventors: Jayant P. Agarwal, Salt Lake City, UT (US); Bruce K. Gale, Taylorsville, UT (US); Lam Nguyen, Salt Lake City, UT (US); Cory Shorr, South Jordan, UT (US); Brian Stauffer, Clearfield, UT (US); Cody Lee Gehrke, South Jordan, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 1050 days.

(21) Appl. No.: 13/640,467

(22) PCT Filed: Apr. 15, 2011

(86) PCT No.: PCT/US2011/032723
§ 371 (c)(1),
(2), (4) Date: Apr. 24, 2013

(87) PCT Pub. No.: WO2011/130656
PCT Pub. Date: Oct. 20, 2011

(65) Prior Publication Data
US 2013/0204275 A1 Aug. 8, 2013

Related U.S. Application Data

(60) Provisional application No. 61/325,186, filed on Apr. 16, 2010, provisional application No. 61/332,493, (Continued)

(51) Int. Cl.
*A61B 17/11* (2006.01)
*A61B 17/00* (2006.01)

(52) U.S. Cl.
CPC ..... *A61B 17/11* (2013.01); *A61B 2017/00004* (2013.01); *A61B 2017/00349* (2013.01);
(Continued)

(58) Field of Classification Search
CPC ........ A61B 17/1128; A61B 2017/1103; A61B 2017/1107; A61B 2017/111;
(Continued)

(56) References Cited

U.S. PATENT DOCUMENTS 3,456,965 A 7/1969 Gajewski et al.
4,214,586 A 7/1980 Mericle
(Continued)

FOREIGN PATENT DOCUMENTS

CN 201445540 5/2010
EP 0568098 11/1993
(Continued)

OTHER PUBLICATIONS

Joji et al. "Experimental Study of Mechanical Microvascular Anastomosis with New Biodegradable Ring Device," British Journal of Plastic Surgery, 1999, 52: 559-564.
(Continued)

*Primary Examiner* — David C Eastwood
*Assistant Examiner* — Mikail Mannan
(74) *Attorney, Agent, or Firm* — Workman Nydegger

(57) ABSTRACT

Methods, devices, apparatus, assemblies, and kits for performing a vascular anastomosis are disclosed. A device for a vascular anastomosis includes tissue engaging portions that can move between at least two configurations. In some embodiments, the tissue engaging portions move without the aid of moving parts, while in other embodiments the tissue engaging portions extend from one or more movable wings. The tissue engaging portions may be separated by a first distance when in a pre-deployment configuration and by a second distance when in a deployed configuration. A method includes engaging a plurality of tissue engaging members of a coupling device against first end tissue. After selectively engaging the tissue engaging members and first end tissue,
(Continued)

the first end tissue is stretched by at least moving the tissue engaging members. The stretched first end tissue is coupled to the second end tissue by mating the coupling device to a mating anastomosis device.

27 Claims, 30 Drawing Sheets

Related U.S. Application Data filed on May 7, 2010, provisional application No. 61/467,204, filed on Mar. 24, 2011, provisional application No. 61/467,237, filed on Mar. 24, 2011.

(52) U.S. Cl.
CPC ............... *A61B 2017/00477* (2013.01); *A61B 2017/00867* (2013.01); *A61B 2017/00893* (2013.01); *A61B 2017/1103* (2013.01); *A61B 2017/1107* (2013.01); *A61B 2017/1121* (2013.01); *A61B 2017/1125* (2013.01); *A61B 2017/1132* (2013.01)

(58) Field of Classification Search
CPC ......... A61B 17/1114; A61B 2017/1117; A61B 2017/1121; A61B 2017/1125; A61B 2017/1132; A61B 2017/1135; A61B 2017/1139; A61F 2/064
USPC .................. 606/153, 154, 155, 156, 152
See application file for complete search history.

(56) References Cited

U.S. PATENT DOCUMENTS

| | | | |
|---|---|---|---|
| 4,294,255 A | | 10/1981 | Geroc |
| 4,366,819 A | | 1/1983 | Kaster |
| 4,523,592 A | * | 6/1985 | Daniel ................. A61B 17/11 606/153 |
| 5,695,504 A | | 12/1997 | Gifford, III et al. |
| 5,797,934 A | | 8/1998 | Rygaard |
| 5,951,576 A | | 9/1999 | Wakabayashi |
| 6,030,395 A | | 2/2000 | Nash et al. |
| 6,319,231 B1 | | 11/2001 | Andrulitis |
| 6,329,321 B2 | | 12/2001 | Okura et al. |
| 6,666,873 B1 | | 12/2003 | Cassell |
| 6,905,504 B1 | | 6/2005 | Vargas |
| 7,192,400 B2 | | 3/2007 | Campbell et al. |
| 2001/0039425 A1 | | 11/2001 | Dakov |
| 2004/0186489 A1 | * | 9/2004 | Lee .................... A61B 17/0643 606/153 |
| 2005/0070924 A1 | | 3/2005 | Schaller et al. |
| 2005/0149075 A1 | | 7/2005 | Borghi et al. |
| 2006/0085017 A1 | | 4/2006 | Borghi |
| 2007/0250082 A1 | | 10/2007 | Kansoul |
| 2010/0174300 A1 | | 7/2010 | Blondeel |
| 2011/0230902 A1 | | 9/2011 | Kansoul |
| 2012/0123453 A1 | | 5/2012 | Asfora et al. |
| 2012/0123454 A1 | * | 5/2012 | Asfora .................. A61B 17/08 606/153 |
| 2013/0204275 A1 | | 8/2013 | Agarwal et al. |

FOREIGN PATENT DOCUMENTS

| | | |
|---|---|---|
| JP | 2009118927 | 6/2009 |
| KR | 101235096 | 2/2013 |
| WO | 2004000135 | 12/2003 |
| WO | 2004000138 | 12/2003 |
| WO | 2008115922 | 9/2008 |
| WO | 2009028799 | 3/2009 |
| WO | 2011130656 | 10/2011 |

OTHER PUBLICATIONS

Synovis MicroCompanies Alliance, Inc. "GEM Microvascular Anastomotic Coupler Device and System," available at http://www.synovismicro.com/GEM_Flow_COUPLER_Device_and_System.php accessed May 5, 2015.
European Search Report for EP11769684 dated Mar. 20, 2015.
Written Opinion for PCT/US2011/032723 dated Dec. 26, 2011.
International Search Report and Written Opinion for PCT/US2014/71930 dated Apr. 16, 2015.
Global Patent Solutions Search Report for 6300.U-5664 dated Oct. 18, 2013.
Synovis Micro Companies Alliance, Inc. "Microvascular Anastomotic Coupler," http://www.synovismicro.com/gem_microvascular_anastomotic_couple_clinical_video.php, available as early as Oct. 14, 2013. Video.
Kingsungmedical, "Experience of the MCA Microvascular Anastomotic Coupler in Free Flap," http://kinsungmedical.com/en/upload/newfile/200904/1238638771xj0hdqzr.pdf, available as early as Oct. 14, 2013.
Pratt, et al. "Technology-Assisted and Sutureless Microvascular Anastomoses: Evidence for Current Techniques." *Microsurgery*, 2012, 32(1), pp. 68-76.
International Search Report for PCT/US2011/032723 dated Dec. 26, 2011.

\* cited by examiner

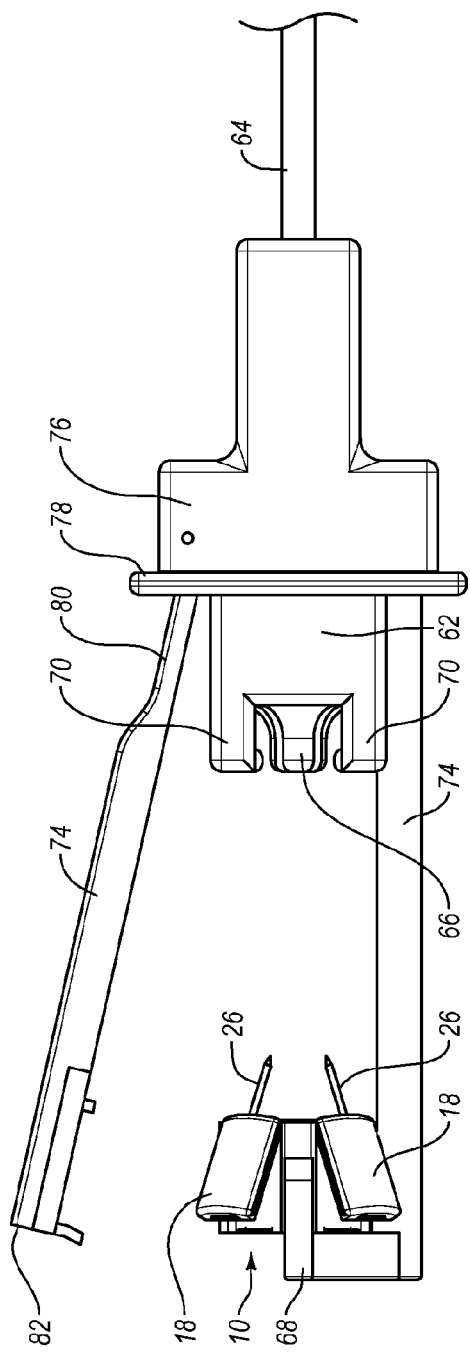
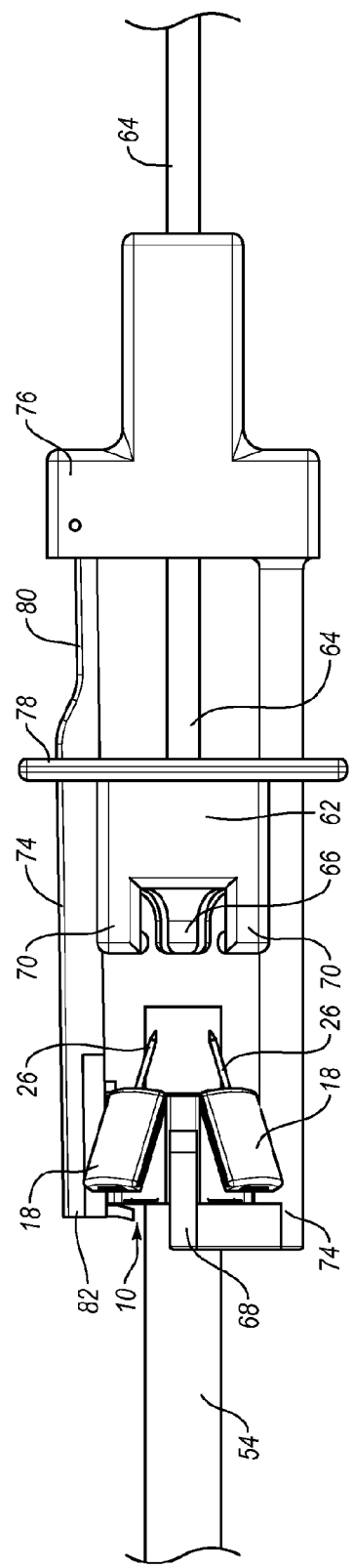
Fig. 8B
Fig. 8C

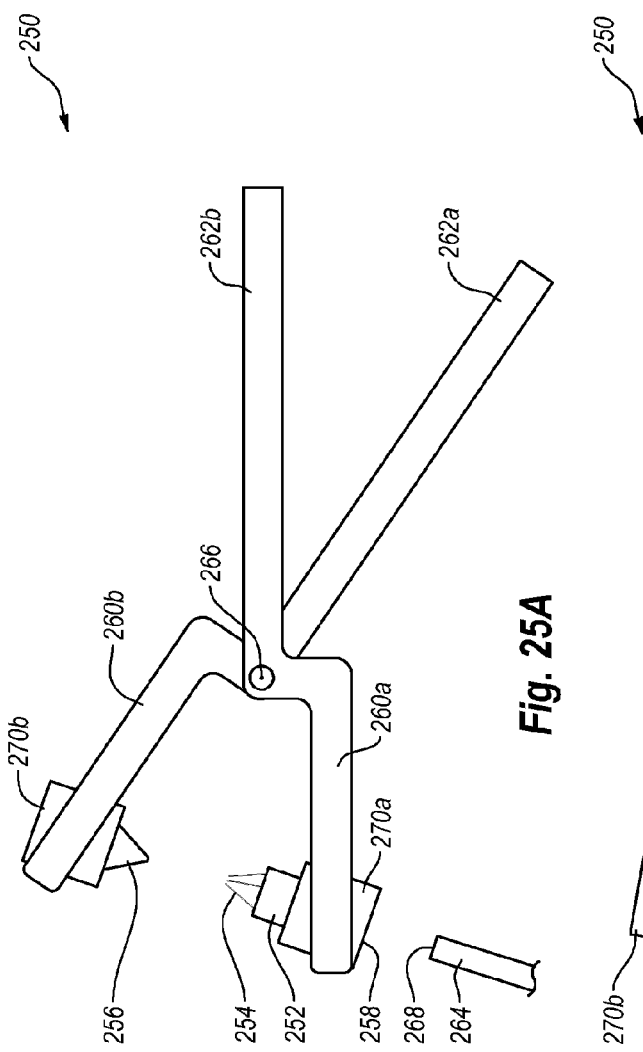
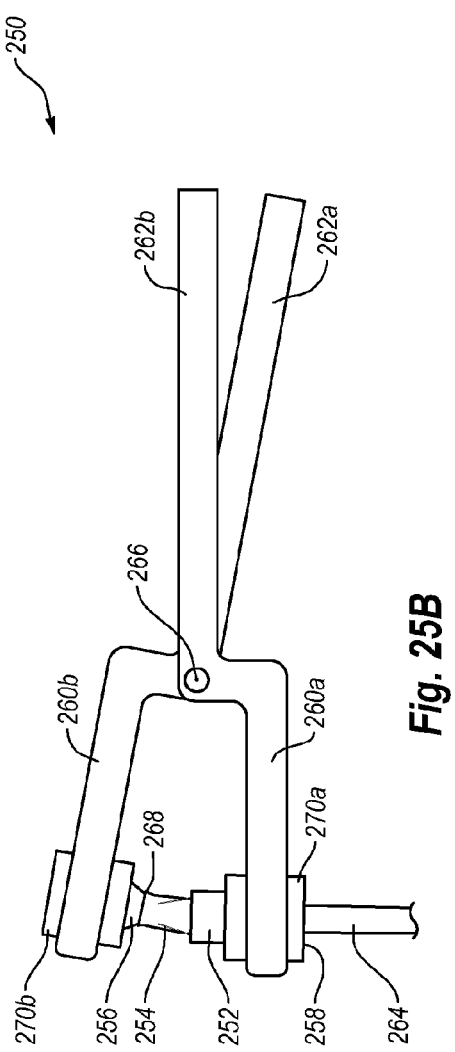
Fig. 25A
Fig. 25B

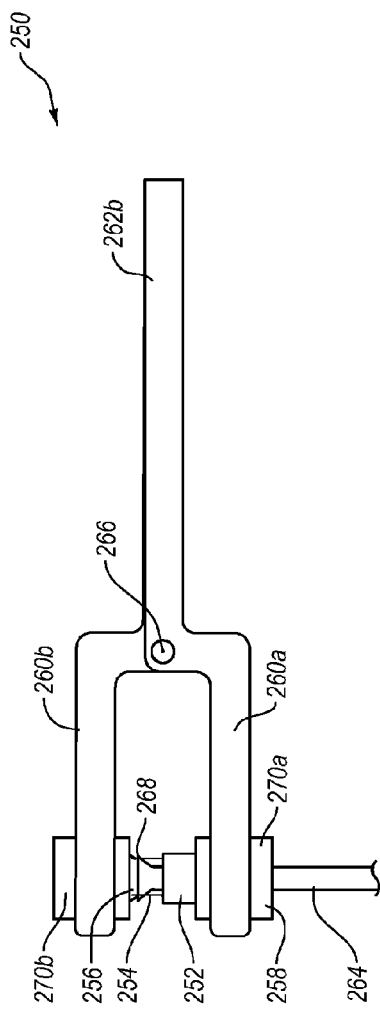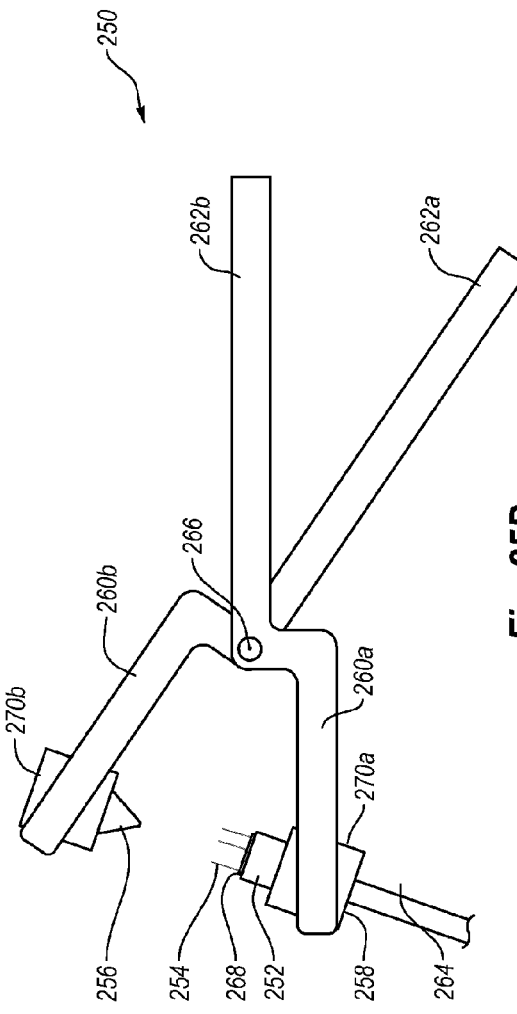

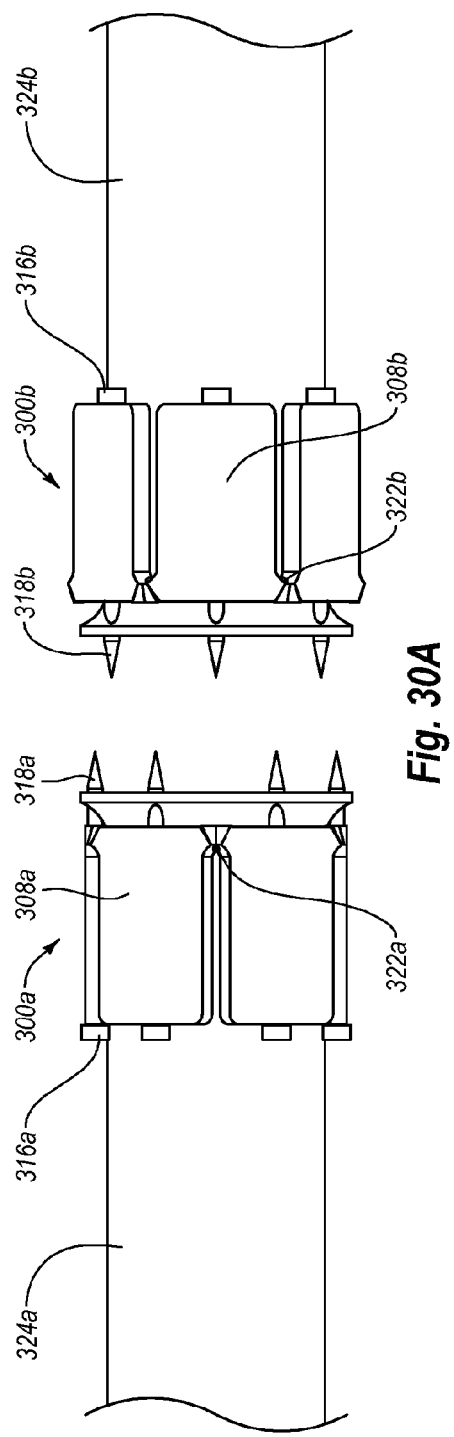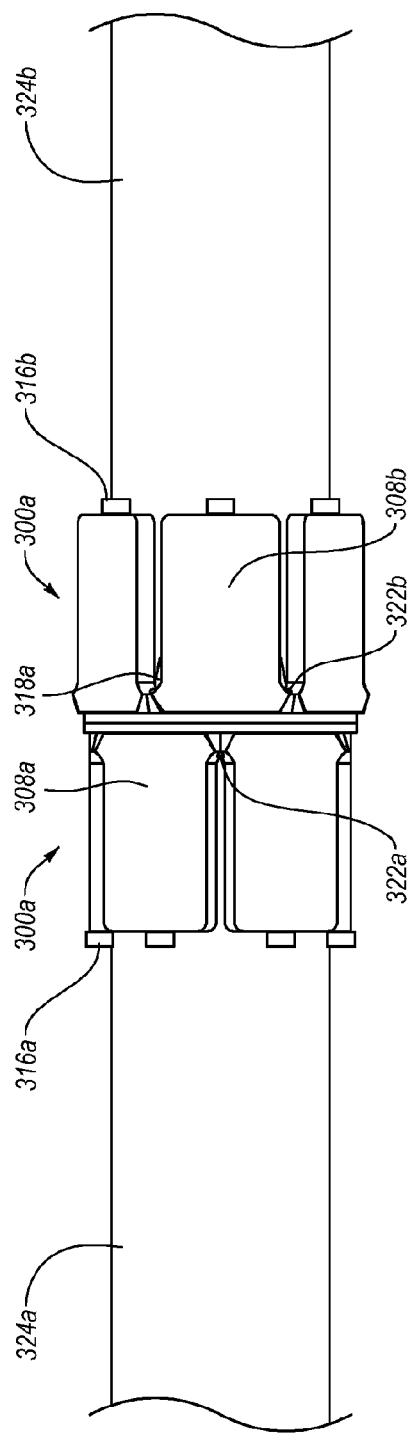

METHODS, DEVICES AND APPARATUS FOR PERFORMING A VASCULAR ANASTOMOSIS

This application claims priority to and the benefit of: PCT patent application no. PCT/US2011/032723, filed on Apr. 15, 2011, entitled METHODS, DEVICES, AND APPARATUS FOR PERFORMING A VASCULAR ANASTOMOSIS; which claims priority to and the benefit of the following: U.S. provisional patent application No. 61/325,186, filed on Apr. 16, 2010, entitled METHODS, DEVICES, AND APPARATUS FOR PERFORMING A VASCULAR ANASTOMOSIS; U.S. provisional patent application No. 61/332,493, filed on May 7, 2010, entitled METHODS, DEVICES, AND APPARATUS FOR PERFORMING A VASCULAR ANASTOMOSIS; U.S. provisional patent application No. 61/467,204, filed on Mar. 24, 2011, entitled METHODS, DEVICES, AND APPARATUS FOR PERFORMING A VASCULAR ANASTOMOSIS; and U.S. provisional patent application No. 61/467,237, filed on Mar. 24, 2011, entitled METHODS, DEVICES, AND APPARATUS FOR PERFORMING A VASCULAR ANASTOMOSIS, each of which is incorporated herein by reference in its entirety.

FIELD OF THE INVENTION

The present disclosure relates generally to medical devices, and more particularly to devices, apparatus, and methods for performing a vascular anastomosis, such as an end-to-end anastomosis.

BACKGROUND OF THE INVENTION

The French surgeon Alexis Carrell is considered by many to be the father of modern vascular surgery. Indeed, many of the same vascular techniques that are in use today were developed and performed by Dr. Carrell more than one hundred years ago. His particular area of expertise related to the performance of surgical grafts and the reconnecting of arteries and veins, and his contributions in this field led to his receipt of the Nobel Prize in 1912.

As some of his early work, Dr. Carrell was able to show that by suturing two cut ends of vasculature together, the integrity of the vessel could be re-established. Laminar flow within the vessel could then be re-established. These discoveries led to microvascular surgery within the United States increasing in popularity over the last half-century.

Harry J. Buncke was particularly influential in the emergence of microvascular surgery and his work—as well as the work of others who helped popularize microvascular surgery—was effectively an offshoot of the early work of Dr. Carrell. Dr. Buncke's work centered primarily on tissue transplantation and replantation of amputated parts, although microsurgery has now expanded into numerous medical specialties. Neurosurgery, ophthalmology, and cardiac surgery all now employ microvascular techniques that are largely derivatives of the early work by Dr. Carrell and Dr. Buncke.

The work of Dr. Carrell and Dr. Buncke, among others, led early microsurgeons to focus on the development of suture materials and techniques to allow the successful performance of an end-to-end anastomosis on vessels in the range of about one to four millimeters in outer diameter. As an outcome of these developments, current surgical techniques commonly involve suturing ends of vasculature together and making use of ultrafine nylon suture. Needles in the range of about fifty to one-hundred fifty microns in diameter are used to secure the ultrafine nylon suture in place. Because of the delicacy of the vasculature and the miniaturized size of the suture and needles, intraoperative magnification is also typically required for the successful completion of an end-to-end anastomosis.

Despite rapid changes in medical technology, current techniques for a micro-arterial, end-to-end anastomosis continue to this day to primarily involve the manual suturing of two cut ends of vasculature. Because of the small size of arteries being connected, a suturing process may be very expensive as even the most skilled surgeon may require a half hour or more to complete the anastomosis procedure, even with the help of expensive, complex microscopes.

Manual suturing of vasculature in an end-to-end anastomosis is not without risk. By suturing the vessel walls together, threads are generally exposed to the blood flow inside the vessel. The thread may react with the blood cells and cause or contribute to clotting. As clotting continues, the thread may contribute to possible thrombosis. Further, in some cases, a surgeon may thread sutures through both sides of the artery, thereby effectively sewing the artery shut in the process.

Various apparatuses have been suggested for connecting vasculature in anastomosis procedures, and possibly without the need to directly suture two vessels together. For example, U.S. Pat. No. 7,192,400 issued to Campbell et al., the publication "Experimental study of mechanical microvascular anastomosis with new biodegradable ring device" published by S. Joji et al. in the British Journal of Plastic Surgery, and the publication "GEM Microvascular Anastomatic Coupler Device and System" published by Synovis MicroCompanies Alliance, Inc. describe devices and techniques in which a vessel wall is stretched over various fixed pins on a coupling ring. Such devices and techniques are typically used for veins rather than arteries, due to the elasticity of the arteries. Other techniques that have been suggested include stapling techniques, extraluminal cuffing techniques, VCS clip application, and graft connectors.

Once two ends of a vessel are attached in an end-to-end anastomosis, it is generally desired that the vessel remain attached so that blood may begin to recirculate through the affected vasculature. Accordingly, devices, apparatus, and methods for performing an anastomosis and facilitating sealing would be considered useful.

BRIEF SUMMARY

Example embodiments within the present disclosure relate to devices, apparatus, and methods for performing a vascular anastomosis. Additional example embodiments of the present disclosure may relate to systems, kits, and methods of treatment in the field of anastomosis.

According to one exemplary embodiment, a vascular coupling device is disclosed. An exemplary vascular coupling device may include a body and a plurality of wing portions coupled to the body. The wing portions may be movable to adjust from a pre-deployment configuration towards a deployed configuration. A plurality of tissue engaging portions that extend from the wing portions may also be included. The tissue engaging portions may be separated by a first distance in a pre-deployment configuration and a second distance in a deployed configuration.

According to another example embodiment, a vascular coupling device includes a generally annular body having a proximal end and a distal end. The generally annular body may include at least three external surfaces extending generally between the proximal end and the distal end. At least three biasing mechanisms may be included, with each being disposed at one of the external surfaces. Wings may be coupled to the proximal end of the body. The wings may also have proximal and distal ends, as well as an interior surface corresponding to the external surfaces of the body. The wings can be pivotally connected to the body so as to rotate relative to the body and between a relaxed configuration and a deployed configuration in which the biasing mechanism is unstressed at the relaxed configuration and stressed at the deployed configuration.

Tissue engaging members may be attached to the proximal ends of the wings. The tissue engaging members may extend at an angle that is inclined relative to a longitudinal axis of the body when the wings are in the relaxed configuration, and be generally parallel to the longitudinal axis when the wings are in the deployed configuration. A locking mechanism may be connected to the body and wings such that the locking mechanism overcomes a biasing force exerted by the biasing mechanism, thereby maintaining the wings in the deployed configuration. Receiving portions may also be included and define openings that, in connection with the tissue engaging portions, are alternately spaced around the body.

A vascular anastomosis device is described for providing coupling of two portions of a vessel such that the vessel is held open during a vascular anastomosis procedure while further facilitating a tight seal between the two ends of the vessel and limiting a risk of thrombosis. Such an example device may be used in an end-to-end anastomosis procedure, side-to-end anastomosis procedure, another anastomosis procedure, or in another coupling procedure not involving anastomosis, although for simplicity all such procedures may be referred to as anastomosis procedures in this Summary. An example device may include a body that defines a longitudinal axis and includes at least four wing receptors. At least four wings may be generally disposed at the at least four wing receptors, and able to move with respect to the body between at least a pre-deployment configuration and a deployment configuration. The wings may be inclined with respect to the longitudinal axis.

At least four tissue engaging members may also be included and connected to a corresponding wing. The tissue engaging members may be configured to: (i) move relative to the longitudinal axis as the wings move from the pre-deployment configuration to the deployment configuration; and/or (ii) stretch a vessel engaged by the tissue engaging members when the wings are in the deployment configuration, such that an interior surface of the vessel is exposed. A sealing member may also be configured to connect to a portion of a mating device and facilitate sealing of the interior surface of the vessel with a corresponding portion of an opposing vessel or vessel portion. The sealing member may restrict disengagement between two mating end-to-end vascular anastomosis devices.

A method for performing an anastomosis is also described and includes engaging a plurality of tissue engaging members of a coupling device against a first end tissue. After engaging the one or more tissue engaging members against the first end tissue, the first end tissue is stretched by at least moving the one or more tissue engaging members. The stretched first end tissue is coupled to second end tissue, wherein coupling the stretched first end tissue to second end tissue includes attaching the coupling device to a mating anastomosis device.

Another method for performing an anastomosis is described and includes measuring a size of each of a first end of a vessel and a second end of a vessel. The first and second ends are matched with internal lumen diameters of corresponding first and second coupling devices. For each of the first and second devices and first and second ends, the coupling device is attached to the end by, at least, inserting a free end through an internal lumen of the coupling device. The free end may be expanded and caused to engage tissue engagement portions of the coupling device while in a relaxed configuration. An interior surface of the free ends may be exposed by at least moving the tissue engagement portions to a stressed configuration, and the tissue engagement portions may further be locked while stressed.

The first and second coupling devices and/or the exposed interior surfaces of the first and second ends may be advanced towards each other. The first coupling device can be coupled to the second coupling device such that the exposed interior surface of the second end is engaged against the exposed interior surface of the first end. Attaching the first coupling device to the second coupling device may also include inserting the tissue engagement portions of the first coupling device at least partially into the second coupling device and inserting the tissue engagement portions of the second coupling device at least partially into the first coupling device.

An installation tool for attaching a vessel to an anastomosis coupling device is also described and includes a vessel expander configured to about simultaneously expand a full perimeter of a vessel corresponding to a coupling device. A wing depressor may also be included and adapted to transition a plurality of movable wings of the coupling device between a pre-deployment configuration and a deployment configuration.

A clamp for attaching mating anastomosis couplings is also described and includes first and second supports for anastomosis couplings. A clamping mechanism configured to create a clamping force between the first support and the second support is also provided, as is a guide for facilitating movement of at least one of the first support or the second support.

An anastomosis kit is also described and includes first and second anastomosis couplings. The first end-to-end anastomosis coupling has movable wings and tissue engaging members. The second coupling is adapted to mate with the first end-to-end anastomosis coupling.

According to another exemplary embodiment, a vascular coupling may include a body that defines a central axis and extends between opposing first and second ends. A plurality of tissue engaging portions extend proximally from a first end of the body. The plurality of tissue engaging portions may be configured to be angled relative to the central axis. At tips of the engaging portions, a peripheral size may be defined. The plurality of tissue engaging structures may be configured to be deflected to a deflected position at which the proximal tips define a second, larger peripheral size. In at least some embodiments, the vascular coupling includes no moving parts but nonetheless is configured to have the plurality of tissue engaging portions move between multiple positions.

According to another example embodiment, a vascular coupling device may include a body defining an interior lumen with a central axis. At one end of the body are multiple tissue engaging structures that extend away from the body at an angle that is non-parallel relative to the central axis. Multiple receiving structures may also be at the one end of the body and arranged in an alternating pattern with the tissue engaging structures. The tissue engaging structures may be plastically deformed to an installation configuration in which the structures extend away from the body and generally parallel to the central axis. In some embodiments, there are no moving parts, but the tissue engaging structures can bend to the installation configuration: (a) without fracturing; and (b) without separating from the body; and (c) without fracturing the body.

According to another example embodiment, a method is disclosed for performing a vascular anastomosis. The exemplary method may include placing a free end of a vessel within a lumen of a body of a coupling device. The free end can be engaged with a plurality of tissue engaging members connected to, and extending from, the body of the coupling device. After or while engaging the free end of the vessel with said plurality of tissue engaging members, the plurality of tissue engaging members can be moved from a first position to a second position, with the second position having a larger size than the first position. Moving the tissue engaging members can include increasing a size of the free end of the vessel.

According to still another example embodiment, an installation tool may be useful for attaching a vessel to an anastomosis coupling device. An exemplary device can include a vessel expander configured to expand at least a portion of a vessel about a coupling device. At least one articulating member can be configured to draw the vessel expander into contact with the coupling device and transition tissue engagement members from pre-installation to installation configurations. The articulating member(s) may operate by using axial and/or pivotal motion. In some cases, a tapered member may expand the vessel and/or move the engagement members. In still other aspects, the installation tool can be a coupling device.

According to still another example embodiment, an anastomosis kit includes two vascular couplings. The first vascular coupling has multiple angled, inwardly directed tissue engaging members with no moving parts, and the second is configured to mate with the first vascular coupling.

In at least one embodiment, a vascular coupling device includes a body. The body may be substantially defined by a plurality of wing elements. The wing elements may be movable from a pre-installation configuration towards an installation configuration. The device may further include a plurality of tissue engaging structures moveably disposed relative to the plurality of wing elements. In some embodiments, the wing elements can change between a radial or disk configuration to an elongate or cylindrical configuration. The tissue engaging structures may move independent of the wing elements.

In another embodiment, a vascular coupling device is usable in an anastomosis procedure to provide exterior coupling of two portions of a vessel such that at least one portion of the vessel is held open during a vascular anastomosis procedure while further facilitating a tight seal between the two portions of the vessel and limiting a risk of thrombosis. A vascular coupling device can include a generally annular body substantially defined by at least six wing elements and at least six tethers between said at least six wing elements. The body may further define an interior lumen having a central axis. At least six tissue engaging members may be slideably disposed relative to the wing elements. At least six receiving members may be alternately disposed around the body with the tissue engaging members. The receiving members may be generally aligned with the tethers.

In accordance with some embodiments, a body of a vascular coupling device has an unstressed state. In the unstressed state, any one or more of the following may be true: (i) the body is substantially disk-shaped; (ii) the wing elements extend about radially relative to the central axis; (iii) the tissue engaging members extend about radially relative to the central axis; (iv) interior and exterior faces of the wing elements are about parallel; (v) interior faces are aligned along a length of the interior lumen; (vi) tissue engaging structures are moveable between retracted and depressed states; and (vii) tissue engaging structures define, in the depressed states, a first distance between interior tips thereof. In the stressed state, any one or more of the following may be true: (i) the body is substantially elongate; (ii) the tethers are in a stretched configuration; (iii) the wing elements extend about parallel relative to the central axis; (iv) the tissue engaging members extend about parallel relative to the central axis; (v) interior and exterior faces of the at least six wing elements are about parallel; (vi) interior faces are about perpendicular relative to the central axis; (vii) tissue engaging structures are moveable between retracted and depressed states; and (viii) tissue engaging structures define, in the depressed states, a second distance between interior tips thereof, the second distance being greater than the first distance.

In accordance with some embodiments, a method is disclosed for performing an anastomosis using a vascular coupling device. In the method, a first end of tissue is extended through a lumen of an annular body in a vascular coupling device. The vascular coupling device may include a plurality of tissue engaging members in a retracted position. In the method, a plurality of tissue engaging members of the vascular coupling device can be engaged against the first end, which may include depressing the tissue engaging members while substantially maintaining the annular body in a same configuration as when the first end of tissue was extended through the lumen. The first end of the tissue may be stretched by moving at least a portion of the annular body and the tissue engaging members in a radially outward direction. In some aspects, the stretched first end tissue is coupled to second tissue. Such coupling may be performed using a vascular coupling device attached to a mating anastomosis device.

In accordance with another embodiment, a method for performing an end-to-end anastomosis procedure is provided. In the method, a size of first and second vessels may be determined and matched with an internal lumen size of corresponding coupling devices. The coupling devices can be attached to respective vessels. Such attaching may include inserting a free end through an internal lumen of the coupling device while tissue engaging structures are retracted and a body is in a radial configuration. The tissue engaging structures can be engaged with the free end while maintaining said body of said first coupling device in the radial configuration. The free end can be expanded by changing said body to an elongated configuration. Expanding the free end can further include exposing an interior surface of the free end by at least moving tissue engagement structures to or towards a stressed configuration. Exposed interior surfaces of the vessels can be advanced towards each other, and the devices can be coupled together such that interior surfaces mate. Coupling can also include matching tissue engagement structures and receiving structures of corresponding devices.

In another embodiment, an anastomosis kit includes a first vascular coupling device with a body substantially defined by a plurality of movable wings. The device can also include multiple tissue engaging structures. The kit may further include a second vascular coupling device configured to mate with the first vascular coupling device. In some embodiments, the body may be separated into multiple pieces.

Additional features and advantages of example embodiments will be set forth in the description which follows, and in part will be obvious from the description, or may be learned by the practice of the invention. The features and advantages of the embodiments herein may be realized and obtained by means of the instruments and combinations particularly pointed out in the appended claims. These and other features of the present disclosure will become more fully apparent from the following description and appended claims, or may be learned by the practice of the invention as set forth hereinafter.

BRIEF DESCRIPTION OF THE DRAWINGS

Features and advantages of the embodiments of this disclosure will be apparent from the detailed description that follows, and which taken in conjunction with the accompanying drawings illustrate and describe exemplary features of the disclosure herein. It is understood that these drawings merely depict exemplary embodiments and are not, therefore, to be considered limiting of its scope. Additionally, the drawings are generally drawn to scale for some example embodiments; however, it should be understood that the scale may be varied and the illustrated embodiments are not necessarily drawn to scale for all embodiments encompassed herein.

Furthermore, it will be readily appreciated that the components of the illustrative embodiments, as generally described and illustrated in the figures herein, could be arranged and designed in a wide variety of different configurations, and that components within some figures are interchangeable with, or may supplement, features and components illustrated in other figures. Nonetheless, various particular embodiments of this disclosure will be described and explained with additional specificity and detail through the use of the accompanying drawings, in which:

FIGS. 8A-8E illustrate an example installation tool having a vessel expander and wing depressor, according to one example embodiment of the present disclosure;

FIGS. 25A-25D illustrate a process of securing a vessel to an exemplary vascular coupling device and using an installation tool according to another embodiment of the disclosure;

FIGS. 30A and 30B illustrate exemplary steps of a method for performing a vascular anastomosis.

DETAILED DESCRIPTION

The embodiments described herein generally extend to devices, apparatus, and methods for performing an end-toend vascular anastomosis. Some of the apparatus and assemblies of the present disclosure are configured to attach two ends of vasculature together in an anastomosis procedure and/or facilitate sealing of attached vasculature.

Challenges of traditional end-to-end anastomosis procedures may include the difficulty in working under the size constraints of micro-vasculature, and/or the placement of sutures in small vessels such that the vessel lumen remains open without a significant likelihood of thrombosis. Other challenges may include limitations on devices themselves which, by their nature, may be difficult to use with multiple types of vasculature and/or which may be difficult—if not impossible—to manufacture at a scale where it can be used microvascularly. By having a device that is manufacturable, and which can be efficiently and predictably used to couple vessels together, some of these challenges may be overcome. Such results, whether individually or collectively, can be achieved according to one embodiment of the present disclosure, by employing methods, systems, and/or apparatus as shown in the figures and described in detail below.

Reference will now be made to the drawings to describe various aspects of example embodiments of the disclosure. It is to be understood that the drawings are diagrammatic and schematic representations of such example embodiments, and are not limiting of the present disclosure. Moreover, while various drawings are provided at a scale that is considered functional for some embodiments, the drawings are not necessarily drawn to scale for all contemplated embodiments. No inference should therefore be drawn from the drawings as to any required scale.

Specific language will be used herein to describe the exemplary embodiments, nevertheless it will be understood that no limitation of the scope of the disclosure is thereby intended. It is to be understood that the drawings are diagrammatic and schematic representations of various embodiments of this disclosure, and are not to be construed as limiting the scope of the disclosure, unless such shape, form, scale, function or other feature is expressly described herein as essential. Alterations and further modifications of the inventive features illustrated herein, and additional applications of the principles illustrated herein, which would occur to one skilled in the relevant art and having possession of this disclosure, are to be considered within the scope of this disclosure. Furthermore, various well-known aspects of surgical procedures, anastomosis, micro-manufacturing and the like are not described herein in detail in order to avoid obscuring aspects of the example embodiments.

Figure 1:
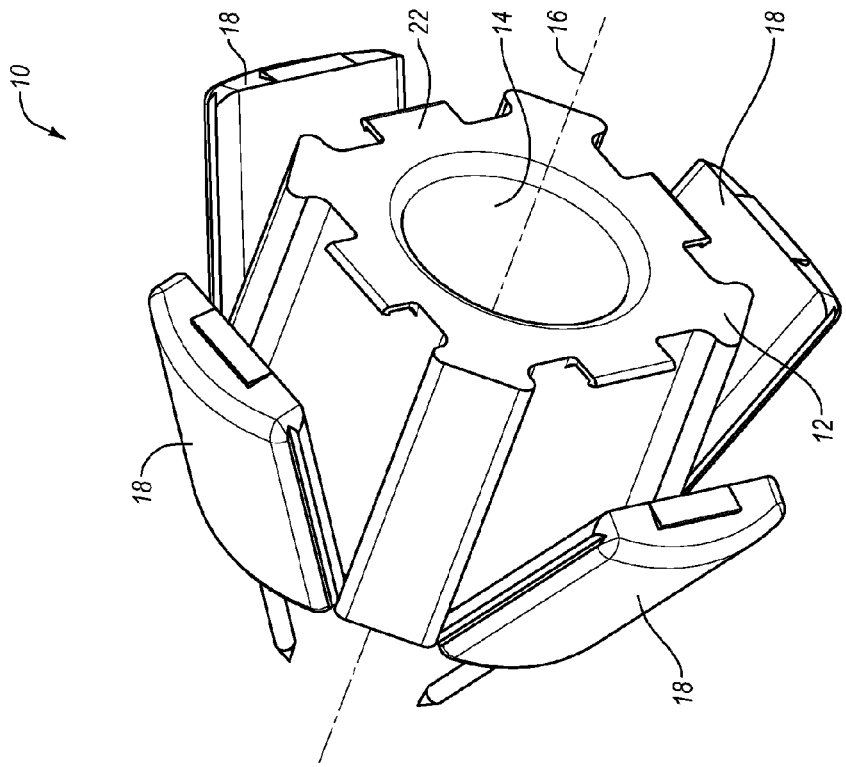
FIGS. 1 and 2 illustrate perspective views of an example vascular coupling device according to one embodiment of the disclosure.
Figure 2:
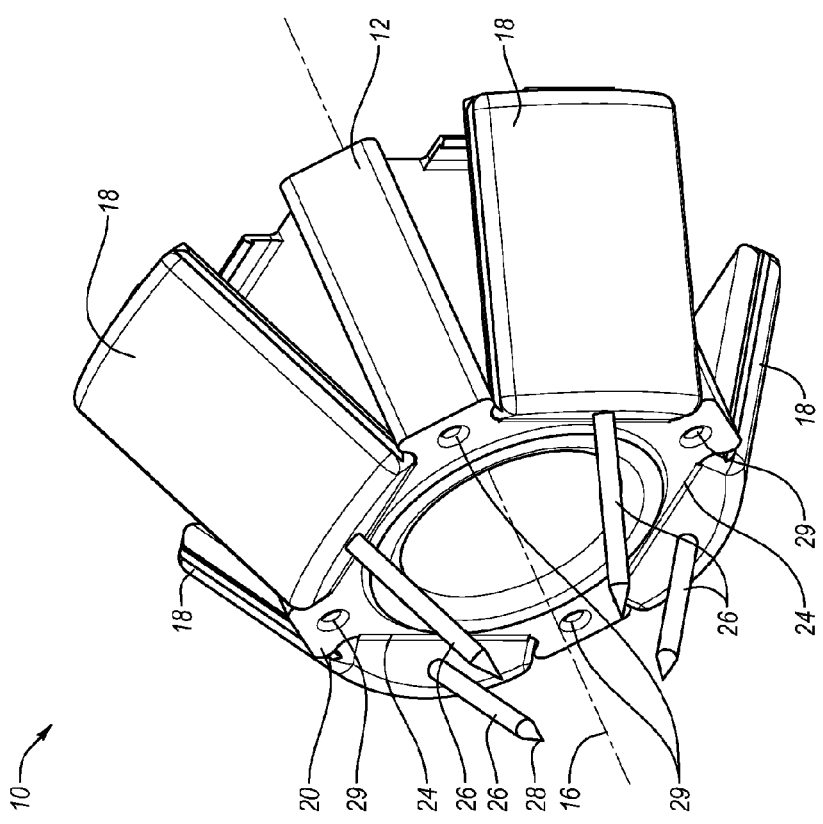

Turning now to the drawings, FIGS. 1 and 2 show various views of a first embodiment of a device 10 for use in performing an end-to-end anastomosis. Device 10 may be used for coupling ends of veins, arteries, tissue and other types of vessels or vasculature together, as well as with vasculature of different sizes. As shown in FIGS. 1 and 2, device 10 may include a body 12. In the illustrated embodiment, body 12 may be generally annular in shape and/or may generally surround a lumen 14 centered around a central axis 16. As used herein, an annular body may include any hollow body. For instance, an annular-shaped body may include one or more structures surrounding an opening, whether the body is substantially flat, has a significant thickness or depth, has a circular cross-sectional shape, or has a square, rectangular, hexagonal, or other cross-sectional shape. In other embodiments, body 12 may include other shapes and/or may not have a central axis 16.

Device 10 for performing an end-to-end anastomosis may include a plurality of wing elements 18 (also referred to herein as wings 18). In this embodiment, wing elements 18 are illustrated as extending from body 12. In some embodiments, wing elements 18 may engage the body at or near a proximal end 20 of body 12. Wing elements 18 may also be configured to rotate or otherwise move relative to body 12. For instance, wing elements 18 may be connected to body 12 through use of a hinge or pivot around which wing elements 18 may at least partially pivot. In some embodiments, wing elements 18 may pivot about one hundred eighty degrees around the hinge or pivot. In other embodiments, wing elements 18 may pivot from about five degrees to about three hundred fifty-five degrees.

In the present embodiment, there are four wings 18 that extend from body 12. Wings 18 of the illustrated embodiment may pivot relative to body 12 by using, for example, a living hinge 24. Accordingly, in at least one embodiment, wing elements 18 are integrally formed relative to body 12. The four wings 18 are also shown as being approximately equally angularly spaced at about ninety degree intervals around central axis 16. In other embodiments, however, wings 18 may not be equally angularly spaced and/or may be otherwise located relative to an outer perimeter of body 12. In still other embodiments, body 12 may include more or fewer than four wing elements 18, and/or the angular spacing between wings 18 may vary to be more or less than about ninety degrees.

As best shown in FIG. 2, distal end 22 of the body 12 may have an annular shape and a cross-sectional shape that is generally square. As best shown in FIG. 1, proximal end 20 of body 12 may have a similar or corresponding shape. For instance, in this embodiment, proximal end 20 of the body 12 also has a generally square cross-sectional shape that provides a hub for wings 18; however, the attachment of wings 18 at proximal end 20 of body 12 may give proximal end 20 a circular appearance.

Device 10 may also include a plurality of tissue engaging portions 26. Tissue engaging portions 26 of this embodiment extend from wings 18 and/or body 12. Tissue engaging portions 26 may include a tip portion 28. Portions of tissue engaging portions 26 and/or tip portion 28 may be sharp, barbed, or otherwise configured to engage and/or penetrate tissue.

In the present embodiment, tip portions 28 may be sharp to facilitate engaging tissue. In some embodiments where tip portion 28 is sharp, tip portion 28 may not only engage tissue, but may also penetrate the tissue. For instance, if device 10 for performing an end-to-end anastomosis were used with an end of an artery or vein, tip portions 28 may fully penetrate through a side wall of the artery or vein, and into the lumen of the vessel (although in some embodiments, tip portions 28 may only partially penetrate the tissue).

As illustrated in FIG. 2, tissue engaging portions 26 take the form of spikes that extend from the proximal end of wings 18. As illustrated, spiked tissue engaging portions 26 may be straight and can extend generally straight in a proximal direction from wings 18. Tissue engaging portions 26 may, however, take other forms. Tissue engaging portions 26 may instead have a curved, looped, L-shaped, or other configuration that may, for example, engage against and/or penetrate vascular tissue, a mating coupling device, or combinations thereof. Furthermore, one tissue engaging portion 26 may vary, for example, in size, shape, orientation, function, other characteristics, or combinations thereof, with respect to other tissue engaging portions 26 on the same device 10.

According to some embodiments of the present disclosure, device 10 may also include one or more receiving portions 29. Receiving portions 29 may be structured, arranged, and/or configured to receive all or a portion of a second component (such as device 10b shown in FIG. 5). For instance, a second component may be similar to device 10 and can include a plurality of tissue engaging portions, prongs, locks, or other devices. In the illustrated embodiment, receiving portions 29 include openings at proximal end 20 of body 12 and are approximately the same size as tissue engaging portions 26 or slightly smaller than tissue engaging portions 26. As described in more detail hereafter, similarly arranged tissue engaging portions of a second component may be configured to fit into receiving portions 29 and/or facilitate coupling between device 10 and a mating device or component. Receiving portions 29 may include openings that align device 10 and a second component, may act to interlock device 10 and the second component, provide any number of other functions, or combinations thereof. For instance, in one embodiment, receiving portions 29 may have a diameter slightly less than the diameter of the tissue engaging portions of a mating component, such that an interference fit may occur when the tissue engaging portions are positioned within receiving portions 29. In some embodiments, the walls of receiving portions 29 may be engaged by a barb or tip of the tissue engaging portions of a corresponding second component to secure device 10 to the mating component.

While a mating component may thus be similar or about identical to device 10, other embodiments are contemplated in which a mating device is significantly different with respect to device 10. For instance, device 10 as described herein may be used in connection with an end-to-end anastomosis procedure in which two ends of an artery, vein, tissue, or other vessel are coupled together. In such a case, a mating device similar to device 10 may be used. It need not be so, however, as a different type, style, configuration, or combination thereof may be used. In another embodiment, device 10 may be used in other types of anastomosis procedures, including a side-to-end anastomosis procedure. One skilled in the art in view of the disclosure herein can appreciate that a mating device may include a side wall of a mating vessel and/or a mating coupling device that facilitates side-to-end anastomosis in lieu of end-to-end anastomosis.

Figure 3:
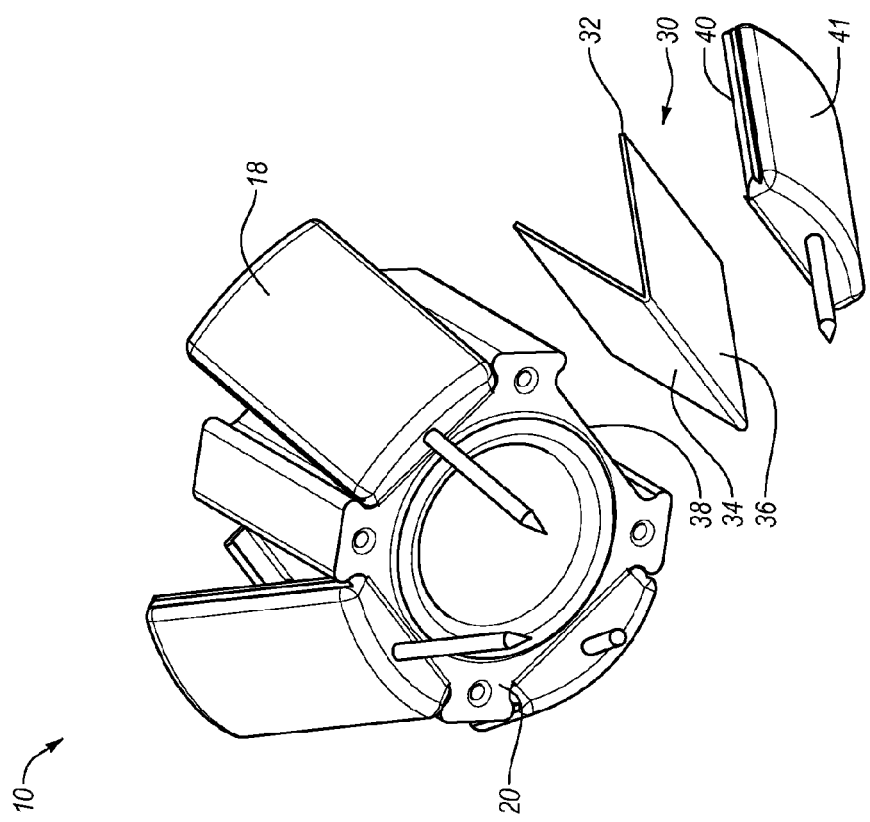
FIG. 3 illustrates an exploded view of portions of a biasing mechanism usable with the example vascular coupling of FIGS. 1 and 2.

FIGS. 1 and 2 depict device 10 in an arrangement that may correspond to a relaxed configuration. In the present embodiment, when device 10 is in a relaxed configuration, tissue engaging portions 26 may be directed radially inward (i.e., towards central axis 16). Device 10 may also include a biasing mechanism 30 that acts to keep device 10 in the relaxed configuration. As shown in FIG. 3, for instance, biasing mechanism 30 may include one or more springs 32. In this embodiment, spring 32 may be an angled spring that may connect to body 12 and/or to wings 18, although other types of springs or biasing mechanisms may be used. In this particular example embodiment, spring 32 may have a first angled plate 34 that engages against a generally planar outer surface 38 of body 12. A second angled plate 36 of spring 32 may engage against a corresponding generally planar interior surface 40 of wing 18. The generally planar outer surface 38 may act as a wing receptor on which wings 18 may be positioned in a deployed configuration.

According to the example embodiment illustrated in FIG. 3, spring 32 is angled towards proximal end 20 of body 12. In particular, first angled plate 34 and second angled plate 36 may be connected at an edge and form an angle. The front edge of spring 32 may generally be aligned towards proximal end 20 of body 12 such that spring 32 maintains a corresponding one of wings 18 at an angle relative to body 12. The angle between first and second angled plates 34, 36 of spring 32 may define the angle at which wings 18 are maintained in the relaxed configuration of device 10. For instance, first and second angled plates 34, 36 may define an acute angle between approximately twenty and seventy degrees. In some embodiments, first and second angled plates 34, 36 may define an acute angle between about thirty and sixty degrees.

In some embodiments, device 10 may be selectively placed in a stressed configuration. For example, wings 18 may be depressed with a force that overcomes the biasing force exerted by biasing mechanism 30. When depressed with such a force, wings 18 may partially rotate around hinge 24, such that the distal ends of wings 18 move inward (e.g., radially inward) towards central axis 16. If the inwardly directed force is sufficient, wings 18 may be placed in a stressed position in which interior surfaces 40 of wings 18 are placed proximate and generally parallel to outer surfaces 38 of body 12.

According to some embodiments, device 10 may be maintained in the stressed configuration permanently or for only a period of time. For instance, the stressed configuration may correspond to a deployed configuration. In the deployed configuration, wings 18 may be pressed inward to give the illustrated device 10 a generally cylindrical appearance. As discussed in more detail hereafter, the deployed configuration may also result in tissue engaging portions 26 rotating or otherwise moving relative to body 12. By way of example, where tissue engaging portions 26 are generally straight spikes, the spikes may rotate to be generally parallel to central axis 16.

Figure 4:
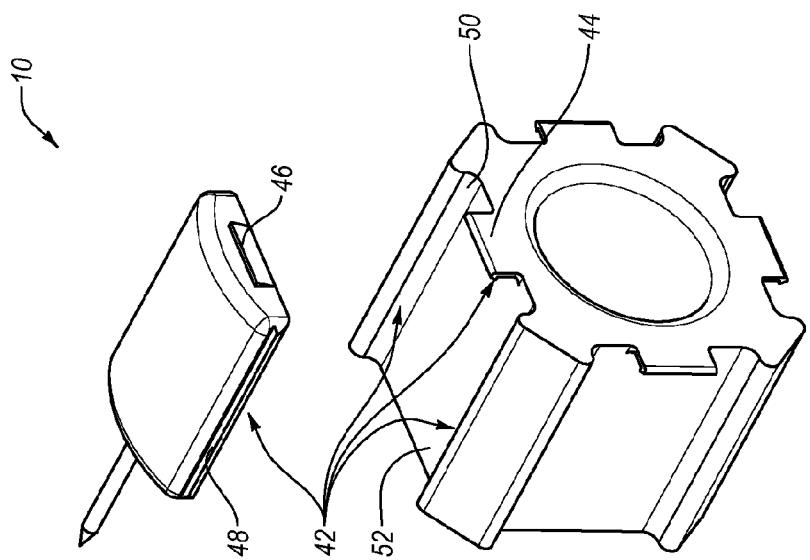
FIG. 4 illustrates an exploded view of portions of a locking mechanism usable with the example vascular coupling of FIGS. 1 and 2.

An external or internal force may be applied to maintain device 10 in the stressed or deployed configuration. As shown in FIG. 4, for instance, device 10 may include one or more locking mechanisms 42. Locking mechanism 42 may act to restrain wings 18 with respect to a particular location relative to body 12. In FIG. 4, for instance, locking mechanism 42 includes a distal locking tab 44 on body 12 of device 10. Distal locking tab 44 may be flexible to provide a snap-lock fit with wing 18. The illustrated embodiment, for instance, may include a corresponding distal detent 46 extending from a distal surface of wing 18. Distal locking tab 44 may be positioned to correspond to the location of distal detent 46 such that when distal end 22 of wing 18 is moved towards central axis 16, distal detent 46 engages distal locking tab 44. As distal locking tab 44 is engaged, at least a portion of distal locking tab 44 may flex distally outward. Distal detent 46 may include a shelf such that when wing 18 is depressed to or past a particular point, at least a portion of distal locking tab 44 is allowed to flex proximally inward. The shelf may then catch against distal locking tab 44. A biasing mechanism 30 (see FIG. 3) optionally exerts a force that presses the shelf against distal locking tab 44. The shelf may catch against distal locking tab 44 and/or exert a force that is overcome by distal locking tab 44. Thus, distal locking tab 44 may restrain wing 18 towards and/or in the stressed or deployed configuration.

Locking mechanism 42 may also include one or more other types of locking elements or other elements that facilitate restraining device 10 towards and/or in a stressed or deployed configuration. FIG. 4 further illustrates, for example, a side detent 48 formed on each side of wings 18. Side detent 48 may extend along all or only a portion of one or more sides of wings 18, and/or can be configured to engage against a corresponding side catch 50 formed on body 12. In this embodiment side detent 48 and side catch 50 operate in a manner similar to distal locking tab 44 and distal detent 46. For instance, as wing 18 is depressed and/or moved towards central axis 16, side detent 48 may engage against a side wall of a wing bed 52 formed in body 12. The side wall may flex to accommodate the side detent 48 of wing 18 and/or an interference fit may result. When wing 18 is depressed past a particular point, side detent 48 may catch against side catch 50. As a result, if a biasing mechanism, such as biasing mechanism 30, is present and exerts on wing 18 an outward force relative to central axis 16 (e.g., a radially outward force), side catch 50 may restrain wing 18 to substantially prevent or restrict movement of wing 18 towards the relaxed configuration.

It should be appreciated in view of the disclosure herein that the embodiments illustrated in FIGS. 1-4 are merely exemplary and that other embodiments are contemplated within the scope of this disclosure. Accordingly, other coupling devices may be within the scope of the present disclosure despite lacking one or more of the elements illustrated in, and described relative to, FIGS. 1-4.

For example, while the illustrated embodiment generally depicts device 10 as having a single-material construction, this is merely exemplary. In other embodiments, for instance, wings 18 may be formed of a different material, or formed separately from, body 12. By way of illustration, living hinges 24 may be optional and other types of hinges, pivots, other connectors, or combinations thereof may be used. For instance, in another embodiment, living hinges 24 may be removed and replaced by one or more pivot pins near proximal end 20 of body 12. In another embodiment, a groove may be formed in body 12. Wings 18 may include one or more pins or rollers that slide along the groove to effect movement of wings 18 relative to body 12.

Furthermore, while tissue engaging portions 26 are illustrated in FIGS. 1-4 as spikes having a generally straight construction, the shape of tissue engaging portions 26 may be varied in a number of different manners. For instance, in one embodiment, tissue engaging portions 26 may be shaped like hooks and can have a generally L-shaped, J-shaped, C-shaped construction, otherwise shaped construction, or combinations thereof. In still other embodiments, tissue engaging portions 26 may be curved, spiral, angled, otherwise constructed, or combinations thereof. The position and/or number of tissue engaging portions 26 may similarly be varied. Thus, while four tissue engaging portions 26 are illustrated, there may be more or fewer. In another embodiment, there may be between three and eight tissue engaging portions.

Tip 28 of tissue engaging portions 26 may also be constructed in a number of different manners. In the embodiment illustrated in FIGS. 1-4, for instance, tip 28 has a generally conical construction and comes to a proximal point. In other embodiments, one or more tips 28 may be blunt, rounded, barbed, fluted, otherwise arranged, or combinations thereof. For instance, tip 28 may have a barb or head portion that is configured to penetrate tissue and/or secure the tissue against tissue engaging portion 26. In still other embodiments, a barb, head, other securement mechanism, or combination thereof may be used to engage against a component that cooperates with device 10 in performing the anastomosis, and to facilitate securement of the other component to device 10.

Wings 18 and/or body 12 of device 10 illustrated in FIGS. 1-4 may also have different configurations, components, and arrangements depending on the particular embodiment employed. By way of illustration, locking mechanism 42 may be self-locking, but may be implemented in other manners that are self-locking or otherwise implemented. For instance, in some embodiments, a clamp or ring may be placed around body 12 and/or wings 18 to permanently and/or selectively secure wings 18 to body 12. In still other embodiments, a cotter pin, a hub, latch, or other securement mechanism may be used to secure any one or all of wings 18 to body 12.

It should also be appreciated in view of the disclosure herein that biasing mechanism 30 is merely exemplary. In other embodiments, for instance, biasing mechanism 30 may be wholly or partially excluded. When excluded, wings 18 may thus be free to move from a pre-deployed configuration towards the deployed configuration. In still other embodiments, angled plates 34, 36 may be replaced by a different type of spring, biasing mechanism, resistance mechanism, or combination thereof. Angled plates 34, 36 may, for instance, be replaced by a coiled spring, a tension line, a breakaway tether, some other mechanism, or a combination thereof.

Similarly, the shapes, sizes, configurations, number, other features of wings 18, or a combination thereof, may also be suitably varied and still remain within the scope of the present disclosure as contemplated herein. As one illustrative example, device 10 includes four wings 18 that are each centered at approximately ninety degree angular intervals. In other embodiments, however, there may be more or fewer than four wings 18. For example, there may be three or fewer wings, or there may be five or more wings.

Wings 18 in the illustrated embodiment are also shown as having a generally planar interior surface 40 and having an arcuate upper surface 41. In some embodiments the radius of curvature of arcuate upper surface 41 generally corresponds to the distance of upper surface 41 from the central axis 16. In other words, arcuate upper surface 41 may have a shape generally corresponding to a portion of a circle such that when device 10 is in an exemplary deployed configuration, device 10 may have a circular (e.g., cylindrical) appearance.

The illustrated and described shape of wings 18 is, however, only one possible configuration. In other embodiments, upper surface 41 may have a different radius of curvature, may have an irregular shape, may be flat or generally planar, may be otherwise varied, or a combination thereof.

The described embodiments of device 10 for facilitating an end-to-end vascular anastomosis may be manufactured using various manufacturing processes. In the embodiment illustrated in FIGS. 1-4, for instance, a micro-manufacturing process may shape body 12 and/or wings 18 out of a biocompatible material. For instance, exemplary biocompatible materials may include organic materials, metals, alloys, polymers, composites, and combinations thereof. According to one example, body 12 and/or wings 18 may be made from a biocompatible material such as silicone or high density polyethylene (HDPE). In other embodiments, biocompatible materials such as titanium, cobalt, platinum, nickel, stainless steel, other materials, alloys thereof, or combinations of the foregoing may also be utilized.

Body 12 and/or wings 18 may be designed to remain in the body indefinitely, or may degrade over time. For instance, body 12 and/or wings 18 may be formed of a biodegradable, bioerodable, bioresorbable, or other degrading or resorbing material or combinations thereof. Examples of such materials that may be suitable for the manufacture of device 10 may include copolymers, such as a copolymer of L-lactic acid and glycolic acid.

Tissue engaging portions 26 and/or biasing mechanism 30 may also be formed from any suitable material. Such materials may also be biocompatible and can include organic materials, metals, alloys, polymers, composites, or combinations thereof. Tissue engaging portions 26 and/or biasing mechanism 30 may also be a biodegradable, bioerodable, bioresorbable, or other degrading or resorbing material or combinations thereof. For instance, in one embodiment, tissue engaging portions 26 and/or biasing mechanism 30 may be formed from a polymer or a stainless steel alloy; however, in other embodiments, the tissue engaging portions may be formed from titanium, nickel, nickel-titanium alloy (e.g., NITINOL®), cobalt, chromium, platinum, or other materials, or combinations thereof. Furthermore, any or all portions of device 10 may, in some embodiments, be coated with other materials, such as biocompatible materials. For instance, the interior walls defining lumen 14 may be coated with a friction reducing material that allows vasculature to easily slide therein.

Device 10 may also, in some embodiments, be configured to deliver drugs or beneficial agents to the vessel, a site proximate the vessel, another location, or combinations thereof. For instance, therapeutic agents, pharmaceuticals and/or radiation therapies may be provided or facilitated by device 10. Device 10 and/or a coating material may contain a beneficial agent, drug, or other agent that may improve the use of device 10, the success rate of a procedure in which device 10 is used, other health or other aspects of a patient, or combinations thereof. Any number of different types of drugs, beneficial agents, balms, or other elements or components, or combinations thereof may have delivery facilitated by device 10. Examples may include antiallergic substances, antiarrhythmics, antibiotics, anticoagulants, antifibrins, anti-inflammatories, antimitotics, antineoplastics, antioxidants, antiplatelet agents, antiproliferatives, antisense agents, antithrombotics, cell adhesion inhibitors, cell permutation enhancers, endothelial cell recovery promoting agents, gene-based agents, growth factor inhibitors, hemostatic agents, hyperplasia inhibitors, oligonucleotides, radiopaque agents, smooth muscle proliferation inhibitors, thrombolytics, and combinations thereof.

The size of devices 10 described herein may also be varied. For instance, in one embodiment, the devices may be sized to accommodate arteries, veins, tissue, or other vessels in the range of about one millimeter to about four millimeters. The vessels may, however, be larger or smaller. For instance, the embodiments described herein can also accommodate vessels larger than four millimeters (e.g., between about four millimeters to about 20 millimeters).

Reference will now be made to an exemplary method for using device 10 of FIGS. 1-4 in performing an end-to-end vascular anastomosis according to one embodiment of this disclosure. The described method is generally illustrated with respect to FIGS. 5-7; however, it will be appreciated that other methods and/or devices may be used in accordance with embodiments of this disclosure. As discussed above, embodiments of the present disclosure may also be used in side-to-end anastomosis procedures, and/or other procedures.

Figure 5:
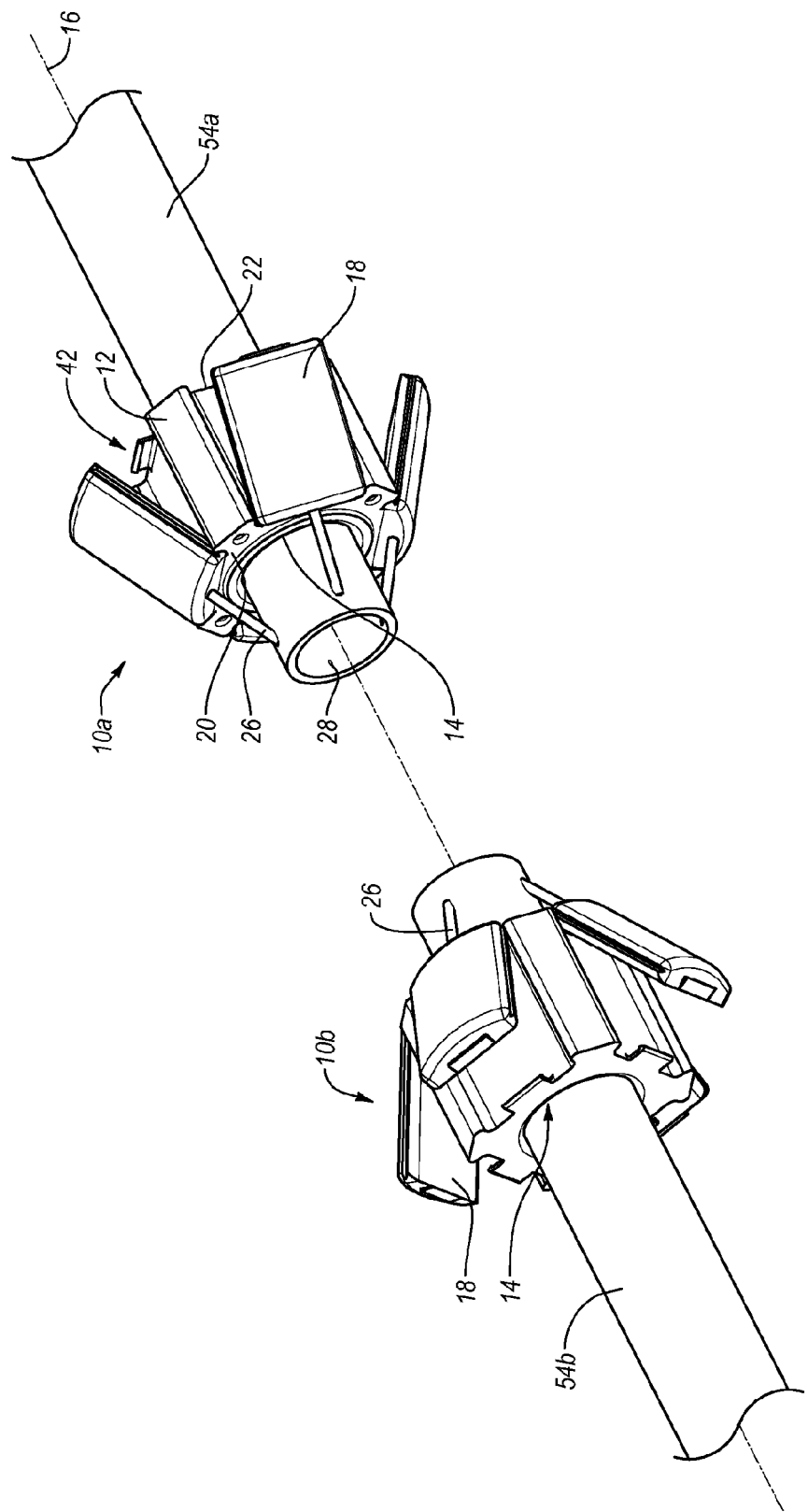
FIGS. 5-7 illustrate an example method for performing an end-to-end vascular anastomosis in accordance with one example embodiment of the present disclosure.

As shown in FIG. 5, a vessel 54 has been cut or otherwise separated into two vessel portions 54a, 54b. According to one method for performing an end-to-end vascular anastomosis, a free end of each of the two vessel portions 54a, 54b is associated with a corresponding one of devices 10a, 10b. For instance, in the illustrated embodiment, a first vessel portion 54a is associated with a first device 10a. First vessel portion 54a may be a blood vessel such as a vein or an artery, although the method is not so limited, and may be used in connection with other body vessels and/or organs.

In FIG. 5, first vessel portion 54a has been associated with first device 10a by passing first vessel portion 54a through lumen 14 within body 12 of first device 10a. In some embodiments, the size of lumen 14 may correspond to the size of first vessel portion 54a. For instance, prior to inserting first vessel portion 54a through lumen 40, calipers, a measuring gage, or another measuring device may be used to determine an approximate diameter of first vessel 54a. For instance, a surgeon or other person participating in the vascular anastomosis treatment may select a device 10a that has a lumen diameter approximately matching the external diameter of first vessel portion 54a. Device 10a may be available in a number of different sizes, and optionally may be color coded so that a particular color of a device or packaging corresponds to a particular size of lumen 14. Accordingly, within the described method, a measurement of first vessel portion 54a and a selection of a particular size of device 10a may be performed.

As first vessel portion 54a is positioned within lumen 14 of device 10a, first vessel portion 54a may be inserted at distal end 22 and moved towards proximal end 20 of body 12. As first vessel portion 54a moves in a proximal direction, the free end of first vessel portion 54a may pass fully through body 12. In passing first vessel portion 54a through body 12 in this manner, first vessel portion 54a may engage against one or more of tissue engaging portions 26. In the illustrated embodiment, for instance, tissue engaging portions 26 may be spikes that extend in a proximal direction from each of four wings 18. Wings 18 may, in this embodiment, be angled in a manner that also causes tissue engaging portions 26 to angle inward and towards central axis 16.

One aspect of tissue engaging portions 26 is that they may be adapted to engage the wall of first vessel portion 54a, and optionally pass fully or partially through a wall thickness of first vessel portion 54a. In FIG. 5, for instance, tissue engaging portions 26 may pass through the full wall thickness and enter into the interior of first vessel portion 54a, although in other embodiments, tissue engaging portions 26 may pass only partially through the wall thickness.

Tissue engaging portions 26 may be caused to engage and optionally penetrate the wall of first vessel portion 54a in any suitable manner. In one embodiment, for instance, wings 18 of device 10a are depressed inward relative to central axis 16. By depressing wings 18 in this manner, tip 28 of tissue engaging portions 26 may move radially outward relative to central axis 16. As tip 28 moves a sufficient distance radially, lumen 14 may become open such that first vessel portion 54a may pass through lumen 14 without being obstructed by tissue engaging members 26.

Once first vessel portion 54a is in a position similar to that illustrated in FIG. 5, wings 18 may be released. In embodiments in which wings 18 are biased towards a relaxed or pre-deployment configuration, wings 18 may rotate relative to central axis 16 such that tips 28 of tissue engaging portions 26 move radially inward relative to central axis 16. As tips 28 move inward, they may engage against and potentially penetrate the wall of first vessel portion 54a. In embodiments in which wings 18 are not biased, wings 18 may be manually moved to a position in which tissue engaging portions 26 engage first vessel portion 54a.

The degree to which wings 18 may be angled with respect to central axis 16 may be varied. For instance, wings 18 may have a different angle if the length of tissue engaging portions 26 is varied. Accordingly, while FIG. 5 illustrates wings 18 at approximately a forty-five degree angle relative to central axis 16, this is merely illustrative and not restrictive. For instance, in other embodiments, wings 18 may be rotated about ninety degrees relative to central axis 16 so as to engage first vessel portion 54a a desired amount. A greater or lesser angle may also be used. In still another embodiment, approximately a thirty degree angle may exist between wings 18 and central axis 16 for a desired engagement to occur. Desired engagement between first vessel portion 54a and tissue engaging portions 26 may thus occur at any of numerous different angles of wings 18, including angles between about ten and about one-hundred twenty degrees. Wings 18 may even angle up to, and possibly past, one hundred eighty degrees in some embodiments.

It should also thus be appreciated that the distance between tips 28 of tissue engaging portions 26 may thus vary based on the position of wings 18. For instance, in a relaxed or pre-deployment configuration, tips 28 of tissue engaging portions 26 may be directed inward and generally separated by a first distance. As wings 18 rotate or otherwise move and tissue engaging portions 26 move therewith, tips 28 may move outward, thereby causing the distance between tips 28 to increase.

The previously described manner for causing tissue engaging portions 26 to engage first vessel portion 54a is merely one example. For instance, wings 18 may begin in a stressed or deployed configuration through the use of locking mechanism 42. When first vessel portion 54a is in a suitable position, locking mechanism 42 may be selectively released, thereby allowing wings 18 to move into a relaxed configuration and causing tissue engaging portions 26 to engage the walls of first vessel portion 54a.

In other embodiments, first vessel portion 54a may be relatively flaccid and/or collapsed as it is moved through lumen 14 in body 12. As a result, the size of first vessel portion 54a may be collapsed such that it can pass through lumen 14 and out proximal end 20 of body 12 with limited resistance from tissue engaging portions 26, even when wings 18 are in a relaxed configuration. In such a case, an expander may then be inserted into the free end of first vessel portion 54a. The expander may cause the walls of first vessel portion 54a to expand radially outward. As the walls of first vessel portion 54a expand outward, they may then engage against tips 28 of tissue engaging portions 26. As expansion of the walls continues, additional engagement may occur. The expander may take any suitable form and may, for example, mechanically expand the walls of first vessel portion 54a, may direct air or another fluid into the lumen of first vessel portion 54a, or otherwise cause the vessel walls to expand.

Regardless of the manner in which first vessel portion 54a is caused to be engaged with tissue engaging portions 26, first device 10a and first vessel portion 54a may become engaged in a manner similar to that illustrated in FIG. 5. For simplicity, the particular manner in which second vessel portion 54b is engaged with second device 10b is not described; however, it will be appreciated that devices 10a, 10b may operate in similar manners.

Figure 6:
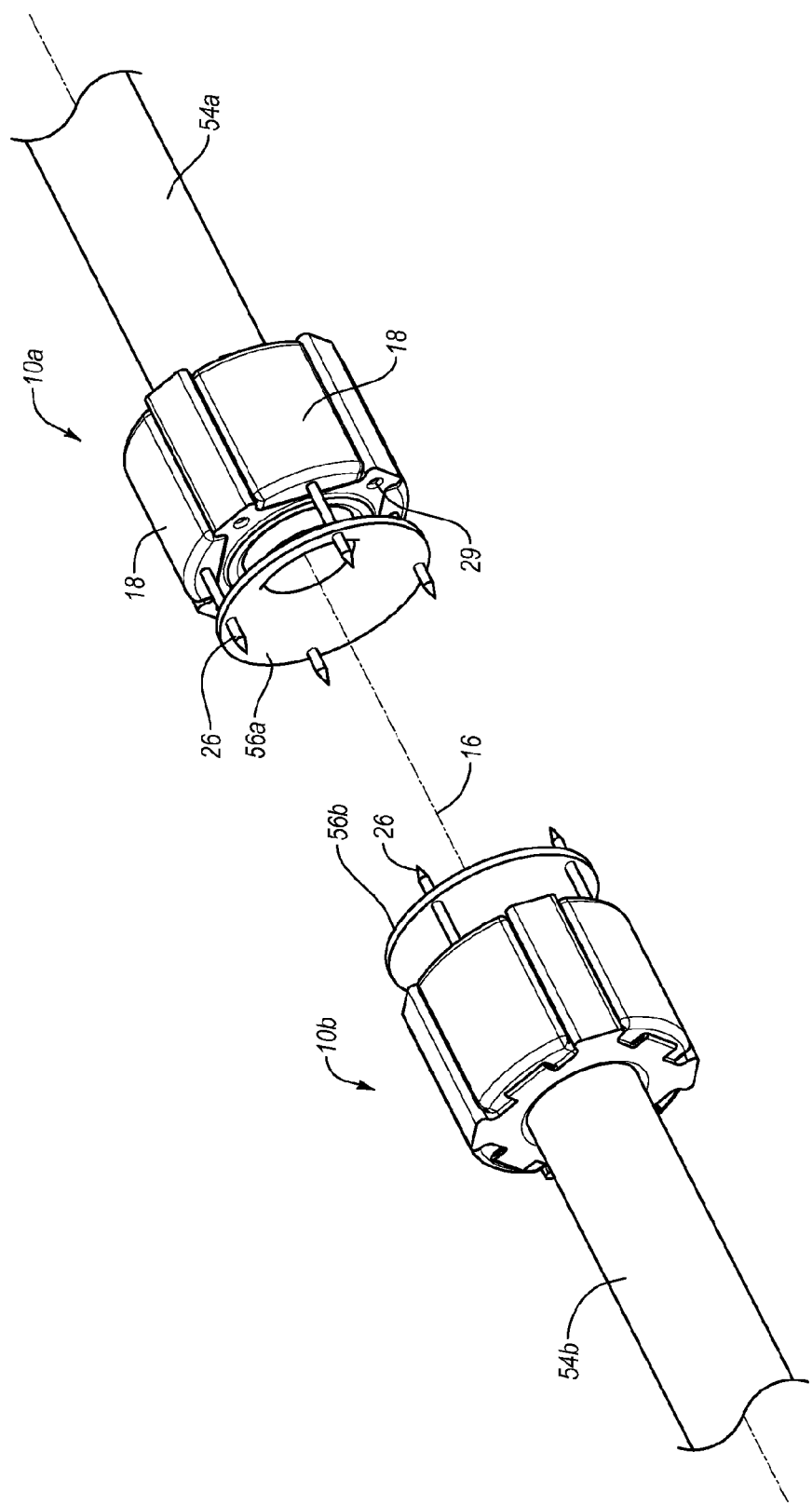

Turning now to FIG. 6, an additional example act in a method for performing a vascular anastomosis is described in additional detail. As shown in FIG. 6, first and second devices 10a, 10b continue to be engaged or otherwise connected with two vessel portions 54a, 54b. Compared with the position of wings 18 in FIG. 5—which may correspond generally to a relaxed configuration of device 10a—wings 18 have been moved (e.g., rotated) relative to central axis 16 that runs longitudinally through device 10a and first vessel portion 54a. In particular, in this example embodiment, wings 18 have been rotated to be approximately parallel to central axis 16.

In rotating wings 18 to the illustrated position, tissue engaging portions 26 may also rotate. Where tissue engaging portions 26 are spikes similar to those illustrated and/or extend parallel to wings 18, tips 28 of tissue engaging portions 26 may rotate or otherwise move radially outward to be generally parallel to central axis 16. In some cases, tips 28 of tissue engaging portions 26 may have penetrated at least a portion of first vessel portion 54a. In the illustrated embodiment, for instance, four tissue engaging portions 26 have each penetrated the exterior wall of first vessel portion 54a. The four tissue engaging portions 26 may further grip or otherwise maintain such engagement and/or penetration with first vessel portion 54a as tissue engaging portions 26 are moved.

When tissue engaging portions 26 move while maintaining engagement with first vessel portion 54a, the wall of first vessel portion 54a may be expanded. For instance, in FIG. 6, the proximal end of the wall of first vessel portion 54a is expanded by tissue engaging portions 26 to increase the overall diameter of first vessel portion 54a. Expansion of first vessel portion 54a may result in interior surface 56a of first vessel portion 54a being everted, such that interior surface 56a is at least partially exposed at proximal end 20 of device 10a. Thus, in embodiments being used in connection with vascular applications, everting interior surface 56a may include everting the intimal layer of the vessel.

With wings 18 depressed to the illustrated position, device 10a may be in a stressed and/or deployed configuration. If wings 18 are released, wings 18 may return to an unstressed or relaxed configuration; however, in some embodiments, a locking mechanism may cause wings 18 to remain in the deployed configuration permanently, or until the locking mechanism is selectively released.

In some embodiments, the method for performing a vascular anastomosis may also cause wings 18 to be locked in position. For instance, device 10a of the illustrated embodiment includes four receiving portions 29 that may include openings or holes angularly spaced around device 10a. In this embodiment, the four tissue penetrating portions 26 and the four receiving portions 29 are alternately spaced around central axis 16 of device 10a. A mating second device 10b may be connected to a second vessel portion 54b in a manner similar to that described for first device 10a and first vessel portion 54a. Second device 10b may be rotated relative to first device 10a, such that tissue engaging portions 26 of second device 10b are generally aligned with receiving portions 29 of first device 10a. Corresponding alignment between tissue engaging portions 26 of first device 10a may also be made with receiving portions of second device 10b.

Receiving portions 29 illustrated in FIG. 6 may be holes, and may have a generally circular cross-sectional shape along all or a portion of the length thereof. Receiving portions 29 may, however, have any number of other configurations, sizes, shapes, other features, or combinations thereof. For instance, a receiving portion may be a slot, a male or female connector, a twist lock feature, some other feature, or a combination thereof. Further, one or more of receiving portions 29 may have a shape, size, configuration, other feature, or combination thereof, that varies with respect to other receiving portions 29 on the same device 10a.

Figure 7:
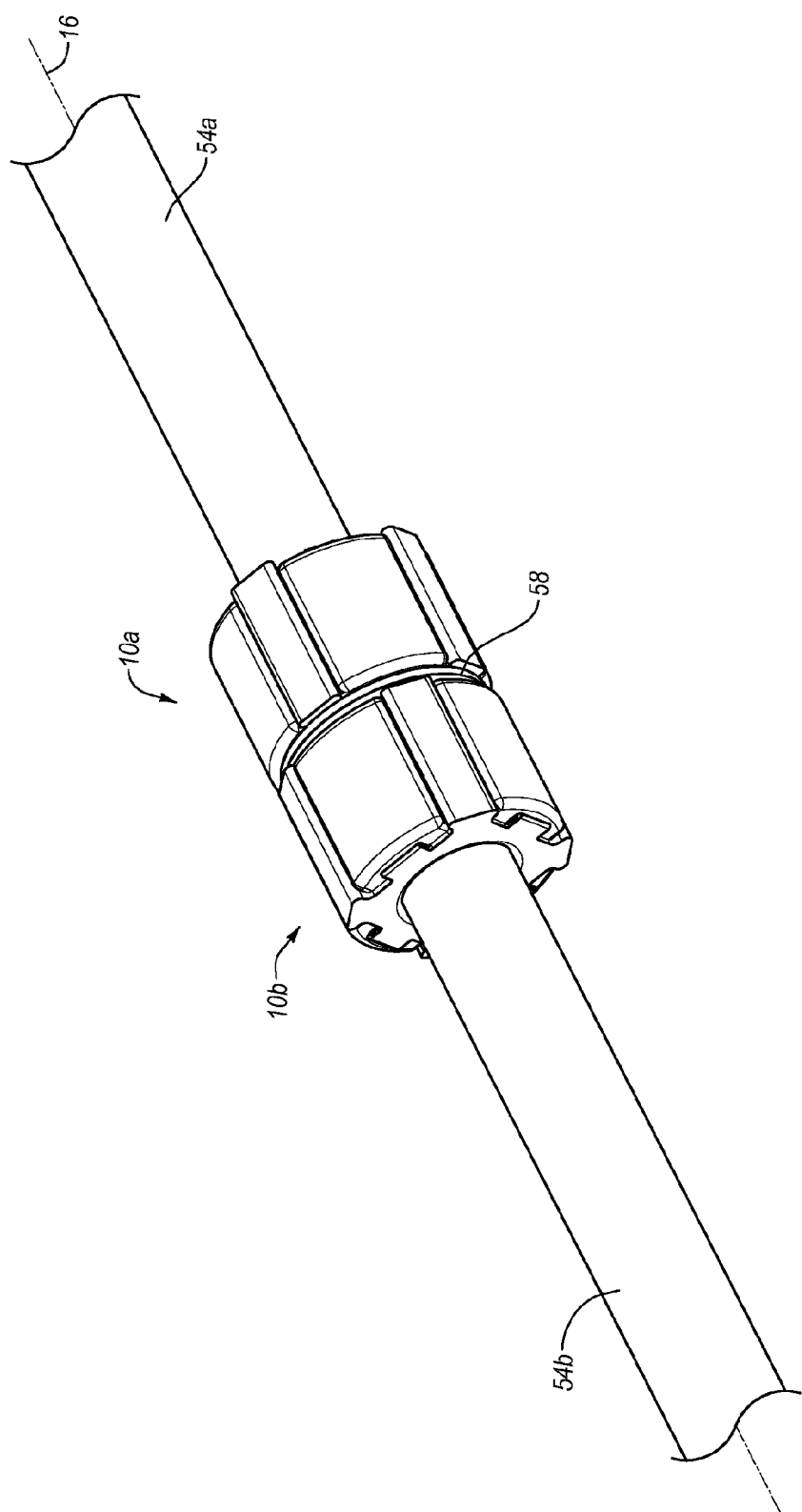

When corresponding tissue engaging portions 26 and receiving portions 29 are aligned, first and second devices 10a, 10b may be drawn together as shown in FIG. 7. As first and second devices 10a, 10b move towards each other, tissue engaging portions 26 may enter receiving portions 29. Further advancement of first and second devices 10a, 10b towards each other may also cause the exposed ends of first and second vessel portions 54a, 54b to engage. As noted previously, interior surfaces 56a, 56b (see FIG. 6) of first and second vessel portions 54a, 54b may have been exposed at the respective free ends thereof. Consequently, when the free ends are drawn into contact, an intima-to-intima contact may be formed, which may achieve a substantially tight seal at interface 58 between first and second vessel portions 54a, 54b.

As discussed herein, first and second devices 10a, 10b may be maintained in their deployed and coupled state for an indefinite period of time to facilitate sealing between first and second vessel portions 54a, 54b, and to effectively couple first and second vessel portions 54a, 54b in an end-to-end vascular anastomosis. For instance, tissue engaging portions 26 may form an interference fit with corresponding receiving portions 29 such that first and second devices 10a, 10b are maintained in the coupled state.

While the illustrated embodiment generally illustrates substantially identical first and second devices 10a, 10b, it should be appreciated that this is merely one example in which devices and methods of the present disclosure may be used. For example, in other embodiments, first and second devices 10a, 10b may have different sizes, be differently shaped, have varying configurations, or a combination thereof. By way of illustration, it is not necessary that the end-to-end anastomosis be performed by coupling first and second vessel portions 54a, 54b of the same size. One vessel portion may be of a smaller size than the other, such that interior lumen 14 of one of devices 10a, 10b may be a different size than that of the other of devices 10a, 10b.

In still other embodiments, devices 10a, 10b may have other coupling mechanisms. For instance, the devices may facilitate a male/female connection, with one of the devices having a male connector and the other device including a female connector. In other embodiments, the tissue engaging portions may have a different configuration. For instance, the tissue engaging portions may include a hook. The hook may in turn be received within a receiving slot in a mating device. Upon thereafter advancing (e.g., rotating) the coupling devices relative to each other, the hook may travel within a channel connected to the device, such that the two mating couplers are securely attached to each other in a manner that facilitates sealing between the two ends of the joined vessel.

The devices and apparatus described herein may be used in isolation but may also be used in connection with one or more other devices and/or apparatus. For instance, in some embodiments, an expander is used to expand the vessel and/or to facilitate engagement of the vessel by corresponding tissue engaging portions. In other instances, a clamp device may be used to align two coupling devices and/or facilitate engagement of mating coupling devices in an anastomosis treatment. In still other embodiments, coupling devices, expanders, clamp devices, or a combination thereof may be provided together as a kit.

Figure 8A:
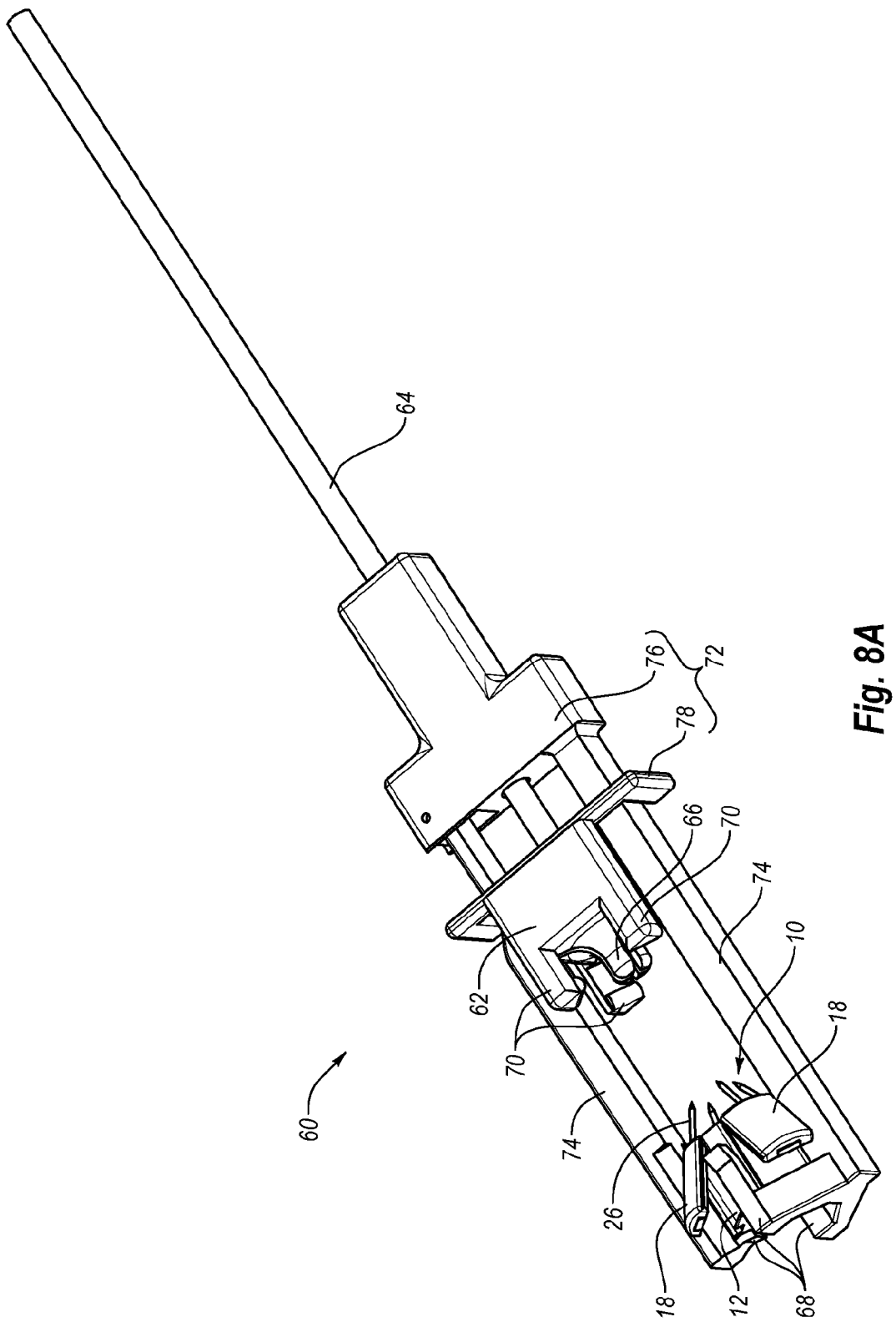
Figure 8D:
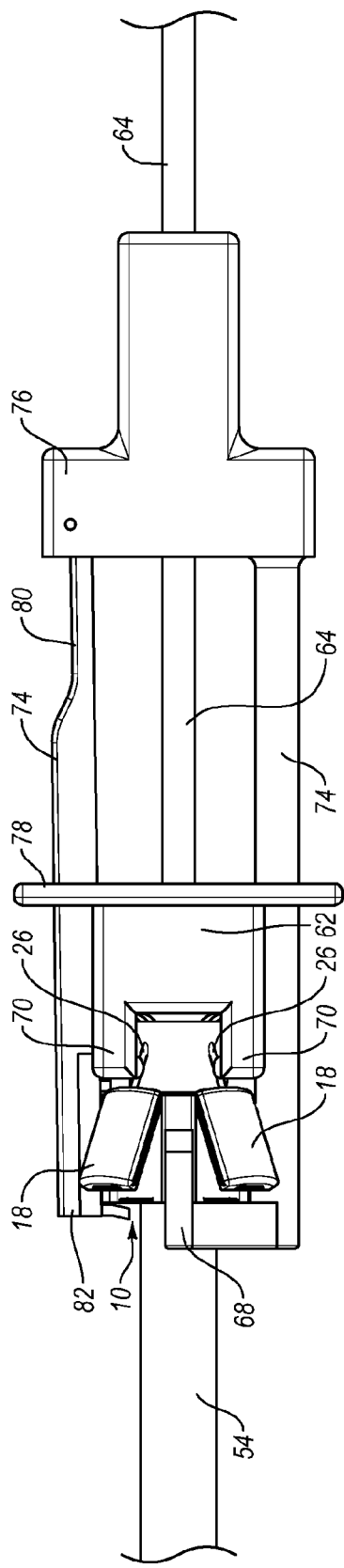
Figure 8E:
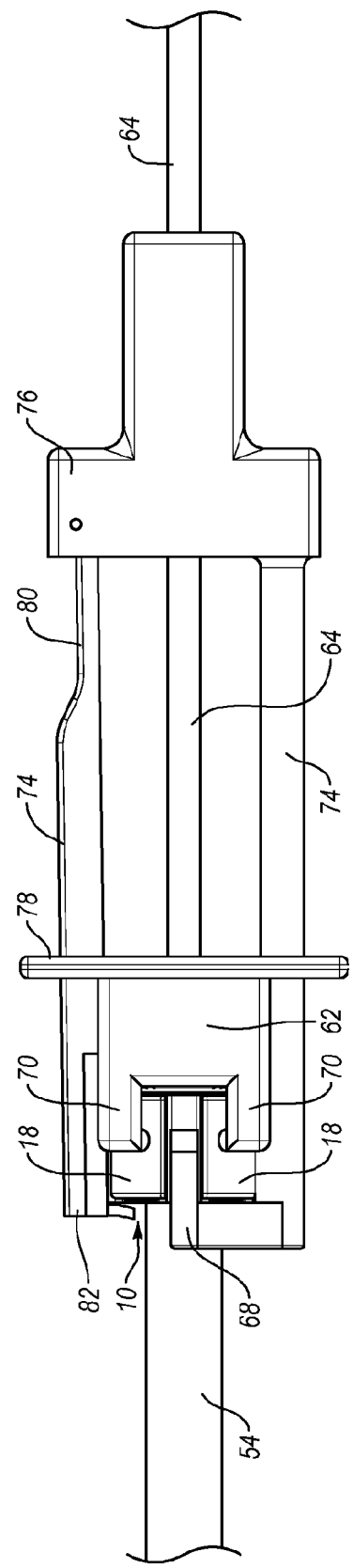
Figure 9:
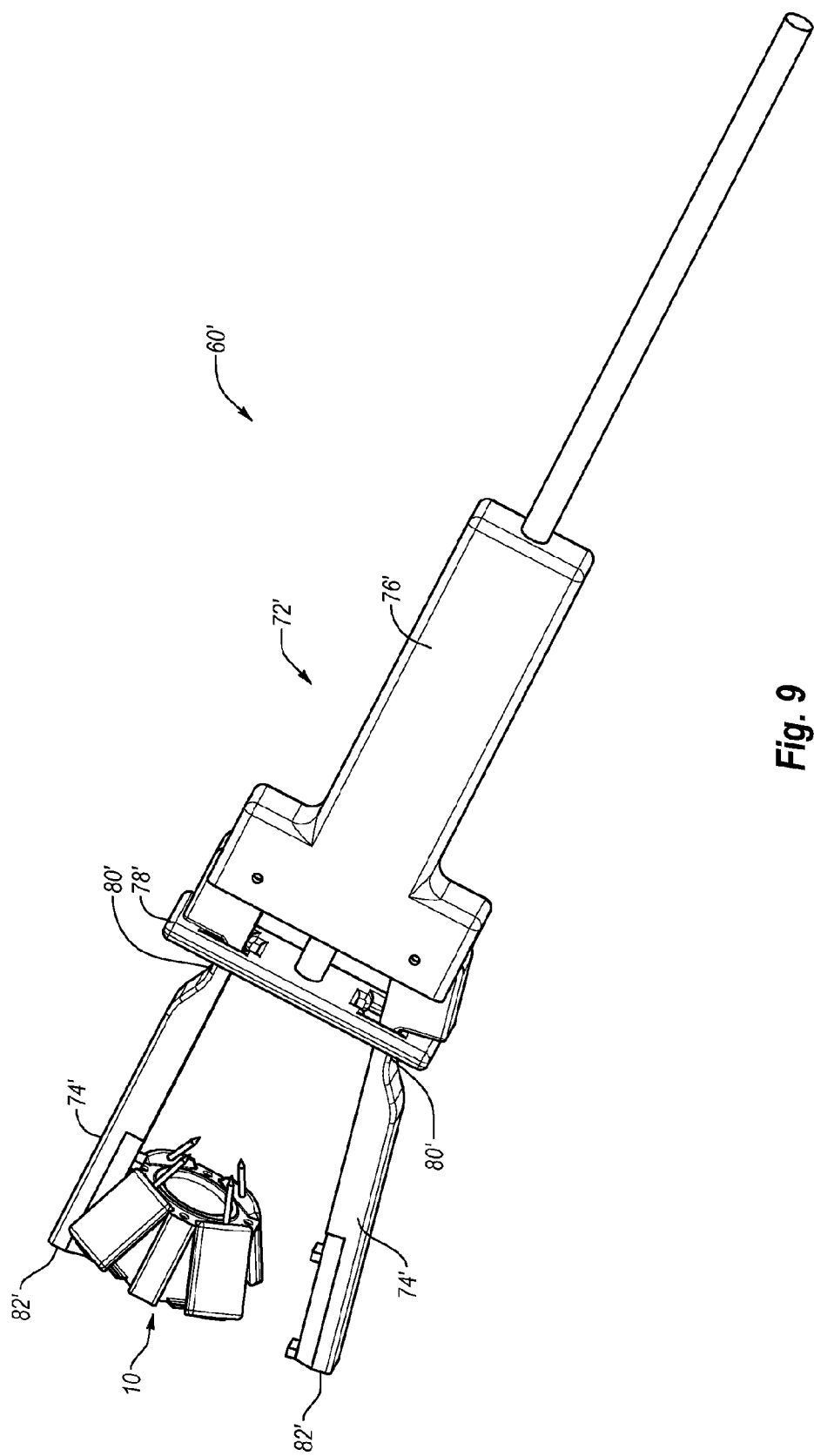
FIG. 9 illustrates another example installation tool with two movable guides, according to one example embodiment of the present disclosure.

FIGS. 8A-9, for instance, illustrate exemplary installation tools. More particularly, FIGS. 8A-8E illustrate an exemplary installation tool 60 and a method of using installation tool 60, and FIG. 9 illustrates an additional exemplary embodiment of an installation tool.

Installation tool 60, shown in FIGS. 8A-8E, is multifunctional and can perform or facilitate multiple acts of an installation and/or preparation method for device 10. In FIG. 8A, for instance, installation tool 60 can be used to facilitate engagement between a vessel and tissue engaging portions of device 10, as well as depress wings 18 so as to transition device 10 from a relaxed configuration towards and/or to a deployment configuration. Installation tool 60 may further automate engagement between the tissue engaging portions of device 10 and the tissue, such that it is not necessary for all embodiments that each of the tissue engaging portions be separately engaged with the vessel. For example, the tissue can be expanded at a generally constant rate such that all of the tissue engaging portions are automatically engaged with the tissue substantially simultaneously.

As shown in FIG. 8A, installation tool 60 includes an exemplary vessel expander 62 and an expander shaft 64 that couples to vessel expander 62. Vessel expander 62 may include a tapered end 66 that is directed towards a coupler support 68. In this embodiment, coupler support 68 is illustrated as holding or otherwise supporting device 10. Device 10 may be supported by installation tool 60 in a relaxed configuration and/or a deployed configuration.

Shaft 64 may act as a grip that enables an operator to control and/or manipulate vessel expander 62. For instance, as shown in FIGS. 8A-8E, shaft 64 may be moved towards device 10 and coupler support 68, thereby also causing tapered end 66 of vessel expander 62 to move towards device 10. As shown in FIG. 8C, device 10 may have a vessel 54 such as a vein, artery, organ, body lumen, or the like extended therethrough, and a free end of vessel 54 may extend from device 10 and away from tapered end 66. Tapered end 66 is, in this embodiment, tapered such that the end most near device 10 has a smaller diameter or other dimension than the end most near expander shaft 64. In this manner, the smaller diameter portion of tapered end 66 may enter vessel 54 even if vessel 54 is collapsed.

Further extension of expander shaft 64 towards vessel 54 may cause the larger dimension portion of vessel expander 62 to enter vessel 54. For instance, as shown in FIG. 8D, as the larger portion of tapered end 66 is moved inside vessel 54, vessel 54 may expand to accommodate the increased size of tapered end 66. In some embodiments, tapered end 66 may be generally circular or have another configuration that causes generally uniform expansion of vessel 54.

As vessel 54 expands, the vessel wall may move radially outward relative to a longitudinal axis of vessel 54 and/or tapered end 66. The radial expansion of the vessel walls can be seen by comparing vessel 54 in FIGS. 8C and 8D. As shown in FIG. 8D, the radial expansion of the vessel walls may cause the vessel walls to expand and engage against various tissue engaging portions 26 that are attached to wings 18 of device 10. With sufficient expansion of vessel 54, tissue engaging portions 26 may penetrate at least a portion of the vessel wall. In other embodiments, tissue engaging portions 26 may penetrate at least a portion of the vessel wall in the absence of expansion of vessel 54.

With the vessel wall engaged by tissue engaging portions 26, installation tool 60 may be used to transform device 10 from a relaxed configuration to a deployed configuration. In the relaxed configuration, as illustrated in FIGS. 8A-8D, wings 18 of device 10 may be at an angle relative to body 12 of device 10. For instance, wings 18 may be at an angle between about twenty and about eighty degrees relative to a longitudinal axis of body 12.

Translation (e.g., rotation) of wings 18 may, in some embodiments, cause tissue engaging portions 26 to further expand vessel 54 engaged thereby. In some embodiments, the further expansion of vessel 54 may expose an interior surface to facilitate an intima-to-intima contact. The particular installation tool 60 illustrated in FIGS. 8A-8E can include a set of one or more wing depressors 70 that may be used to depress wings 18 of device 10, or otherwise place device 10 in a deployed state. By way of illustration, four wing depressors 70 may be connected to a carrier 72. Carrier 72 may be at least partially movable along one or more guides 74. Guides 74 may, for instance, direct the path which carrier 72 and/or wing depressors 70 may take either towards or away from device 10.

In this embodiment, carrier 72 may be moved towards device 10, as shown in FIGS. 8C-8E, thereby causing wing depressors 70 to come into contact with wings 18 of device 10 as shown in FIG. 8E. Wing depressors 70 may be located at a position generally corresponding to the positions of wings 18 as held in place by coupler supports 68. Moreover, wing depressors 70 may have a radial position that generally corresponds to the outer radius of device 10 at proximal end 20 of device 10. In some embodiments, wing depressors 70 have an elongated shape. Wing depressors 70 may thus engage wings 18 at a proximal end of device 10 and continue to advance distally along device 10. As the radial location of wing depressors 10 may be fixed, wing depressors 70 can engage and depress wings 18, which may cause the distal edges of wings 18 to move radially inward. As discussed elsewhere herein, in some embodiments, wings 18 may be depressed to a position in which they become locked in place through a self-locking mechanism, or may be placed in a deployed configuration in which an external or other locking mechanism can be employed to lock wings 18 in a deployed configuration.

Depression of wings 18 may rotate tissue engaging members 26 in a manner that expands engaged vessel 54 and/or otherwise prepares vessel 54 for an anastomosis (e.g., end-to-end, side-to-side, or other anastomosis or other procedure). For instance, depressing wings 18 with wing depressors 70 may rotate tissue engaging members 26 so that vessel 54 is expanded in a manner similar to that shown in FIG. 6. Carrier 72, including wing depressors 70 and vessel expander 62, may then be moved away from device 10 and the expanded vessel 54. Device 10 and vessel 54 may then be removed from installation tool 60 and the anastomosis or other procedure may be completed.

Any of a number of different materials may also be used to make or produce installation tool 60. For instance, in some embodiments, installation tool 60 may be formed of a polymer, natural or organic material, metal, alloy, composite, or other material, or a combination thereof. In one example embodiment, wing depressors 70 may be formed of a rigid material that can depress wings 18 of device 10, while some or all other portions of installation tool 60 are formed of a flexible or less rigid material.

As illustrated in FIGS. 8A-8E, guides 74 may, in some embodiments, have a tapered configuration, or some other configuration where the width or other measurements of guides 74 changes along their longitudinal length. For instance, guides 74 may have a first width at proximal end 80, and the width may increase along all or a portion of the length of guides 74. A variable width in guides 74 may serve any of a number of different purposes. For instance, an increase in the width of guides 74 at or near distal end 82 of guides 74 may allow guides 74 to act as a stop to prevent or restrict movement of carrier 72.

As best illustrated in FIG. 8B, a decreased width or other measurement at or near proximal end 80 of guides 74 may also allow installation tool 60 to open to receive device 10 therein. By way of illustration, carrier 72 may include a sliding component 78. Sliding component 78 may, for example, include one or more openings, channels, gaps, apertures, other features, or combinations thereof through which guides 74 are received. The openings may be sized to accommodate a maximum width of guides 74. In some embodiments, guides 74 may be configured to pivot or otherwise move relative to carrier 72 (e.g., relative to a stationary portion 76 of carrier 72). When the openings of sliding component 78 are positioned over a wider portion of guides 74, sliding component 78 may prevent or otherwise restrict motion of guides 74 relative to stationary portion 76. If, however, the openings of sliding component 78 are positioned over a narrower width of guides 74, the size of the openings may allow guides 74 to pivot, thereby opening installation tool 60 to receive device 10 therein, as illustrated in FIG. 8B.

As illustrated in FIGS. 8A-8E, installation tool 60 may be configured so that only one of two guides 74 may change size and/or shape and/or be configured to pivot or otherwise move. However, an installation tool may be designed to allow multiple guides to move or pivot. For instance, FIG. 9 illustrates an installation tool 60' that is similar in many respects to installation tool 60. Installation tool 60' includes a carrier 72' with two guides 74' extending therefrom. Guides 74' may support device 10 as discussed herein. Installation tool 60' may also include a sliding component 78' that is movable between proximal and distal ends 80', 82' of guides 74'. While not illustrated in FIG. 9, installation tool 60' may also include wing depressors and a vessel expander as discussed in connection with installation tool 60. Unlike installation tool 60, which includes only one guide 74 that is movable, guides 74' of installation tool 60' are both movable. That is, both of guides 74' may pivot or otherwise move relative to carrier 72' (e.g., relative to a stationary portion 76' of carrier 72').

In view of the disclosure herein, it will be appreciated that installation tool 60 is merely one example of a suitable installation tool, wing depressor, and/or vessel expander, and that other embodiments are contemplated. For instance, in the illustrated embodiment, the movement of vessel expander 62 and wing depressors 70 may be simultaneous or otherwise linked or correlated. In other embodiments, however, vessel expander 62 may be movable independent of wing depressors 70. In still other embodiments, an installation tool includes only a vessel expander, while a separate tool or manual handling is used to depress wings 18.

Figure 10:
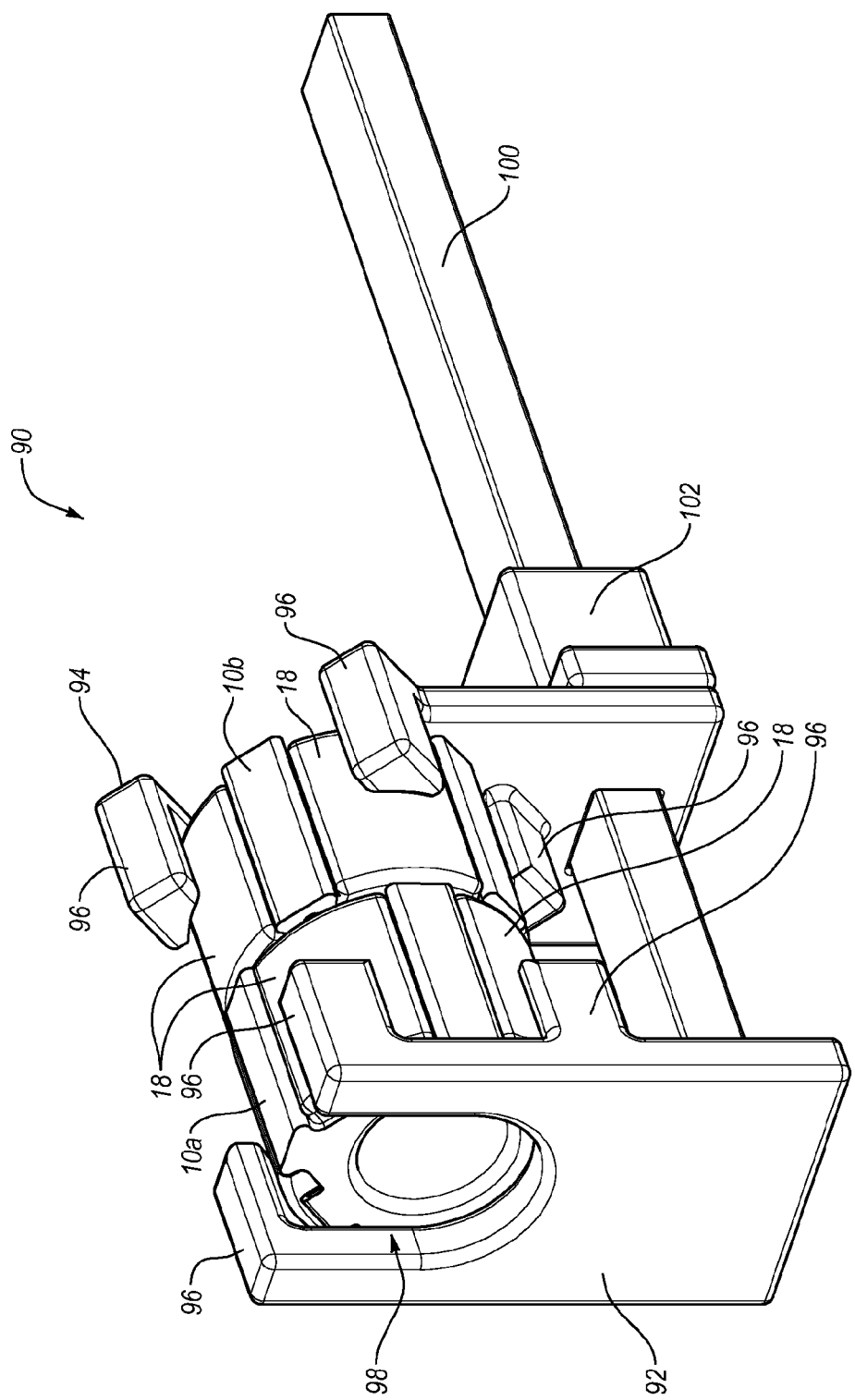
FIG. 10 illustrates an example clamping tool for clamping two coupling devices together and optionally aligning the devices, according to another example embodiment of the present disclosure.

Turning now to FIG. 10, another exemplary tool is illustrated. The illustrated clamping tool 90 may be used in connection with device 10 and/or other methods, apparatus, devices, processes, and treatments described or contemplated herein. In this embodiment, clamping tool 90 is described with reference to a manner of securing two coupling devices 10a, 10b together. Such a coupling may be used to, for example, perform an end-to-end vascular anastomosis on two cut or otherwise separated portions of a vessel.

Clamping tool 90 includes a set of coupling supports that may each engage a corresponding one of coupling devices 10a, 10b. For instance, in this embodiment, a first coupling support 92 may be configured to be coupled to first coupling device 10a, while a second coupling support 94 may be configured to be coupled to second coupling device 10b. First and second coupling supports 92, 94 may be configured for use with a number of different types of coupling devices. The particular embodiment shown in FIG. 10 includes four coupling braces 96 on each of first and second coupling supports 92, 94. Coupling braces 96 may be arranged to correspond to particular structures of coupling devices 10a, 10b. As an example, coupling braces 96 may each be spaced at approximately ninety degree angular intervals so as to engage depressed wings 18 of coupling devices 10a, 10b.

In the illustrated example embodiment, first coupling support 92 may be adapted to support first coupling device 10*a* in a deployed configuration. While in the deployed configuration, clamping tool 90 may also act to assist in coupling second coupling device 10*b* to first coupling device 10*a* and facilitate a connection or sealing of two ends of a vessel in an anastomosis procedure (e.g., end-to-end anastomosis). To more clearly illustrate aspects of clamping tool 90, the vessels being attached are not illustrated in FIG. 10; however, it will be appreciated in view of the disclosure herein that the ends of the vessel may be attached to each of coupling devices 10*a*, 10*b*. For instance, the vessels may be attached to coupling devices 10*a*, 10*b* and then extend through vessel opening 98 in each of first and second coupling supports 92, 94.

In the illustrated embodiment, first coupling support 92 is attached to a guide 100. First coupling support 92 may be fixed at one end of guide 100. In some embodiments, second coupling support 94 may also be attached to guide 100. As shown in the embodiment in FIG. 10, second coupling support 94 may be attached to guide 100 in a manner that allows second coupling support 94 to move along a longitudinal length of guide 100. For instance, a carrier 102 may be attached to second coupling support 94. Carrier 102 may also move along guide 100 and may act to facilitate handling of second coupling support 94.

With first and second coupling devices 10*a*, 10*b* each attached to or supported by respective coupling supports 92, 94, the movement of second coupling support 94 towards first coupling support 92 may draw first and second coupling devices 10*a*, 10*b* nearer to each other. Upon sufficient movement of second coupling support 94, first and second coupling devices 10*a*, 10*b* may become engaged and clamped together by a clamping force exerted on devices 10*a*, 10*b* by first and second coupling supports 92, 94. Clamping tool 90 may thus act to connect first and second coupling devices 10*a*, 10*b* and also couple together open edges of a vessel that are connected at an interface between first and second coupling devices 10*a*, 10*b*.

Clamping tool 90 may also act, in some embodiments, to align first and second coupling devices 10*a*, 10*b*. For instance, as discussed previously, an example embodiment of devices 10*a*, 10*b* may each include tissue engaging portions and receiving portions that may be alternately positioned (e.g. at varying axial and/or angular positions) around a central axis of devices 10*a*, 10*b*. In the illustrated embodiment, in which there are four wings 18, there may also be four tissue engaging portions on each of devices 10*a*, 10*b*, as well as four receiving portions. As illustrated in FIG. 10, coupling braces 96 of first coupling support 92 may be offset relative to coupling braces 96 of second coupling support 94. For instance, first and second coupling supports 92, 94 may have coupling braces 96 that are offset at about forty-five degrees. This offset may allow each coupling brace 96 to be placed on a particular wing 18 of a respective coupling device 10*a*, 10*b*. Coupling braces 96 may optionally be contoured to match a contour of wings 18, may fit within an outer surface of wings 18, or otherwise be configured to match to a particular location on coupling devices 10*a*, 10*b*. The forty-five degree offset may also help to facilitate alignment of receiving portions with tissue engaging portions. More particularly, each of the four tissue engaging portions on a coupling device 10*a*, 10*b* may be forty-five degrees from each of two receiving portions. Thus, by aligning a corresponding one of coupling devices 10*a*, 10*b* at a forty-five degree angle, the tissue engaging portions of first coupling device 10*a* may be aligned with the receiving portions of second coupling device 10*b*, and vice versa.

It will be appreciated in view of the disclosure herein that the clamping tool in FIG. 10 is merely one example of a suitable tool that can be used to clamp two coupling devices 10*a*, 10*b* together and/or to align two coupling devices 10*a*, 10*b* for installation in a vascular anastomosis, such as an end-to-end anastomosis. Other devices may also be used. For instance, while four coupling braces 96 are illustrated for each of first and second coupling supports 92, 94, there may be more or fewer coupling supports. For instance, in an embodiment in which wings 18 are locked in place, another clamping device may not include a coupling brace 96 at each of wings 18. In other embodiments, there may be more or fewer wings 18, so more or fewer coupling braces 96 may be used.

Furthermore, while only one of coupling supports 92, 94 is illustrated in FIG. 10 as movable relative to guide 100, this embodiment is merely exemplary. In some embodiments, two or more coupling supports 92, 94 may move. For instance, a ratchet device may move two coupling supports 92, 94 together. Further, while coupling braces 96 of the illustrated embodiment extend along an exterior surface of coupling devices 10*a*, 10*b*, they need not do so. For example, one or more openings may be placed on the distal faces of bodies 12 of coupling devices 10*a*, 10*b*. Coupling braces 96 may be replaced and/or supplemented with pins that then are inserted into such openings.

Accordingly, as described herein, multiple devices and apparatus are contemplated within the scope of the present disclosure for providing methods of performing a vascular anastomosis procedure. In some cases, the described devices and apparatus may be included within a kit. For instance, an exemplary kit may include a set of two or more coupling devices 10 packaged together. More than two coupling devices 10 may be included where, for example, multiple different sizes of coupling devices 10 may be used depending on the vessel to be coupled. In still other embodiments, the two or more coupling devices 10 may be packaged with a clamp, alignment device, wing depressor, and/or vessel expander. As described herein, one or more of the clamp, alignment device, wing depressor and vessel expander, or features thereof, may also be combined into one or more apparatuses, and need not be separate apparatuses. For example, first coupling support 92 and/or second coupling support 94 may be incorporated into an installment device as part of the carrier. By way of illustration, the coupling braces could also act as wing depressors.

Installation tool 60 and clamping tool 90, as well as other devices, apparatus, and tools need not, however, be included as part of a kit. For instance, in some embodiments, coupling devices 10 may be single-use devices whereas installation tool 60, clamping tool 90, other tools, or combinations thereof, may be reusable. Accordingly, installation tool 60 and/or clamping tool 90 may be made of medical grade stainless steel, aluminum, titanium, or other materials that are sufficiently robust to withstand sterilization procedures to allow for multiple uses.

Figure 11:
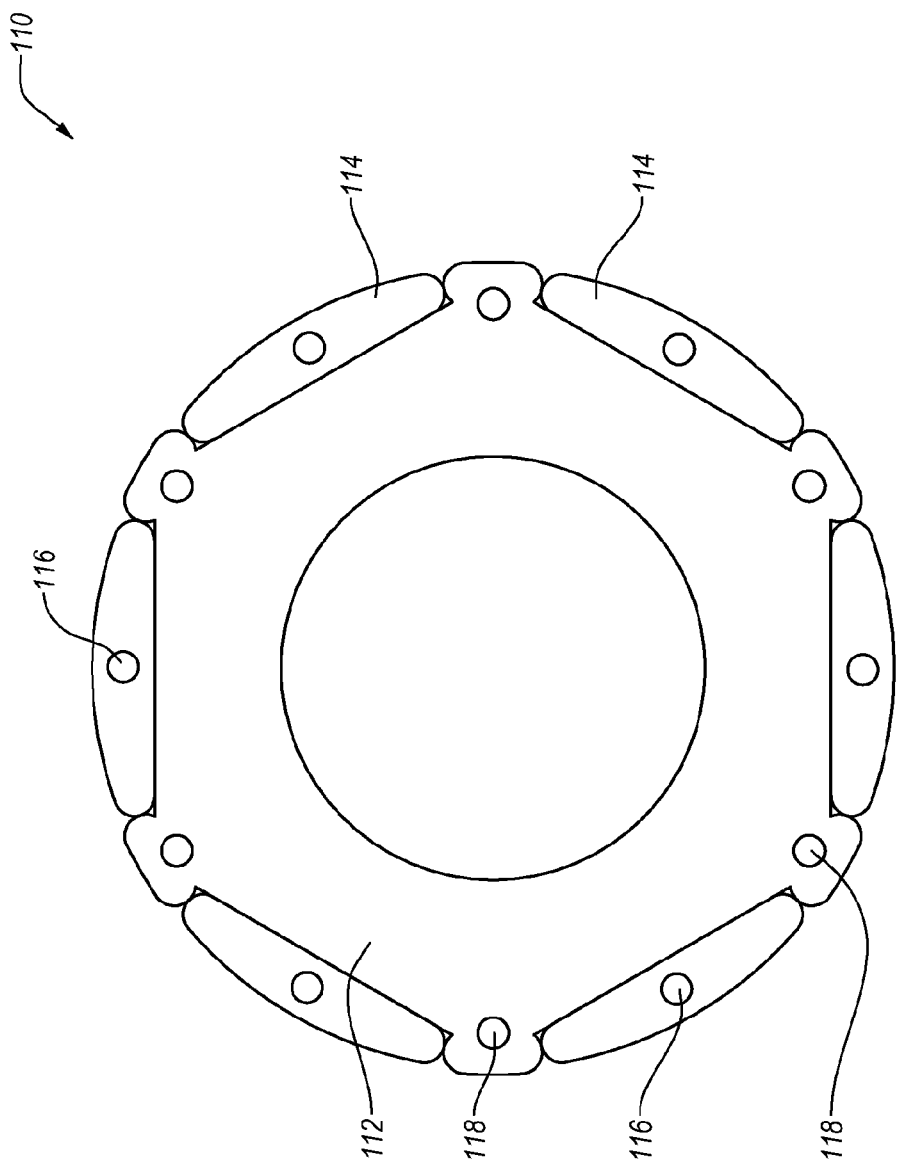
FIG. 11 is a frontal view of another example embodiment of a vascular coupling device.

As described herein, exemplary devices, apparatus, and tools for performing or facilitating a vascular anastomosis (e.g., end-to-end anastomosis) may be structured and/or configured in numerous different ways. The particular embodiments specifically illustrated and/or described should therefore not be used to limit the scope of the claims, particularly where various other alternatives are described herein and/or would be appreciated in view of the disclosure herein. For example, the exemplary coupling device 10 described relative to FIGS. 1-10 may be varied in a number of different manners. FIG. 11, for instance, illustrates an exemplary coupling device 110 having a body 112 and six wing portions 114. In the illustrated embodiment, body 112 acts as a hub around which six wing portions 114 are placed. The six wing portions 114 may, for instance, be about equally distributed around a central axis of body 112.

In the illustrated embodiment of coupling device 110, wing portions 114 are illustrated in a closed configuration; however, it will be appreciated in view of the disclosure herein that wing portions 114 may rotate or otherwise move relative to body 112. Moreover, the illustrated coupling device 110 can also include multiple tissue engaging members 116. One or more of tissue engaging members 116 may be attached to each of wing portions 114 and may be optionally movable relative to body 112. One or more attachment mechanisms 118 may also be disposed on, formed in, or otherwise located relative to body 112. In an example embodiment in which two coupling devices 110 may be mated together, for instance, each of coupling devices 110 may have six tissue engaging members 116. Accordingly, six attachment mechanisms 118 that take the form of openings in body 112 may be disposed on coupling device 110.

Attachment mechanisms 118—whether they take the form of holes or have other structure—may also be spaced relative to the central axis of body 112. In this embodiment, attachment mechanisms 118 and tissue engaging members 116 are about equally spaced in an alternating pattern around the center of body 112, although this is exemplary only. Further, while attachment mechanisms 118 and tissue engaging members 116 are shown to have approximately the same cross-sectional size, their respective shapes and/or sizes may different. For instance, attachment mechanisms 118 may comprise holes that have a smaller cross-sectional size than tissue engaging members 116 such that a lock fit or interference fit may be formed when a tissue engaging member 116 is placed within an attachment mechanism.

The use of six wing portions 114 is also exemplary. For instance, in other embodiments, between three and eight wing portions are used. Although not necessary, the wing portions may be about evenly spaced relative to a central axis of a coupling device, and/or may be spaced generally around a perimeter of the coupling device. In some cases, the angular spacing between the wing portions may be between about forty-five degrees and about one hundred twenty degrees. The angular spacing between a tissue engaging member and an adjacent attachment mechanism 118 may, in some embodiments, vary between approximately twenty-two and a half degrees and about sixty degrees.

Figure 12:
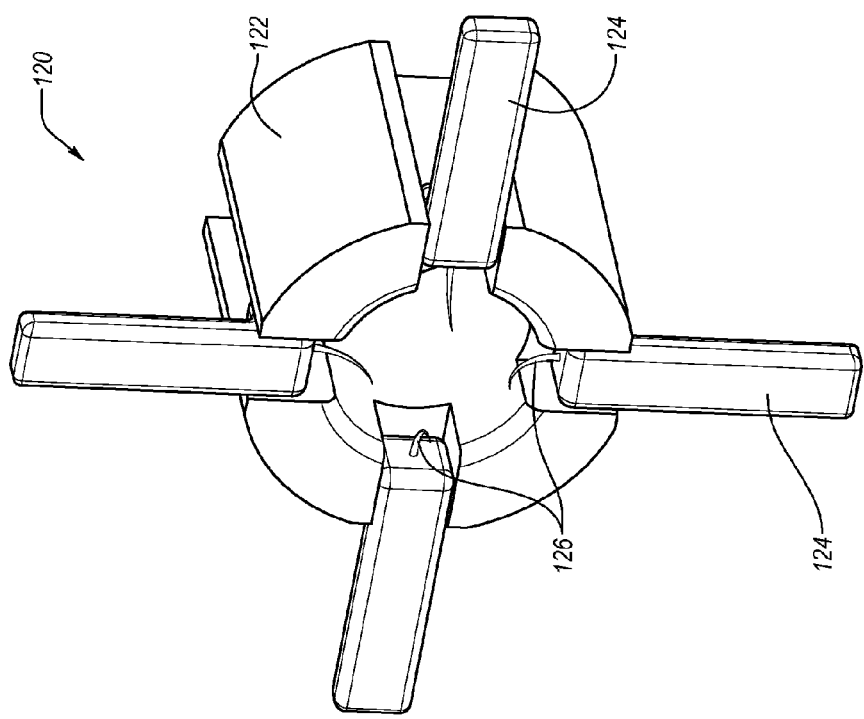

Turning now to FIG. 12, another example embodiment of a vascular coupling 120 is illustrated. In this embodiment a set of four wing portions 124 are disposed around a perimeter of a body 122 of coupling 120. Wing portions 124 may be hinged relative to body 122. For instance, in this embodiment a pivot rod or other hinge-type mechanism may be placed near the proximal end of body 122, although it need not be a living hinge, and also may not be directly at the proximal end of body 122.

Figure 13:
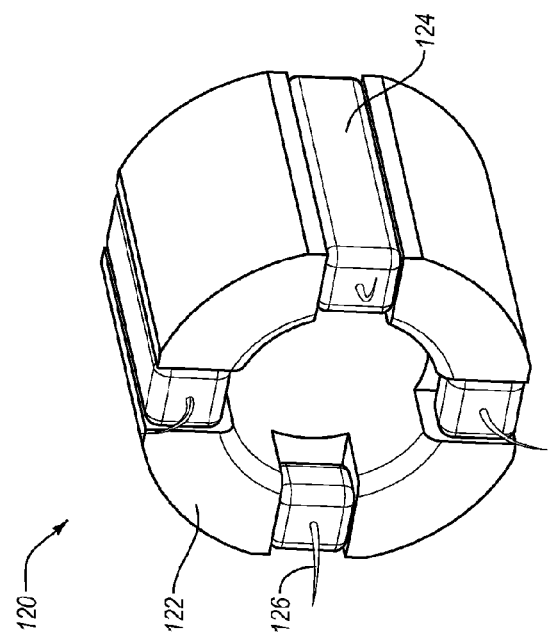
FIGS. 12 and 13 illustrate example pre-deployment and deployed configurations, respectively, of an example vascular coupling device.

In this embodiment wing portions 124 of coupling 120 may rotate between a pre-deployment configuration such as that illustrated in FIG. 12, and a deployed configuration such as that illustrated in FIG. 13. In the pre-deployment configuration, wing portions 124 may be approximately perpendicular to the lumen within body 122, whereas in the deployed configuration, wing portions 124 may be approximately parallel to the lumen within body 122. As best illustrated in FIG. 13, wing portions 124 may also nest within body 122 (e.g., within a wing receptor or channel). Wing portions 124 may nest partially within body 122, or fully within body 122, although in other embodiments there may be wing portions that are merely coupled to the body without a particular receptor or nesting area.

Coupling 120 may also include multiple tissue engaging members 126. As best shown in FIG. 13, for instance, a tissue engaging member 126 may be positioned at approximately the proximal ends of wing portions 124. As wing portions 124 move, tissue engaging members 126 may also move, and the distance between tissue engaging members 126 may change. FIG. 12, for instance, illustrates the various tissue engaging members 126 directed generally inward, and at a first distance from the central axis of body 122. FIG. 13 also illustrates tissue engaging members 126; however, tissue engaging members 126 have been moved and are directed generally outward, such that the distance between tissue engaging members 126 and the central axis of body 122 has increased.

Figure 14B:
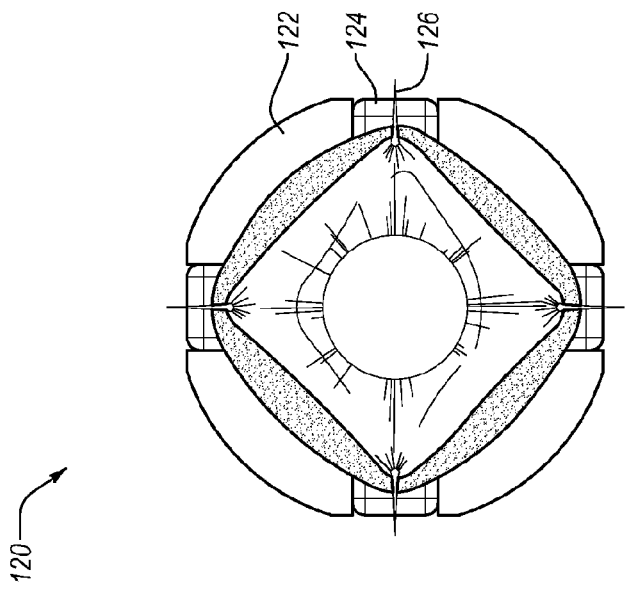
FIGS. 14A and 14B illustrate the vascular closure device of FIGS. 12 and 13 as coupled to, and expanding, tissue.
Figure 14A:
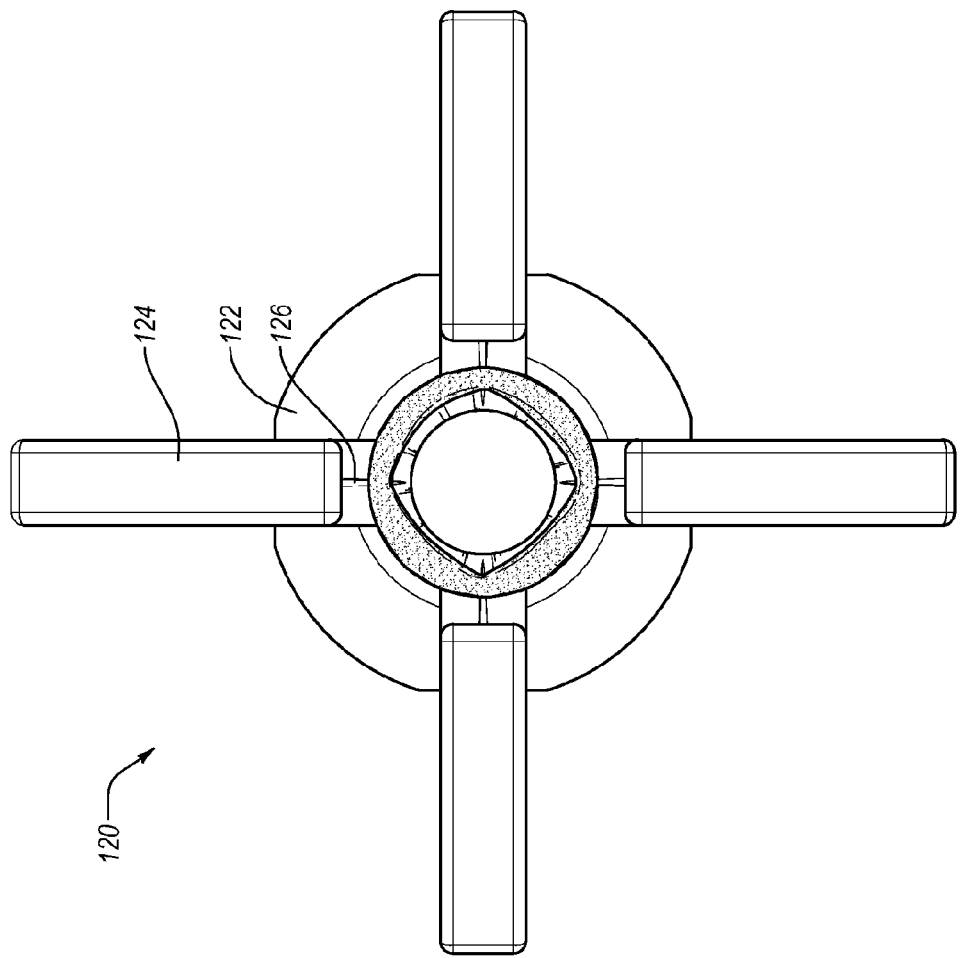

Tissue engaging members 126 in the illustrated embodiment are also shown to be generally hook shaped. For instance, in this embodiment, engaging members 126 have an L-shape, although other shapes such as a J-shape, C-shape, straight shape, other shapes, or combinations thereof may also be used. Such a hook shape may also be effectively used to engage tissue as described herein. For instance, FIGS. 14A and 14B illustrate an example coupling device mated with tissue. In the illustrated embodiment, tissue engaging members 126 penetrate the tissue walls and, when wing portions 124 are placed in a deployment configuration, the vessel wall may be stretched. As further illustrated in FIG. 14B, the stretching of the tissue by the movement of wing portions 124 and tissue engaging members 126 may evert the end of the tissue to expose the interior surface of the tissue, thereby facilitating intima-to-intima contact.

Figure 15:
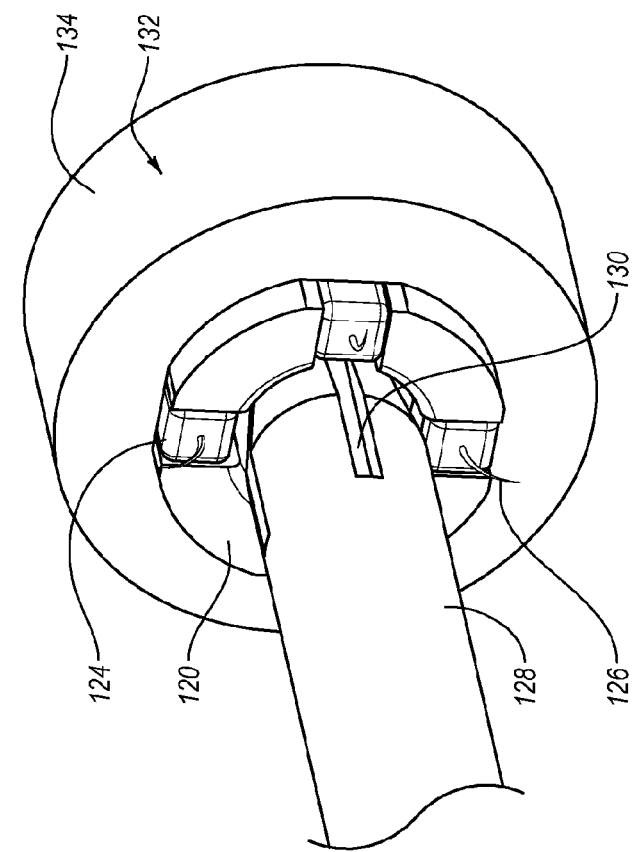
FIG. 15 illustrates an expander tool and locking ring for an example vascular coupling device.

Turning to FIG. 15, another example of a locking mechanism 132 is illustrated. In this embodiment, a locking ring 134 is disposed around coupling 120. When wing portions 124 of coupling 120 are in the deployed configuration, an interior surface of locking ring 134 may mate with an exterior surface of coupling 120, thereby substantially restricting movement of wing portions 124 and maintaining coupling 120 in the deployed configuration.

Also illustrated in FIG. 15 is an exemplary vessel expander tool 128 that may be used in connection with coupling 120. Vessel expander tool 128 may be inserted into an end of the vessel or other tissue attached to coupling 120. As vessel expander tool 128 is inserted, the outer surface of expander tool 128 may engage the interior surface of the vessel and cause it to expand radially outward. In some embodiments, expander tool 128 may have a generally conical and/or tapered nose to facilitate generally uniform expansion around the perimeter of the vessel. As expander tool 128 causes the vessel to expand, the vessel may engage against, and possibly be penetrated by, tissue engagement members 126.

In some embodiments, expander tool 128 may be flexible, although in other embodiments expander tool 128 may be substantially rigid. In still other embodiments, expander tool 128 may be configured to prevent or substantially reduce the likelihood of tissue engagement members 126 penetrating expander tool 128. For instance, as shown in FIG. 15, one or more channels 130 may be formed on the exterior surface and aligned with tissue engagement members 126. In such an embodiment, as expander tool 128 expands the vessel into engagement with the tissue engagement members 126, tissue engagement members 126 may press into channels 130 rather than into or against a surface of expander tool 128. In some embodiments, the outer surface of the expander tool may include one or more prongs, hooks, spikes, or other engagement features, or a combination thereof. Such features may, for example, engage a vessel wall to maintain the vessel at a particular location relative to the expander tool while the vessel is expanded.

Figure 17:
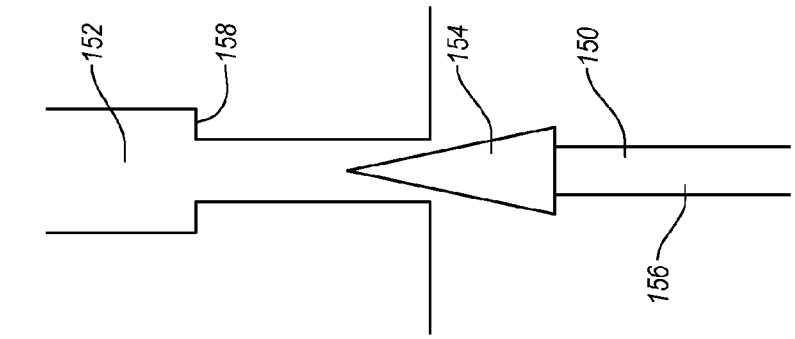
FIGS. 16-19 illustrate example tissue engaging members that may be used with a corresponding receiving portion of a mating coupling device.
Figure 16:
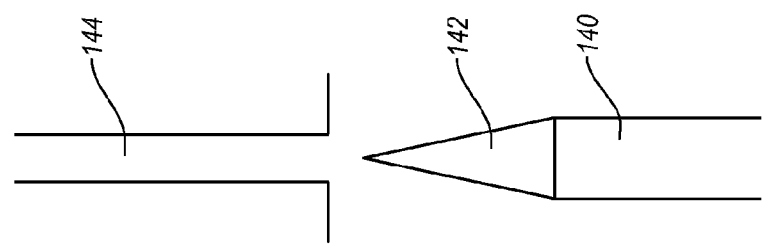
Figure 18:
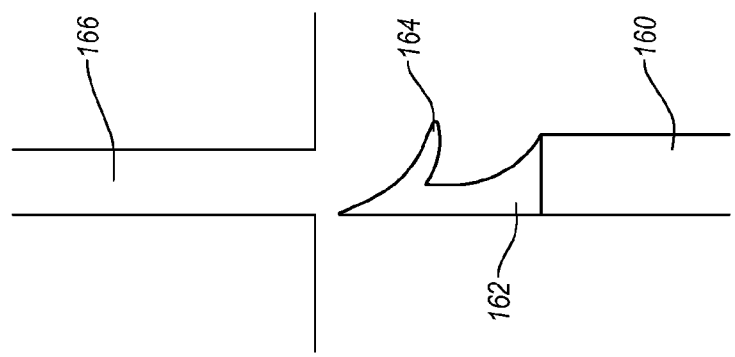

As discussed herein, one or more tissue engaging portions may be aligned with a receiving portion that includes an opening or hole. As the tissue engaging portions are received within the receiving portions, a tight fit between mating couplings may be obtained. In some embodiments, the fit between the mating couplings may facilitate sealing in a vascular anastomosis (e.g., end-to-end anastomosis). Turning now to FIGS. 16-18, various additional embodiments of mechanisms for connecting mating couplings are described. In FIG. 16, for instance, an example tissue engaging member 140 is illustrated, along with an example receiving portion 144. In this embodiment, tissue engaging member 140 includes a tip 142 that is inserted into receiving portion 144. Tip 142 in FIG. 16 has a size greater than at least a portion of receiving portion 144. As a result, when tip 142 is inserted into receiving portion 144, receiving portion 144 may deform. The continued insertion of tip 142 into receiving portion 144 may thereby create an interference fit that couples mating components together.

In a similar manner, FIG. 17 illustrates a tissue engaging member 150 that is aligned with, and can be inserted into, a corresponding receiving portion 152. Tissue engaging member 150 in this embodiment may have a tip 154 that rests on a shaft 156. Tip 154 may have a diameter that is greater than at least a portion of shaft 156. For example, in this embodiment, at the interface between tip 154 and shaft 156 the size of tip 154 is greater, thereby creating an engagement head. As tissue engaging member 150 is then inserted into receiving portion 152, tip 154 may engage against the walls defining receiving portion 152, and creating an interference fit. In some cases, the receiving portion may have multiple sizes. In FIG. 17, for instance, receiving portion 152 transitions from a narrow profile to a larger profile, thereby creating a shelf 158. As tip 154 of tissue engaging portion 150 is then inserted into receiving portion 152, tip 154 may enter the larger profile section. The larger end of tip 154 may then be positioned against or near shelf 158, thereby resisting movement that would tend to cause tip 154 to retract out of receiving portion 152.

In FIG. 18, a tip 162 of a tissue engaging portion 160 has a barb 164. Barb 164 may be formed in a manner that generally allows tissue engaging portion 160 to be inserted into a corresponding receiving portion 166. Barb 164 may engage the walls defining receiving portion 166 to create an interference fit. Further, if tissue engaging portion 160 is retracted—either voluntarily or involuntarily—barb 164 may engage the walls around receiving portion 166. As barb 164 engages the walls, barb 164 may limit or restrict the ability to withdraw tissue engaging portion 160 from receiving portion 166, thereby generally locking corresponding couplings in a desired position.

Figure 19:
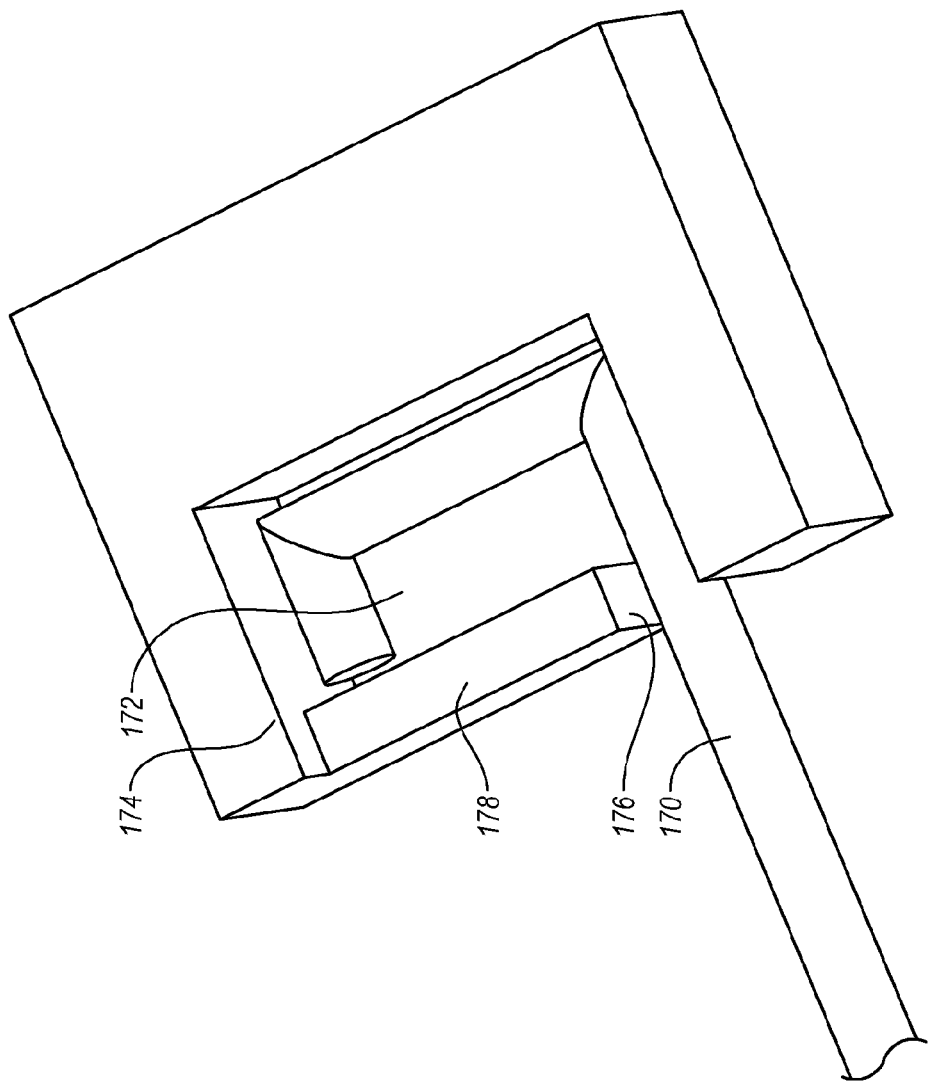

FIG. 19 illustrates yet another example embodiment of a structure that may be used to couple or lock two corresponding structures in a desired position. In this example embodiment, a tissue engaging portion 170 has a hook shape. Tissue engaging portion 170 may be inserted into a receiving portion 172 of a corresponding component. Receiving portion 172 may include, for example, a slot 174 sized to receive the hooked tissue engaging portion 170. In some embodiments, slot 174 is connected to a channel 176. Channel 176 may be sized to accept only a portion of tissue engaging portion 170. For instance, in the illustrated embodiment, the hook portion of tissue engaging portion 170 is maintained behind a wall 178 while a post portion can travel through channel 176. To move the post portion through channel 176, the mating couplings may be rotated or translated relative to each other. In any manner, channel 176 may facilitate moving tissue engaging portion 170 at least partially behind a wall 178 so as to prevent inadvertent disengagement of the mating couplings.

Figure 20A:
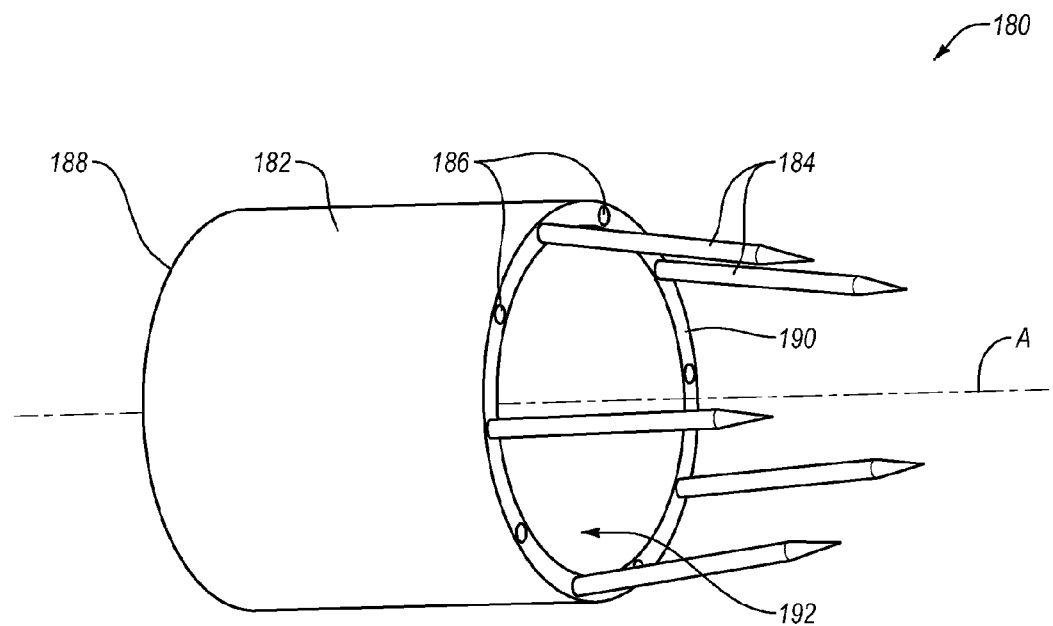
FIG. 20A illustrates a perspective view of an example vascular coupling device in a pre-installation state, according to one embodiment of the disclosure.
Figure 20B:
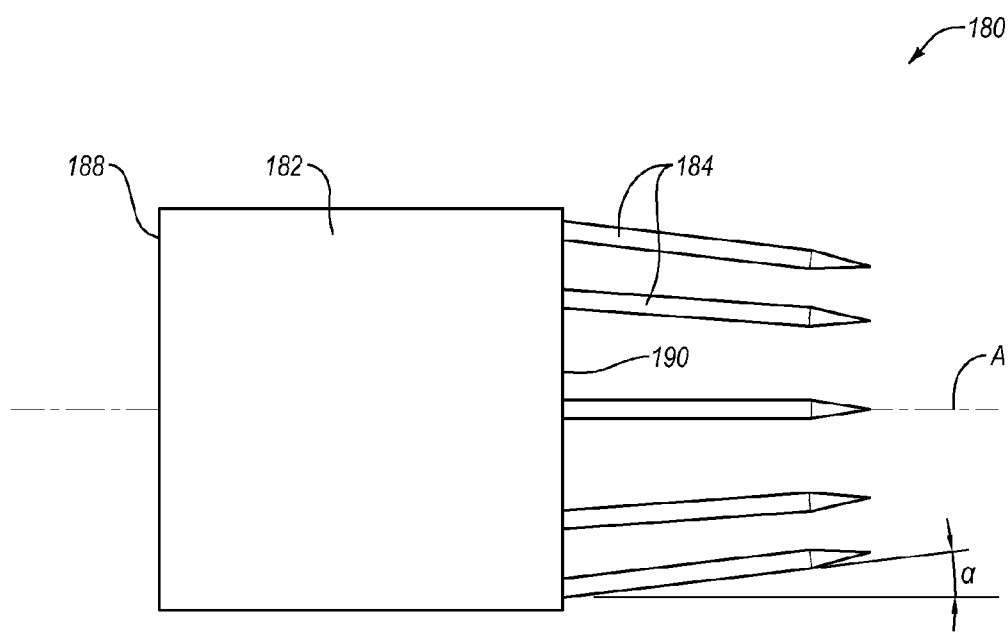
FIG. 20B illustrates a side view of the example vascular coupling device of FIG. 20A.

Turning now to FIGS. 20A and 20B, there are shown various views of an embodiment of a device 180 for use in performing an end-to-end anastomosis. Device 180 may be used for coupling or grafting ends of veins, arteries, tissue and other types of vessels or vasculature together, as well as with vasculature of different sizes. As shown in FIGS. 20A and 20B, device 180 may include a body 182. In the illustrated embodiment, body 182 may be generally annular in shape and/or may generally surround a lumen 192 centered on a central axis A.

Device 180 for performing an end-to-end anastomosis may in some embodiments include few or no moving parts. For instance, in FIGS. 20A and 20B, device 180 may not include linkages, hinges, rollers, bearings, or other components that facilitate movement relative to each other. In particular, as used herein, "moving parts" is considered to include components or elements that facilitate motion of one component relative to another. Accordingly, a component which may be bent is not considered a moving part for the description herein. Thus, it will be appreciated in view of the disclosure herein that a lack of moving parts need not require that device 180 be substantially rigid or immovable. For instance, in some embodiments, body 182 may be formed of a flexible material. By way of illustration, a plastic or other material that is pliable, or which may bend or flex while undergoing elastic or inelastic deformation. In other embodiments, body 182 may be a rigid or substantially rigid material.

Device 180 may also include, in some embodiments, a plurality of tissue engaging portions 184. Body 182 of the illustrated embodiment may include a distal end 188 and a proximal end 190. Tissue engaging portions 184 of this embodiment extend from proximal end 190 of body 182, although in other embodiments tissue engaging portions 184 may extend from additional or other locations. Tissue engaging portions 184 may have any suitable construction. For instance, in some embodiments, tissue engaging portions 184 include a tip. The tip may be sharp, barbed, or otherwise configured to engage and/or penetrate tissue. In other embodiments, tissue engaging portions 184 may be substantially blunt.

In the present embodiment, the tips of tissue engaging portions 184 may be sharp to facilitate engaging tissue. In some embodiments where the tip is sharp, the tip may not only engage tissue, but may also penetrate the tissue. For instance, if device 180 is used in connection with performance of an end-to-end anastomosis, and is used with an end of an artery or vein, the tips of tissue engaging portions 184 may fully penetrate through a side wall of the artery or vein, and into the lumen of the vessel, although in some embodiments, the tips may only partially penetrate the tissue.

As illustrated in FIGS. 20A and 20B, tissue engaging portions 184 can take the form of spikes that extend from the proximal end 190 of body 182. As illustrated, spiked tissue engaging portions 184 may be inclined rather than straight or parallel relative to longitudinal axis A. For instance, as best illustrated in FIG. 20B, one or even all of tissue engaging portions 184 may be inclined towards longitudinal axis A in some embodiments. More particularly, one or more of tissue engaging portions 184 may extend from a face of body 182 at proximal end 190. Rather than extending parallel to body 182, tissue engaging portions 184 can be angled inward, such that the tips of tissue engaging portions 184 may be at radial positions generally aligned with lumen 192 (FIG. 20A) defined by body 182.

The number, length, size, shape, angle, or other configuration of tissue engaging portions 184 may be varied. For instance, in one embodiment, the angle and length of tissue engaging portions 184 may be such that the tips of tissue engaging portions 184 are generally adjacent each other, or optionally touch, at about longitudinal axis A. In other embodiments, such as those illustrated in FIGS. 20A and 20B, tissue engaging portions 184 may not touch. In general, an exemplary angle of tissue engaging portion 184 is illustrated in FIG. 20B, and is depicted as angle α. Angle α can represent an angle of tissue engaging portion 184 relative to a line parallel to longitudinal axis A of body 182, or relative to another line. Angle α can vary. For instance, in some embodiments, angle α is between fifteen and sixty degrees; however, angle α may be more than sixty degrees or less than fifteen degrees. In some embodiments, the length of tissue engaging portions 184 is between about 50-100% the longitudinal length of body 182, although such configuration is merely exemplary as tissue engaging portions 184 may also be less than half the length of body 182, or longer than body 182.

Tissue engaging portions 184 may take any number of other forms. Tissue engaging portions 184 may instead have a curved, looped, L-shaped, or other configuration that may, for example, engage against and/or penetrate vascular tissue, a mating coupling device, or combinations thereof. Furthermore, one tissue engaging portion 184 may vary, for example, in size, shape, orientation, function, other characteristics, or combinations thereof, with respect to other tissue engaging portions 184 on the same device 180.

According to some embodiments of the present disclosure, device 180 may also include one or more receiving portions 186. Receiving portions 186 may be structured, arranged, and/or configured to receive all or a portion of a second component (such as device 180a or 180b shown in FIG. 22). For instance, a second component may be similar to device 180 and can include a plurality of tissue engaging portions, prongs, locks, or other devices. In the illustrated embodiment, receiving portions 186 include openings at proximal end 190 of body 182 and are approximately the same size as tissue engaging portions 184, slightly smaller than tissue engaging portions 184 (e.g., to facilitate an interference fit), slightly larger than tissue engaging portions 184, or otherwise configured. As described in more detail herein, similarly arranged tissue engaging portions of a second component may be configured to fit into receiving portions 186 and/or facilitate coupling between device 180 and a mating device or component. Receiving portions 186 may include openings that align device 180 and a second component, may act to interlock device 180 and the second component, provide any number of other functions, or combinations thereof. For instance, in one embodiment, receiving portions 186 may have a diameter slightly less than the diameter of the tissue engaging portions of a mating component, such that an interference fit may occur when the tissue engaging portions are positioned within receiving portions 186. In some embodiments, the interior or other walls of receiving portions 186 may be engaged by a barb or tip of the tissue engaging portions of a corresponding second component to secure device 180 to the mating component.

While a mating component may thus be similar or about identical to device 180, other embodiments are contemplated in which a mating device is significantly different with respect to device 180. For instance, device 180 as described herein may be used in connection with an end-to-end anastomosis procedure in which two ends of an artery, vein, tissue, or other vessel are coupled together. In such a case, a mating device similar to device 180 may be used. It need not be so, however, as a different type, style, configuration, or combination thereof may be used. In another embodiment, device 180 may be used in other types of anastomosis procedures, including a side-to-end anastomosis procedure. One skilled in the art in view of the disclosure herein can appreciate that a mating device may include a side wall of a mating vessel and/or a mating coupling device that facilitates side-to-end anastomosis in lieu of end-to-end anastomosis.

Figure 21A:
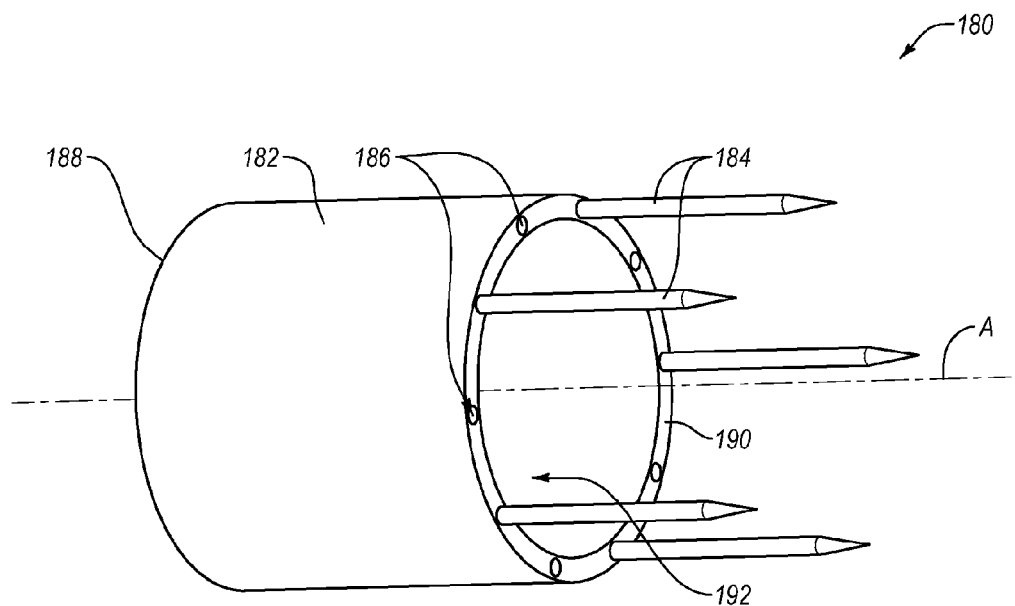
FIG. 21A illustrates a perspective view of the example vascular coupling device of FIG. 20A, when transitioned to an installation state, according to one embodiment of the disclosure.
Figure 21B:
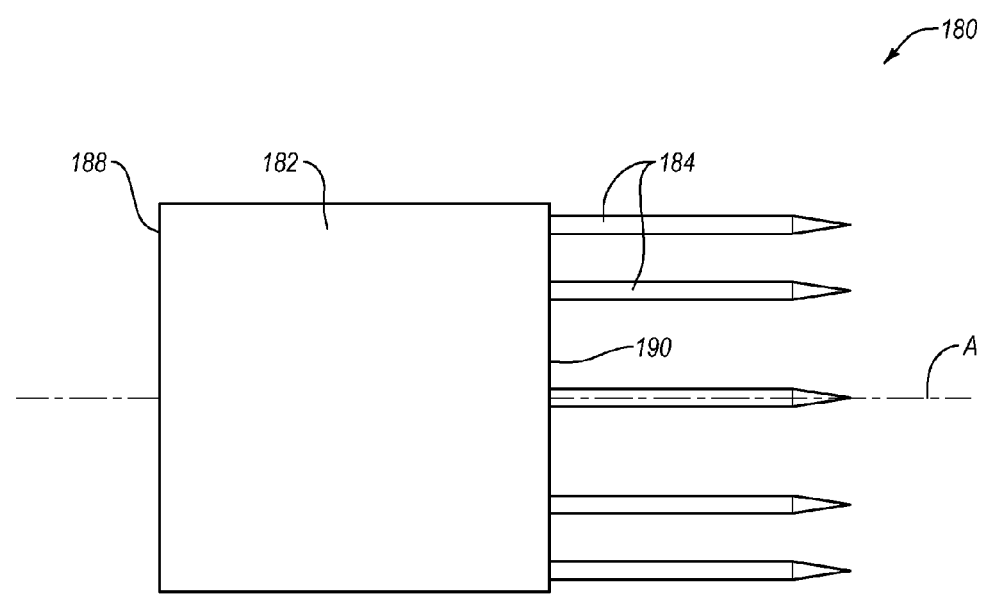
FIG. 21B illustrates a side view of the example vascular coupling device of FIG. 20A.

FIGS. 20A and 20B depict device 180 in an arrangement that may correspond to a relaxed, or pre-installation configuration. In the present embodiment, when device 180 is in a relaxed or pre-installation configuration, tissue engaging portions 184 may be directed radially inward (e.g., towards central axis A). Device 180 may also be deformable, or otherwise configured so as to allow the position of body 182 and/or tissue engaging portions 184 to move into an installation or other state. As shown in FIGS. 21A and 21B, for instance, device 180 can be placed in an installation configuration in which tissue engaging portions 184 are deflected. When deflected, tissue engaging portions 184 may have an angle thereof modified such that angle α (FIG. 20B) is modified. In some cases, angle α may equal about zero and tissue engaging portions 184 may be about parallel to longitudinal axis A.

When tissue engaging portions 184 are deflected, such as shown in FIGS. 21A and 21B relative to FIGS. 20A and 20B, the deflection may be generally permanent, or may be temporary. For instance, deflection of tissue engaging portions 184 may be performed by bending, stretching, or otherwise modifying tissue engaging portions 184 such that they undergo plastic or inelastic deformation. As a result, release of tissue engaging portions 184 during deformation may not result in tissue engaging portions 184 automatically reverting back to a pre-installation configuration, but rather tissue engaging portions 184 being self-sustaining at the installation configuration. In one embodiment, tissue engaging portions 184 may be formed of a metal material that is bent such that tissue engaging portions 184 remain about parallel to longitudinal axis A, or otherwise remain at an angle relative to longitudinal axis A that is different than angle α as described and illustrated relative to FIGS. 20A and 20B.

In some embodiments, device 180 may be selectively placed in an installation or deployed configuration, such as that illustrated in FIGS. 21A and 21B. Such a configuration may be used to, for instance, grip or maintain a vessel in an everted or other configuration used during attachment to another vessel. In some cases, moving device 180 between the pre-installation and the installation configurations may also cause a vessel to evert or to otherwise become secured relative to device 180. While device 180 is described above as being deformed to remain in the installation configuration, according to some embodiments, device 180 may be maintained in the installation or deployed configuration permanently or for only a period of time.

An external or internal force may be applied to cause device 180 to transition to, or remain at, the installation configuration. Exemplary methods and/or devices for such transformation are described hereafter with reference to FIGS. 24A-24C and FIGS. 25A-25D; however, any other suitable device may be used to cause device 180 to selectively change from or between a pre-installation configuration to an installation configuration. It should further be appreciated in view of the disclosure herein that the embodiments illustrated in FIGS. 20A-21B are merely exemplary and that other embodiments are contemplated as being within the scope of this disclosure. Accordingly, other coupling devices may be within the scope of the present disclosure despite lacking one or more of the elements illustrated in, and described relative to, FIGS. 20A-21B.

For example, while the illustrated embodiment generally depicts device 180 as having a body 182 formed as an integral, single-material construction, this is merely exemplary. In other embodiments, for instance, body 182 may be formed of multiple different segments or materials. By way of illustration, body 182 may be molded as two separate pieces and then such pieces may be thermally bonded or otherwise connected. Further still, while body 182 is shown as being substantially cylindrical, body 182 may have other shapes or features. For instance, one or more grooves may be formed on body 182. As an example, a groove or protrusion may be formed on the proximal face of body 182, and configured to mate with a corresponding protrusion or groove of an adjoining device.

Furthermore, while tissue engaging portions 184 are illustrated in FIGS. 20A-21B as spikes having a generally straight construction, the shape of tissue engaging portions 184 may be varied in a number of different manners. For instance, in one embodiment, tissue engaging portions 184 may be shaped like hooks and can have a generally L-shaped, J-shaped, C-shaped construction, otherwise shaped construction, or combinations thereof. In still other embodiments, tissue engaging portions 184 may be curved, spiral, angled, other otherwise constructed, or combinations thereof. The position and/or number of tissue engaging portions 184 may similarly be varied. Thus, while five tissue engaging portions 184 are illustrated at generally equal angular intervals, there may be more or fewer tissue engaging portions 184, and the angular offset between tissue engaging portions 184 may be the same or different relative to other tissue engaging portions 184. In another embodiment, there may be between three and eight tissue engaging portions.

The tip of the tissue engaging portions 184 may also be constructed in a number of different manners. In the embodiment illustrated in FIGS. 20A-21B, for instance, the tip has a generally conical construction and comes to a proximal point. In other embodiments, one or more tips may be blunt, rounded, barbed, fluted, otherwise arranged, or combinations thereof. For instance, the tip may have a barb or head portion that is configured to penetrate tissue and/or secure the tissue against tissue engaging portion 184. In still other embodiments, a barb, head, other securement mechanism, or combination thereof may be used to engage against a component that cooperates with device 180 in performing an anastomosis procedure, and to facilitate securement of the other component to device 180.

Further still, tissue engaging portions 184 may be formed in any suitable manner. For instance, in one embodiment, tissue engaging portions 184 are formed integrally with body 182. In another embodiment, tissue engaging portions 184 may be formed separately and attached or secured to body 182. For instance, one or more openings (e.g., similar or identical to receiving portions 186 may be formed in the proximal face 190 of body 182. Elongated tissue engaging portions 184 may be positioned within the openings and extend into body 182 up to a pre-determined distance. Thus, deforming or deflecting tissue engaging portions 184 may, in some embodiments, include deflecting or deforming a portion of tissue engaging portion 184 that is external to body 182, while a portion inside body 182 is relatively unaltered.

The described embodiments of device 180 for facilitating an end-to-end or other vascular anastomosis may be manufactured using various manufacturing processes. In the embodiment illustrated in FIGS. 20A-21B, for instance, a micro-manufacturing process may shape body 182 and/or tissue engaging portions 184 out of one or more biocompatible materials. For instance, exemplary biocompatible materials may include organic materials, metals, alloys, polymers, composites, and combinations thereof. According to one example, body 182 may be made from a biocompatible material such as silicone or high density polyethylene (HDPE). In other embodiments, tissue engaging portions 184 are formed of biocompatible materials such as titanium, cobalt, platinum, nickel, stainless steel, other materials, alloys thereof, or combinations of the foregoing.

Body 182 and/or tissue engaging portions 184 may be designed to remain in the body indefinitely, or may degrade over time. For instance, body 182 and/or tissue engaging portions 184 may be formed of a biodegradable, bioerodable, bioresorbable, or other degrading or resorbing material or combinations thereof. Examples of such materials that may be suitable for the manufacture of all or portions of device 180 may include copolymers, such as a copolymer of L-lactic acid and glycolic acid.

In one embodiment, tissue engaging portions 184 may be formed from a polymer or a stainless steel alloy; however, in other embodiments, the tissue engaging portions may be formed from titanium, nickel, nickel-titanium alloy (e.g., NITINOL®), cobalt, chromium, platinum, or other materials, or combinations thereof. In some embodiments, tissue engaging portions 184 are formed of NITINOL® or another shape-memory material. For instance, the pre-installation and/or the installation configurations of tissue engaging portions 184 may correspond to positions within the "memory" of tissue engaging portions 184. In some embodiments, the interior walls defining lumen 192 may be coated with a friction reducing material that allows vasculature to easily slide therein.

Device 180 may also, in some embodiments be configured to deliver drugs or beneficial agents to the vessel, a site proximate the vessel, another location, or combinations thereof. For instance, therapeutic agents, pharmaceuticals and/or radiation therapies may be provided or facilitated by device 180. Device 180 and/or a coating material may contain a beneficial agent, drug, or other agent that may improve the use of device 180, the success rate of a procedure in which device 180 is used, other health or other aspects of a patient, or combinations thereof. Any number of different types of drugs, beneficial agents, balms, or other elements or components, or combinations thereof may have delivery facilitated by device 180. Examples may include antiallergic substances, antiarrhythmics, antibiotics, anticoagulants, antifibrins, anti-inflammatories, antimitotics, antineoplastics, antioxidants, antiplatelet agents, antiproliferatives, antisense agents, antithrombotics, cell adhesion inhibitors, cell permutation enhancers, endothelial cell recovery promoting agents, gene-based agents, growth factor inhibitors, hemostatic agents, hyperplasia inhibitors, oligonucleotides, radiopaque agents, smooth muscle proliferation inhibitors, thrombolytics, and combinations thereof.

The size of devices 180 described herein may also be varied. For instance, in one embodiment, the devices may be sized to accommodate arteries, veins, tissue, or other vessels in the range of about one millimeter to about four millimeters. The vessels may, however, be larger or smaller. For instance, the embodiments described herein can also accommodate vessels larger than four millimeters (e.g., between about four millimeters to about twenty millimeters).

Reference will now be made to an exemplary method for using vascular coupling devices, such as device 180 of FIGS. 20A-21B, in performing an end-to-end vascular anastomosis, according to one embodiment of this disclosure. The described method is generally illustrated and described with respect to FIGS. 22 and 23; however, it will be appreciated that other methods and/or devices may be used in accordance with embodiments of this disclosure. As discussed above, embodiments of the present disclosure may also be used in end-to-side anastomosis procedures, and/or other procedures.

Figure 22:
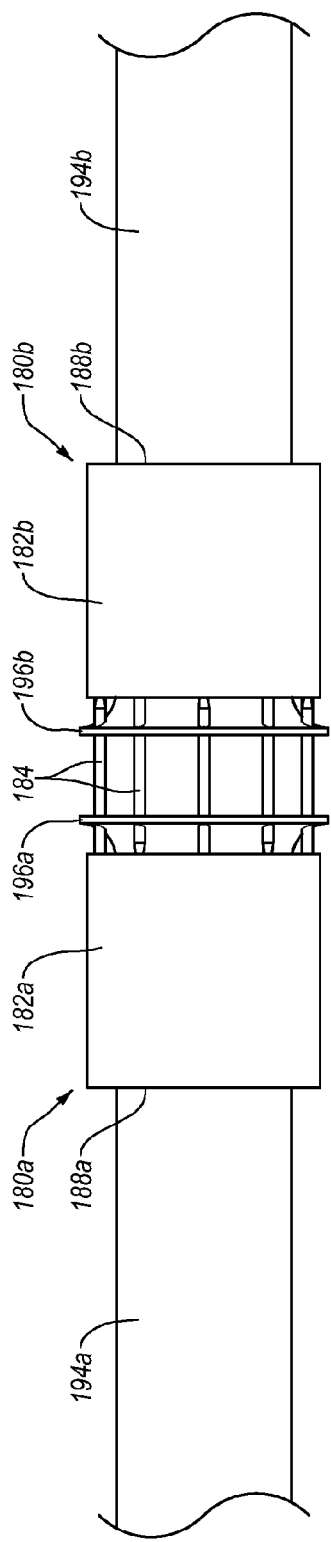
FIG. 22 illustrates a side view of a pair of vascular coupling devices when used in performing an end-to-end anastomosis procedure.

As shown in FIG. 22, a vessel has been cut or otherwise separated into two vessel portions 194a, 194b. In other embodiments, portions 194a, 194b correspond to separate portions of a graft. According to one method for performing an end-to-end vascular anastomosis, proximal ends 196a, 196b of each of the two vessel portions 194a, 194b are each associated with a corresponding one of devices 180a, 180b. For instance, in the illustrated embodiment, first vessel portion 194a is associated with first device 180a. First vessel portion 194a may be a blood vessel such as a vein or an artery, although the method is not so limited, and may be used in connection with other body vessels and/or organs.

In FIG. 22, first vessel portion 194a has been associated with first device 180a by passing the proximal end 196a of first vessel portion 194a through a lumen extending within body 182a and from distal end 188a of body 182a of first device 180a. In some embodiments, the size of the lumen may correspond generally to the size of first vessel portion 194a. For instance, prior to inserting first vessel portion 194a through the lumen, calipers, a measuring gage, or another measuring device may be used to determine an approximate diameter or other size of first vessel 194a. For instance, a surgeon or other person participating in the vascular anastomosis treatment may select a device 180a that has a lumen diameter approximately matching the external diameter of first vessel portion 194a. Device 180a may be available in a number of different sizes, and optionally may be color coded so that a particular color of a device or packaging corresponds to a particular size of the lumen therein. Accordingly, within the described method, a measurement of first vessel portion 194a and a selection of a particular size of device 180a may be performed.

As first vessel portion 194a is positioned within the lumen of device 180a, first vessel portion 194a may be inserted at distal end 188a and moved towards the proximal end of body 182. As first vessel portion 194a moves in a proximal direction, the free end of first vessel portion 194a may pass fully through body 182a. In passing first vessel portion 194a through body 182a in this manner, first vessel portion 194a may engage against one or more of tissue engaging portions 184. In the illustrated embodiment, for instance, tissue engaging portions 184 may be spikes that extend in a proximal direction from corresponding proximal ends of bodies 182. Tissue engaging portions 184 are illustrated in FIG. 22 as being generally parallel to a longitudinal length of bodies 182; however, it will be appreciated in view of the disclosure herein that tissue engaging portions 184 may have been initially positioned in an angled or other configuration prior to placement in the illustrated configuration. For instance, tissue engaging portions 184 may have been in pre-installation configurations and moved to an installation configuration such as that illustrated in FIG. 22. Moreover, in some embodiments, transitioning of tissue engaging portions 184 to the installation configuration may cause tissue engaging portions 184 to penetrate or otherwise engage vessels 194a, 194b, and optionally to evert proximal ends 196a, 196b thereof.

Accordingly, one aspect of tissue engaging portions 184 is that they may be adapted to engage the walls of first and/or second vessel portions 194a, 194b, and optionally pass fully or partially through a wall thickness of first and/or second vessel portions 194a, 194b. In FIG. 22, for instance, tissue engaging portions 184 may pass through the full wall thickness and enter into the interior of first vessel portion 194a, although in other embodiments tissue engaging portions 184 may pass only partially through the wall thickness.

Tissue engaging portions 184 may be caused to engage and optionally penetrate the wall of first vessel portion 194a in any suitable manner. In one embodiment, for instance, and as described hereafter, vessel 194a may pass through the lumen of body 182a while in a flaccid state. Vessel 194a may then be expanded (e.g., using an expander) and during expansion caused to engage tissue engaging portions 184 so as to allow tissue engaging portions 184 to fully or partially penetrate the walls of vessel 194a. After or during engagement, tissue engaging portions 184 can be deformed, deflected, or otherwise moved. For instance, tissue engaging portions 184 can be bent or moved outward, and away from the central axis of body 182a. As tissue engaging portions 184 move radially outward, tips of tissue engaging portions 184 may also move radially outward such that the distance between the tips increases. Such motion, coupled with engagement of vessel 194a, can cause proximal end 196a of vessel portion 194a to expand radially outward, which optionally everts proximal end 196a.

Regardless of the manner in which first vessel portion 194a is caused to be engaged with tissue engaging portions 184, first device 180a and first vessel portion 194a may become engaged in a manner similar to that illustrated in FIG. 22. For simplicity, the particular manner in which second vessel portion 194b is engaged with second device 180b is not described; however, it will be appreciated that devices 180a, 180b may operate in similar manners.

As shown in FIG. 22, first and second devices 180a, 180b may continue to be engaged or otherwise connected with two vessel portions 194a, 194b. For instance, the tips or other portions of tissue engaging portions 184 may have penetrated at least a portion of first vessel portion 194a. In the illustrated embodiment, for instance, tissue engaging portions 184 have each penetrated the exterior wall of first vessel portion 194a. Tissue engaging portions 184 may further grip or otherwise maintain such engagement and/or penetration with the first vessel portion as tissue engaging portions 184 are moved, or as first and second devices 180a, 180b are drawn together.

As described above, device 180a can optionally include receiving portions. Such receiving portions may include openings or holes angularly spaced around device 180a. In accordance with one embodiment, tissue penetrating portions 184 and the receiving portions may be alternately spaced around the central axis of body 182a. A mating second device 180b may be connected to a second vessel portion 194b in a manner similar to that described for first device 180a and first vessel portion 194a. Second device 180b may be rotated relative to first device 180a, such that tissue engaging portions 184 of second device 180b are generally aligned with receiving portions of first device 180a. Corresponding alignment between tissue engaging portions 184 of first device 180a may also be made with receiving portions of second device 180b.

The receiving portions may be holes, and may have a generally circular cross-sectional shape along all or a portion of the length thereof. The receiving portions may, however, have any number of other configurations, sizes, shapes, other features, or combinations thereof. For instance, a receiving portion may be a slot, a male or female connector, a twist lock feature, some other feature, or a combination thereof. Further, one or more of the receiving portions may have a shape, size, configuration, other feature, or any combination thereof that varies with respect to other receiving portions on the same device 180a, 180b.

When corresponding tissue engaging portions 184 and receiving portions are aligned, first and second devices 180a, 180b may be drawn together as shown in FIG. 22. As first and second devices 180a, 180b move towards each other, tissue engaging portions 184 may enter the receiving portions. Further advancement of first and second devices 180a, 180b towards each other may also cause the exposed proximal ends 196a, 196b of first and second vessel portions 194a, 194b to engage. More particularly, in some embodiments, interior surfaces of first and second vessel portions 194a, 194b may have been exposed at the respective free proximal ends 196a, 196b thereof. Consequently, when ends 196a, 196b are drawn into contact, an intima-to-intima contact may be formed, which may achieve a substantially tight seal at the interface between first and second vessel portions 194a, 194b.

As discussed herein, first and second devices 180a, 180b may be maintained in their deployed and coupled state for an indefinite period of time to facilitate sealing between first and second vessel portions 194a, 194b, and/or to effectively couple first and second vessel portions 194a, 194b in an end-to-end vascular anastomosis. For instance, tissue engaging portions 184 may form an interference fit with corresponding receiving portions such that first and second devices 180a, 180b are maintained in the coupled state.

While the illustrated embodiment generally illustrates substantially identical first and second devices 180a, 180b, it should be appreciated that this is merely one example in which devices and methods of the present disclosure may be used. For example, in other embodiments, first and second devices 180a, 180b may have different sizes, be differently shaped, have varying configurations, or a combination thereof. By way of illustration, it is not necessary that the end-to-end anastomosis be performed by coupling first and second vessel portions 194a, 194b of the same size. One vessel portion may be of a smaller size than the other, such that the interior lumen of one of devices 180a, 180b may be a different size than that of the other of devices 180a, 180b. In other embodiments, an end-to-side anastomosis may be performed.

In still other embodiments, devices 180a, 180b may have other coupling mechanisms. For instance, the devices may facilitate a male/female connection, with one of the devices having a male connector and the other device including a female connector. In other embodiments, the tissue engaging portions may have a different configuration. For instance, the tissue engaging portions may include a hook. The hook may in turn be received within a receiving slot in a mating device. Upon thereafter advancing (e.g., rotating) the coupling devices relative to each other, the hook may travel within a channel connected to the device, such that the two mating couplers are securely attached to each other in a manner that facilitates sealing between the two ends of the joined vessel.

The devices and apparatus described herein may be used in isolation but may also be used in connection with one or more other devices and/or apparatus. For instance, in some embodiments, an expander is used to expand the vessel and/or to facilitate engagement of the vessel by corresponding tissue engaging portions. In other instances, a clamp device may be used to align two coupling devices and/or facilitate engagement of mating coupling devices in an anastomosis treatment. In still other embodiments, coupling devices, expanders, clamp devices, or a combination thereof may be provided together as a kit.

Figure 23:
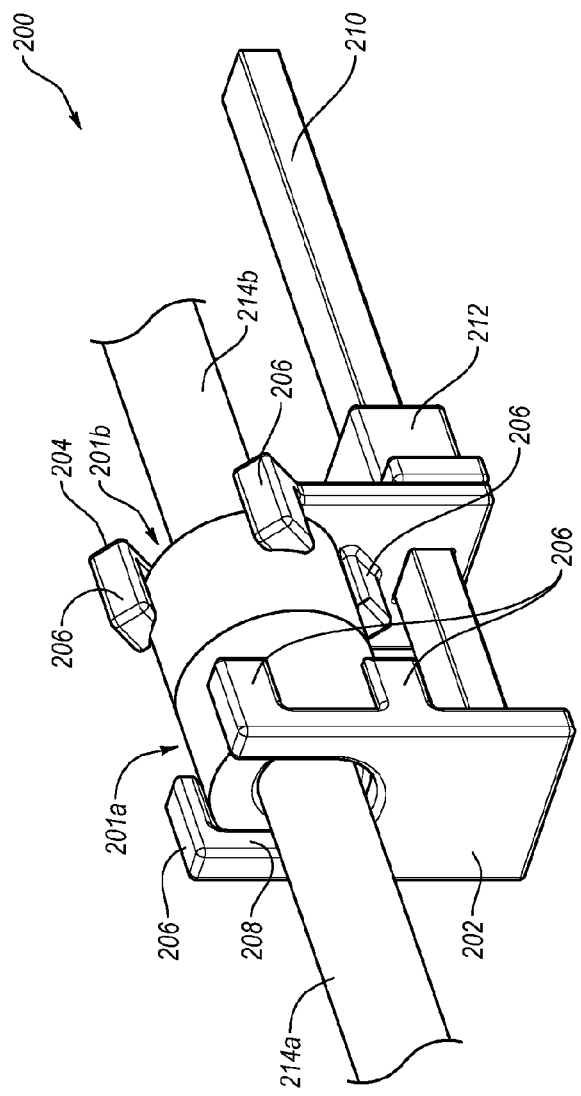
FIG. 23 illustrates a perspective view of a clamping device that may be used to facilitate connecting of two vascular coupling devices in an end-to-end anastomosis procedure according to one embodiment of the disclosure.

For instance, FIG. 23 illustrates an exemplary clamping tool usable in connection with some aspects of the present disclosure. More particularly, the illustrated clamping tool 200 may be used in connection with device 180 described above, or in connection with devices 201a, 201b illustrated in FIG. 23, which devices may be the same as or different than device 180. In still other embodiments, clamping tool 200 may be used in connection with methods, apparatus, devices, processes, and treatments described or contemplated herein. In this embodiment, clamping tool 200 is described with reference to a manner of securing two coupling devices 201a, 201b together. Such a coupling may be used to, for example, perform an end-to-end vascular anastomosis on two cut or otherwise separated portions of a vessel.

Clamping tool 200 includes a set of coupling supports that may each engage a corresponding one of the coupling devices 201a, 201b. For instance, in this embodiment, a first coupling support 202 may be configured to be coupled to a first coupling device 201a, while a second coupling support 204 may be configured to be coupled to a second coupling device 201b. First and second coupling supports 202, 204 may be configured for use with a number of different types of coupling devices. In the particular embodiment in FIG. 23, each of the first and second coupling supports includes four coupling braces 206 on respective interior ends thereof. Coupling braces 206 may be arranged to facilitate securely holding or maintaining devices 201a, 201b within tool 200 while devices 201a, 201b are mated together.

In the illustrated embodiment, braces 206 of first support 202 are illustrated at about a ninety degree angular interval with respect to braces 206 of second support 204. It should be appreciated that such configuration is merely exemplary. In other embodiments, for instance, braces 206 may be aligned between supports 202, 204. In still other embodiments, braces 206 of respective supports 202, 204 may be offset by other than ninety degree angles. For instance, where devices 201a, 201b each include five tissue engagement portions and five receiving portions, the offset between a tissue engaging portion and receiving portion may be about thirty six degrees. Braces 206 of respective supports 202, 204 may be offset in a manner that facilitates alignment of the tissue engagement portions of first device 201a with corresponding receiving portions of second device 201b, and vice versa. Of course, more or fewer than five tissue engagement structures and/or receiving portions may be included on devices 201a, 201b.

In the illustrated example embodiment, first coupling support 202 may be adapted to support first coupling device 201a in a deployed or installation configuration. While in the installation configuration, clamping tool 200 may also act to assist in coupling second coupling device 201b to first coupling device 201a and/or facilitate a connection or sealing of two portions 214a, 214b of a vessel in an anastomosis procedure (e.g., end-to-end anastomosis). For instance, vessels 214a, 214b may be attached to coupling devices 201a, 201b and then extend through vessel opening 208 in each of first and second coupling supports 202, 204.

In the illustrated embodiment, first coupling support 202 is attached to a guide 210. First coupling support 202 is optionally at a fixed position at one end of guide 210. In some embodiments second coupling support 204 may also be attached to guide 210. As shown in the embodiment in FIG. 23, second coupling support 204 may be attached to guide 210 in a manner that allows second coupling support 204 to move along a longitudinal length of guide 210. For instance, a carriage 212 may be attached to second coupling support 204. Carriage 212 may also move along guide 210 and may facilitate handling of second coupling support 204.

With first and second coupling devices 201a, 201b each attached to respective coupling supports 202, 204, the movement of second coupling support 204 towards first coupling support 202 may draw first and second coupling devices 201a, 201b nearer to each other. Upon sufficient movement of second coupling support 204, first and second coupling devices 201a, 201b may become engaged and clamped together by a clamping force exerted on devices 201a, 201b by first and second coupling supports 202, 204. Clamping tool 200 may thus act to connect first and second coupling devices 201a, 201b and also couple together free, proximal ends of vessel portions at an interface generally corresponding to a location between first and second coupling devices 201a, 201b.

As noted above, clamping tool 200 may also act, in some embodiments, to align first and second coupling devices 201a, 201b. For instance, as discussed previously, an example embodiment of devices 201a, 201b may each include tissue engaging portions and receiving portions that may be alternately positioned (e.g., at varying axial and/or angular positions) around a central axis of devices 201a, 201b. There may, for instance, be four tissue engaging portions on each of devices 201a, 201b, as well as four receiving portions, although more or fewer tissue engaging or receiving portions may be used as discussed herein. As illustrated in FIG. 22, coupling braces 206 of first coupling support 202 may be offset relative to coupling braces 206 of second coupling support 204. For instance, first and second coupling supports 202, 204 may have coupling braces 206 that are offset at about forty-five degrees. In some embodiments, a notch, line, or other alignment mechanism may be used to align devices 201a, 201b with corresponding supports 206. This offset and corresponding alignment may allow each coupling brace 206 to be placed at a particular location of a respective coupling device 201a, 201b. Coupling braces 206 may optionally be contoured to match a contour of devices 201a, 201b or otherwise be configured to match to a particular location on coupling devices 201a, 201b. The forty-five degree offset may also help to facilitate alignment of receiving portions with tissue engaging portions. More particularly, each of the four tissue engaging portions on a coupling device 201a, 201b may be forty-five degrees from each of two receiving portions. Thus, by aligning a corresponding one of coupling devices 201a, 201b at a forty-five degree angle, the tissue engaging portions of first coupling device 201a may be aligned with the receiving portions of second coupling device 201b, and vice versa. In a previously described example in which tissue engagement portions and receiving portions are offset at thirty-six degree intervals, or at other intervals, braces 206 of respective supports 202, 204 may be offset at thirty-six degrees or at another corresponding interval.

It will be appreciated in view of the disclosure herein that the clamping tool in FIG. 23 is merely one example of a suitable tool that can be used to clamp two coupling devices 201a, 201b together and/or to align two coupling devices 201a, 201b for installation in a vascular anastomosis, such as an end-to-end anastomosis. Other devices may also be used. For instance, while four coupling braces 206 are illustrated for each of first and second coupling supports 202, 204, there may be more or fewer coupling supports. For instance, in an embodiment in which there are five tissue engagement portions, there may be five supports, although there need not be one-to-one correspondence between braces 206 and tissue engagement portions. Accordingly, in other embodiments, there may be more or fewer coupling braces 206.

Furthermore, while only one of coupling supports 202, 204 is illustrated in FIG. 23 as movable relative to guide 210, this embodiment is merely exemplary. In some embodiments, two or more coupling supports 202, 204 may move. For instance, a ratchet device may move two coupling supports 202, 204 together. Further, while coupling braces 206 of the illustrated embodiment extend along an exterior surface of coupling devices 201a, 201b, they need not do so. For example, one or more openings may be placed on the distal faces of devices 201a, 201b. Coupling braces 206 may be replaced and/or supplemented with pins that then are inserted into such openings.

Accordingly, as described herein, multiple devices and apparatus are contemplated within the scope of the present disclosure for providing methods of performing a vascular anastomosis procedure. In some cases, the described devices and apparatus may be included within a kit. For instance, an exemplary kit may include a set of two or more coupling devices 201a, 201b packaged together. More than two coupling devices may be included where, for example, multiple different sizes of coupling devices may be used depending on the vessel(s) to be coupled or grafted. In still other embodiments, the two or more coupling devices 201a, 201b may be packaged with a clamp or other alignment device. As described herein, one or more of the clamp or other alignment device may also be combined with one or more other apparatus, such as expander or other installation tools, or may be included as separate devices. For example, first coupling support 202 and/or second coupling support 204 may be incorporated into an installation tool and expander as part of the carrier. By way of illustration, the coupling braces could additionally couple to a tapered or conical plunger that engages and expands vessel 214a and/or vessel 214b.

Various tools described herein need not, however, be included as part of a kit. For instance, in some embodiments, a coupling device may be a single-use device whereas an installation tool, clamping tool, expander, or other tool, or a combination thereof, may be reusable. Accordingly, certain tools herein are optionally made of medical grade stainless steel, aluminum, titanium, or other materials that are sufficiently robust to withstand sterilization procedures to allow for multiple uses.

Figure 24A:
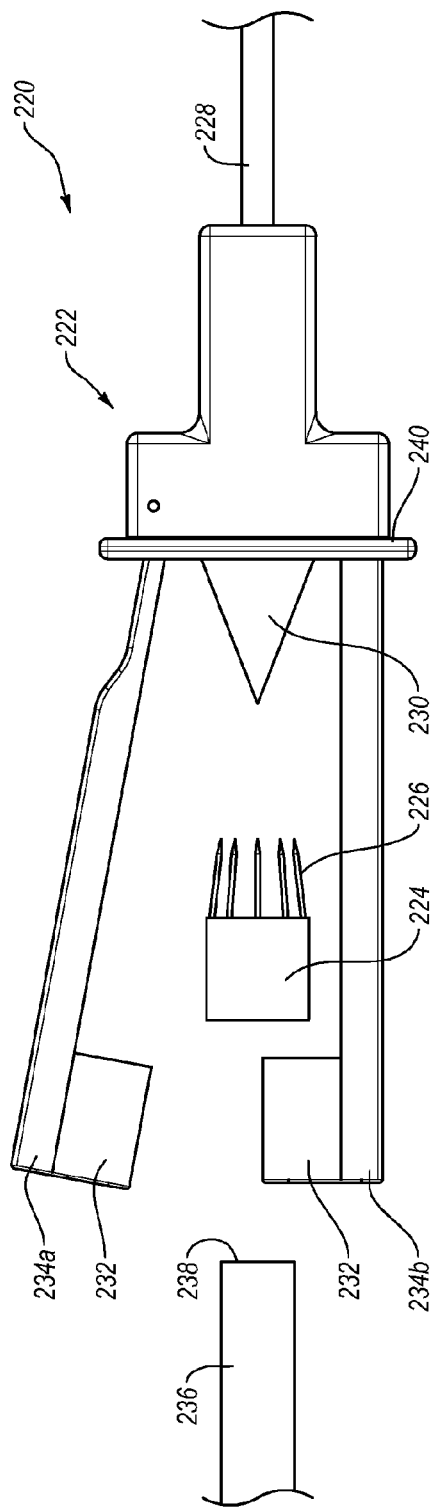
FIGS. 24A-24C illustrate a process of securing a vessel to an exemplary vascular coupling device and using an installation tool according to one embodiment of the disclosure.
Figure 24B:
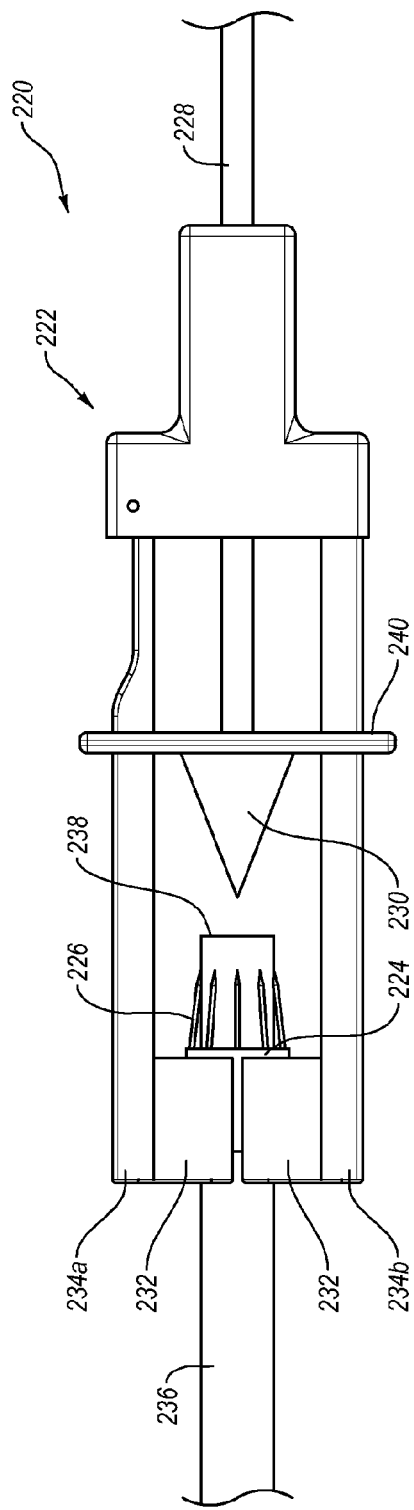
Figure 24C:
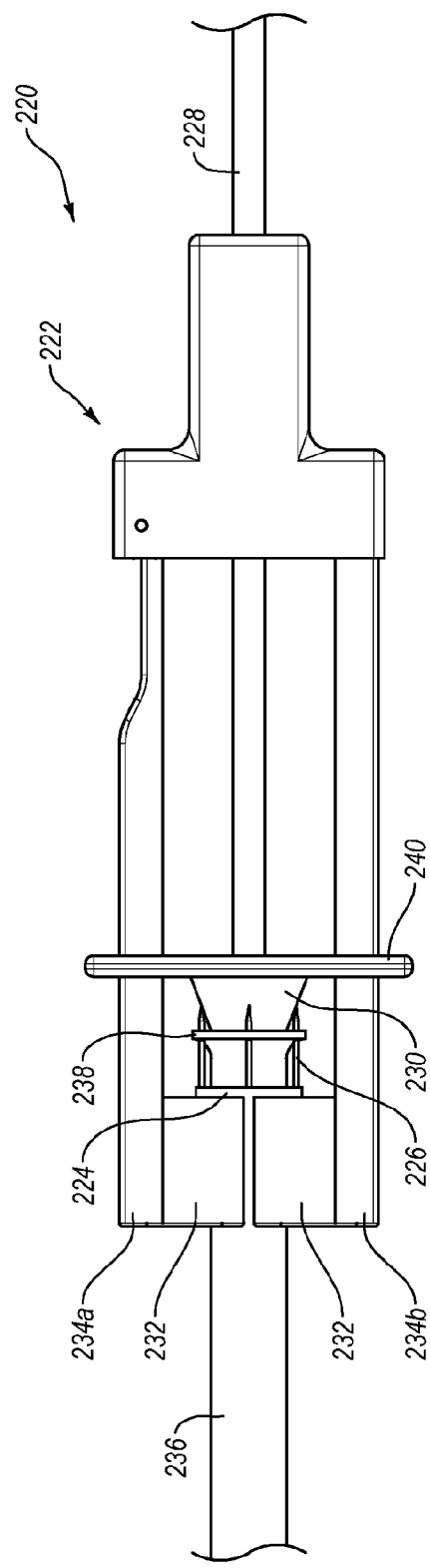

Turning now to FIGS. 24A-24C, an exemplary installation tool 220 is illustrated and described in additional detail. In some embodiments, installation tool 220 may act as an expander as described herein, and/or can be used to couple a vascular coupling device 224 to an open end 238 of a vessel 236. For instance, installation tool 220 can facilitate expanding of open end 238 of a vessel 236 and engagement of the vessel 236 to or on a coupling device 224, which device 224 and vessel 236 may then be coupled to a corresponding vessel in any suitable manner. For instance, FIGS. 10, 23, 256A-26B, and 30A-30B illustrate exemplary manners of clamping together two vascular coupling devices together, in a manner that may be performed after installation and/or expansion using the device 220.

FIGS. 24A-24C, for instance, illustrate an example installation tool 220 that includes an exemplary vessel expander 222. In this particular embodiment, installation tool 220 is multi-functional and optionally performs or facilitates multiple acts of an installation and/or preparation method for device 224. In FIG. 24A, for instance, installation tool 220 can be used to facilitate engagement between a vessel and tissue engaging portions 226 of device 224, as well as transitioning device 224 from a pre-installation configuration towards and/or to an installation configuration. Installation tool 220 may further optionally automate engagement between tissue engaging portions 226 of device 224 and tissue of the vessel 236, such that it is not necessary for all embodiments that each of the tissue engaging portions be separately engaged with the vessel. For example, the tissue can be expanded at a generally constant rate such that all of the tissue engaging portions are automatically engaged with the tissue, and optionally evert the tissue.

As shown in FIGS. 24A-24C, an exemplary installation tool 220 may include an expander shaft 228 that couples to a vessel expander 222. Vessel expander 222 may include a tapered end 230 that is, in this embodiment, a conical plunger, and may be directed towards a coupler support 232. In this embodiment, coupler support 232 is illustrated as holding or otherwise being configured to support device 224. Device 224 may be supported by installation tool 220 in a pre-installation configuration and/or a deployed, installation configuration.

Shaft 228 may act as a grip that enables an operator to control and/or manipulate vessel expander 222. For instance, shaft 228 may be moved longitudinally towards device 224 and coupler support 232, thereby also causing tapered end 230 of the vessel expander 222 to move towards device 224. Device 224 may have a vessel 236 such as a vein, artery, organ, body lumen, or the like (not shown) extended therethrough, and a free end of vessel 236 may extend from device 224 (see FIGS. 22 and 24B). Tapered end 230 is, in this embodiment, tapered such that the end most near device 224 has a smaller diameter or other dimension than the end most near expander shaft 228. In this manner, the smaller diameter portion of tapered end 230 may enter open end 238 of vessel 236 even if vessel 236 is partially collapsed. Further extension of expander shaft 228 towards vessel 236 may cause the increasingly larger dimension portions of vessel expander 222 to enter vessel 236. As the larger portions of tapered end 230 are moved inside vessel 236, vessel 236 may expand to accommodate the increased size of tapered end 230. In some embodiments, tapered end 230 may be generally circular or have another configuration that causes generally uniform expansion of vessel 236.

As vessel 236 expands, the vessel wall may move radially outward relative to a longitudinal axis of vessel 236 and/or tapered end 230. The radial expansion of the vessel walls may cause the vessel walls to expand and engage against various tissue engaging portions 226 that are included on device 224. With sufficient expansion of open end 238 of vessel 236, tissue engaging portions 226 may penetrate at least a portion of the vessel wall. In other embodiments, tissue engaging portions 226 may penetrate at least a portion of the vessel wall in the absence of expansion of the vessel.

With the vessel wall engaged by tissue engaging portions 226, installation tool 220 may be used to transform device 224 from a pre-installation configuration to a deployed, installation configuration. In the pre-installation configuration, tissue engaging members 226 of device 224 may be at an angle relative to the body of device 224 and/or a longitudinal axis thereof. For instance, tissue engaging members 226 may be at an angle between about ten and about sixty-five degrees relative to a longitudinal axis of device 224.

Further longitudinal movement of tapered end 230 may, in some embodiments, cause tissue engaging portions 226 to further expand the vessel engaged thereby. In some embodiments, the further expansion of vessel 236 may expose an interior surface to facilitate an intima-to-intima contact. More particularly, the particular installation tool 220 illustrated in FIGS. 24A-24C can include a tapered end 230 configured to engage tissue engagement portions 226. As tapered end 230 is moved towards, and ultimately engages, tissue engagement portions 226, the tips of tissue engagement portions 226 may begin to ride on the external surface of tapered end 230. As tapered end 230 continues to move towards device 224, the diameter at the point of engagement can increase, thereby causing the tips of tissue engagement portions 226 to move radially outward. In some embodiments, such motion deflects and/or deforms tissue engagement portions 226 such that when tapered end 230 is retracted, tissue engagement portions 226 remain deflected and/or deformed. Such deflection may correspond to an installation configuration of device 224. Once tissue engagement members 226 have been placed in a modified state, tissue engaging members 226 may be prepared, along with vessel 236 for an anastomosis (e.g., end-to-end, side-to-side, or other anastomosis or other procedure). For instance, device 224 can be clamped to another suitable device.

Any of a number of different materials may also be used to make or produce installation tool 220. For instance, in some embodiments, installation tool 220 may be formed of a polymer, natural or organic material, metal, alloy, composite, or other material, or a combination thereof. In one example embodiment, tapered end 230 may be formed of a substantially rigid material that can cause engagement members 226 to move radially outward, while some or all other portions of installation tool 220 are formed of a flexible or less rigid material.

As best illustrated in FIG. 24A, installation tool 220 may include guides 234a, 234b. In some embodiments, one or more of guides 234a, 234b may have a tapered configuration, or some other configuration where the width or other measurements of guides 234a, 234b changes along their longitudinal length. For instance, as illustrated in FIGS. 24A-24C, guide 234a may have a first width at the proximal end near shaft 228, and the width may increase along all or a portion of the length of guide 234a, and towards supports 232. A variable width in guide 234a may serve any of a number of different purposes. For instance, an increase in the width of guide 234a at or near the distal end of guides 234a, 234b may allow guide 234a to act as a stop to prevent or restrict movement of a carrier 240 that carries or moves with tapered end 230.

As best illustrated in FIG. 24A, a decreased width or other measurement at or near the proximal end of guide 234a may also allow installation tool 220 to at least partially open to receive a device 224 therein. By way of illustration, carrier 240 may be configured to slide along or relative to guides 234a, 234b. Carrier 240 may, for example, include one or more openings, channels, gaps, apertures, other features, or combinations thereof through which guides 234a, 234b are received. The openings may be sized to accommodate a maximum width or some other width of guides 234a, 234b. In some embodiments, guides 234a, 234b may be configured to pivot or otherwise move relative to carrier 240 or vessel expander 222 (e.g., relative to a stationary portion of vessel expander 222). When the openings of carrier 240 are positioned over a wider portion of guides 234a, 234b, carrier 240 may prevent or otherwise restrict motion of guides 234a, 234b relative to the stationary portion of vessel expander 222. If, however, the openings of carrier 240 are positioned over a narrower width of guides 234a, 234b, the size of the openings may allow guides 234a, 234b to pivot, thereby opening installation tool 220 to receive a device 224 therein, as illustrated in FIG. 24A. Furthermore, while FIG. 24A illustrates that only one of the two guides may change size and/or shape and/or be configured to pivot or otherwise move, in other embodiments both of guides 234a, 234b may be configured to pivot or otherwise move.

In view of the disclosure herein, it will be appreciated that installation tool 220 is merely one example of a suitable installation tool or expander, and that other embodiments are contemplated. For instance, in the illustrated embodiment, tapered end 230 may be movable independent of carrier 240. In other embodiments, however, the movement of vessel carrier 240 and tapered end 230 may be simultaneous or otherwise linked or correlated. In still other embodiments, an installation tool includes only a vessel expander, while a separate tool is used to expand, deflect, or otherwise change the position of tissue engagement portions 226.

While FIGS. 24A-24C illustrate a vessel expander 222 that uses a conical tapered end 230, this is merely exemplary and an expander may take any suitable form. For example, an expander may mechanically expand the walls of first vessel portion 194a, may direct air or another fluid into the lumen of vessel 236, or otherwise cause the vessel walls to expand.

Furthermore, as described herein, tissue engagement portions 226 may engage the tissue of vessel 236 and pull the vessel walls radially outward when engagement portions 226 move radially outward. In some embodiments, the proximal end of the wall of vessel 236 is expanded by tissue engaging portions 226 to increase the overall diameter of vessel 236. Expansion of vessel 236 may simply pull the vessel wall radially outward; however, in other embodiments such expansion may result in the interior surface of vessel 236 being everted, such that the interior surface is at least partially exposed at open end 238 of vessel 236. Thus, in embodiments being used in connection with vascular applications, everting the interior surface may include everting the intimal layer of the vessel.

As described herein, exemplary devices, apparatus, and tools for performing or facilitating a vascular anastomosis (e.g., end-to-end anastomosis) may be structured and/or configured in numerous different ways. The particular embodiments specifically illustrated and/or described should therefore not be used to limit the scope of the claims, particularly where various other alternatives are described herein and/or would be appreciated in view of the disclosure herein. For example, installation tool 220 described relative to FIGS. 24A-24C may be varied in a number of different manners. For instance, installation tool 220 may also be used as a clamping tool where, for instance, a second coupling device 224 is connected to, or in place of, tapered end 230.

FIGS. 25A-26B illustrate still other example embodiments of tools and/or devices that may be used in connection with some embodiments disclosed herein. For instance, FIGS. 25A-25D illustrate an exemplary installation tool 250 that may be used in connection with some embodiments of the present disclosure to couple a vascular coupling device 252 to free end of a vessel 264. In some embodiments, vascular coupling device 252 may be configured to have no moving parts, few moving parts, or such that a set of one or more tissue engagement portions 254 transitions between a pre-installation configuration and an installation configuration without the aid of moving parts.

In the particular embodiment shown in FIGS. 25A-25D, the exemplary installation tool 250 may include a set of jaws 260a, 260b that can be used to grip and/or manipulate a coupling device 252. Jaws 260a, 260b are optionally movable relative to each other. For instance, in the illustrated embodiment, jaws 260a, 260b may pivot relative to each other about a pivot 266. To facilitate selective manipulation of jaws 260a, 260b, a set of handles 262a, 262b may be coupled to jaws 260a, 260b. For instance, a first handle 262a may be secured to first jaw 260a, while a second handle 262b is connected to second jaw 260b. As handles 262a, 262b are drawn together, the distal ends of jaws 260a, 260b may also be drawn together, as shown in FIGS. 25A-25C. In the illustrated embodiment, jaws 260a, 260b are illustrated as being integral with a respective handle 262a, 262b, although such configuration is merely exemplary. In other embodiments, jaws 260a, 260b and/or handles 262a, 262b may have other configurations, or may be otherwise configured. Indeed, in some embodiments, one or more of jaws 260a, 260b or handles 262a, 262b may be eliminated entirely.

At the distal end of first jaw 260a is a coupling carrier 270a. Coupling carrier 270a may, in some embodiments, be pivotally coupled relative to jaw 260a, although such configuration is not necessary. In other embodiments, coupling carrier 270a is fixed relative to jaw 260a. In some embodiments, coupling carrier 270a may also be selectively movable relative to jaw 260a.

Coupling carrier 270 may be used to secure a coupling device 252 so as to facilitate connecting a vessel 264 thereto, and/or to facilitate clamping of the device with a corresponding anastomosis or other device. To facilitate such purpose(s), the illustrated carrier 270a may include an interior channel therethrough. The proximal end 268 of a vessel 264 may thus be inserted through the channel, starting at the distal end 258 of carrier 270a. The channel may be in fluid communication with a channel of device 252. Accordingly, as vessel 264 is moved through the channel, the vessel may exit through device 252, and proximal end 268 of vessel 264 may be positioned adjacent tissue engaging portions 254, as best shown in FIG. 25B.

Opposed to the coupling carrier 270a may be an expansion member 270b. In the illustrated embodiment, expansion member 270b can be coupled at or near the distal end of second jaw 260b. Expansion member 270b can include an expander 256, which may be a tapered end or cone, as shown in FIG. 25A, although any other expander or other similar device may be utilized. In operation, handles 262a, 262b may be drawn together, as shown in FIG. 25B. By drawing handles 262a, 262b together, expander 256 may be drawn towards free end 268 of vessel 264 and towards tissue engagement portions 254 of coupling device 252. In FIG. 25B, the tip of expander 256 aligns with vessel 264, such that the tip of expander 256 may enter into vessel 264. Such alignment may be facilitated by carrier 270a and/or expansion member 270b rotating, being fixed, or in any other suitable manner.

As expander 256 is placed further into vessel 264, vessel 264 may expand and ultimately engage tissue engagement portions 254. Tissue engagement portions 254 may be separated a distance greater than the corresponding size of expander 256 at the tips of tissue engagement portions 254. However, as expander 256 is drawn even closer to device 252, expander 256 may also engage the tips of tissue engagement portions 254. For instance, as best shown in FIG. 25C, expander 256 may engage tissue engagement portions 254 and cause them to expand or deflect radially outward. In FIG. 25C, engagement portions 254 are deflected to a position that is about parallel to a longitudinal axis of device 252, although such position is merely illustrative. As further shown in FIG. 25C, as tissue engagement structures 254 deflect outward, the engaged portion of vessel 264 may also expand radially outward therewith. As described herein, in some embodiments the expansion of vessel 264 may cause vessel 264 to become everted, although in other embodiments the intimal layer of vessel 264 may not be everted.

Following deflection of tissue engagement portions 254—which deflection may correspond to transitioning device 252 from a pre-installation state to an installation state—handles 262a, 262b or other mechanism may be used to withdraw expander 256 relative to device 252 and/or vessel 264. For instance, as shown in FIG. 25D, expander 256 is withdrawn from device 252 and tissue engagement portions 254 optionally remain in a deflected or installation configuration. Vessel 264 may also be manipulated or pulled such that a proximal end 268 of vessel 264—which end may be in an expanded state—can be fixed to tissue engagement portions 254 and optionally also drawn to be substantially adjacent the proximal end of the body of coupling device 252.

Figure 26A:
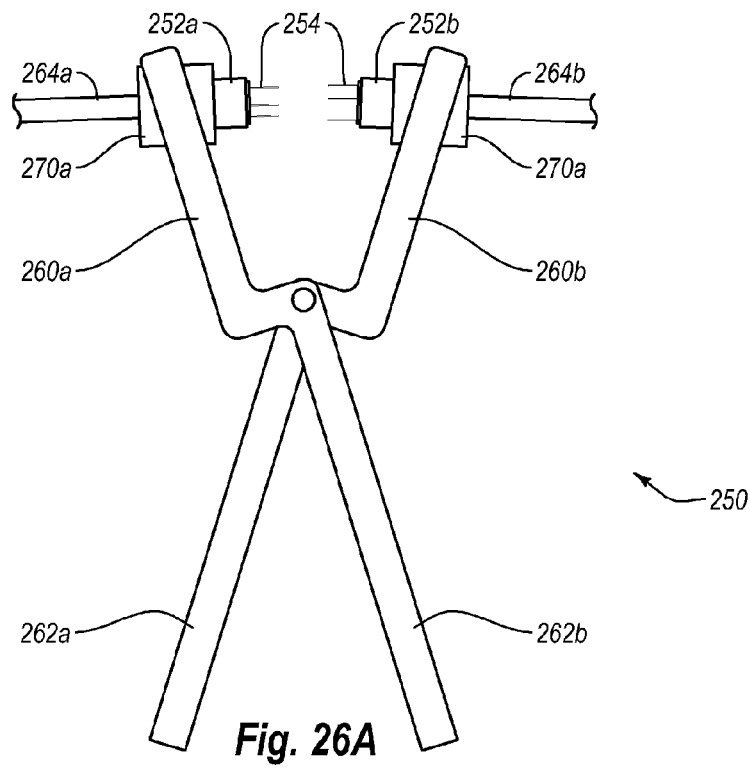
FIGS. 26A and 26B illustrate a process of connecting two vascular coupling devices in an end-to-end anastomosis procedure using the installation tool of FIGS. 25A-25D.
Figure 26B:
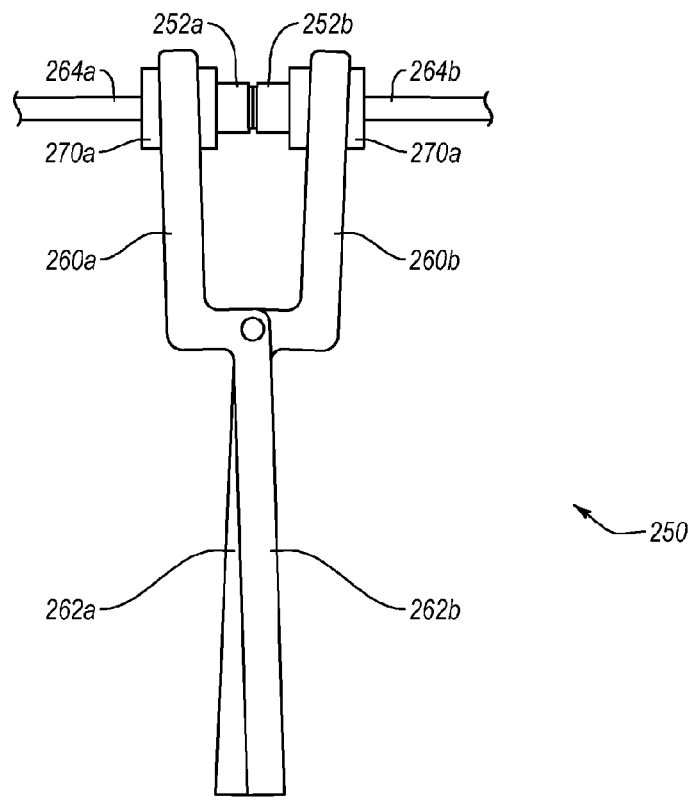

Turning now to FIGS. 26A and 26B, installation tool 250 is further illustrated in the context of a clamping device. More particularly, in at least some embodiments, installation tool 250 can be converted into a clamping device. For instance, installation device 250 of FIGS. 25A-25D may be converted into a clamping device by replacing expansion member 270b with a second coupling carrier 270a, although such an embodiment is merely illustrative. For instance, expansion member 270b may not need to be entirely replaced. Indeed, in some embodiments, expansion member 270b may be converted into a coupling carrier 270a by removing expander 256.

In FIGS. 26A and 26B, two coupling devices 252a, 252b may each be coupled to a corresponding coupling carrier 270a, each of which in turn may be positioned at or near a distal end of each respective jaw 260a, 260b. Using handles 262a, 262b, an operator may draw jaws 260a, 260b closer together (e.g., by drawing handles 262a, 262b closer together). As jaws 260a, 260b draw closer together, coupling carriers 270a also approach each other, as do respective proximal ends of coupling devices 252a, 252b.

In some embodiments, coupling devices 252a, 252b may include tissue engagement portions 254 or other structures that can also act as receiving members to maintain engagement between coupling devices 252a, 252b. By way of illustration, and as described above, a set of tissue engagement portions 254 may alternate or otherwise be associated with a set of receiving members. For instance, tissue engagement portions 254 on a coupling device may be positioned in an alternating pattern with a set of one or more holes or other openings that operate as receiving members. In operation, as the two devices 252a, 252b are drawn together, tissue engagement portions 254 may be positioned to correspond to the position of holes or other receiving structures. Engagement portions 254 may then enter the holes, or otherwise engage the opposing device 252a, 252b, thereby allowing devices 252a, 252b to engage each other and remain in an engaged configuration, as shown in FIG. 26B. Following clamping or other securement of coupling devices 252a, 252b in this manner, coupling devices 252a, 252b can be released from corresponding coupling carriers 270a. For instance, coupling carrier 270a may be segmented and held together with a latch or clamp that, when released, opens coupling carrier 270a so as to allow coupling devices 252a, 252b and vessels 264a, 264b to be removed therefrom. Any other suitable mechanism for releasing coupling devices 252a, 252b and vessels 264a, 264b from tool 250 may also be utilized.

Turning now to FIGS. 27A-27D which show various views of an embodiment of a device 300 for use in performing an end-to-end or other type of vascular anastomosis. Device 300 may be used for coupling ends of veins, arteries, tissue and other types of vessels or vasculature together, as well as with vasculature of different sizes. As shown in FIGS. 27A-27D, device 300 may include a body 302. In some embodiments, body 302 may be generally annular in shape and/or may generally surround a lumen 304 centered around a central axis 306. As used herein, an annular body may include any hollow body. For instance, an annular-shaped body may include one or more structures surrounding an opening, whether the body is substantially flat, has a significant thickness or depth, has a circular cross-sectional shape, or has a square, rectangular, hexagonal, or other cross-sectional shape. In other embodiments, body 302 may include other shapes and/or may not have a central axis 306. Body 302 may be considered annular despite changes in configuration. For instance, as discussed herein, annular body 302 may have a disk-shaped configuration and an elongated configuration.

Device 300 for performing a vascular anastomosis may include a plurality of wing elements 308. In this embodiment, wing elements 308 are illustrated as collectively defining body 302. In some embodiments, wing elements 308 may engage other structures defining all or a portion of a body. Wing elements 308 may be formed or provided in a manner such that wing elements 308 include any combination of separate, independent, connected, or integral wing elements. For instance, in FIGS. 27A-27D, wing elements 308 may be integrally connected to one or more adjacent wing elements 308 by tethers 310. Tethers 310 may be an integral part of wing elements 308, and may in some embodiments provide an interface by which one wing element 308 connects to an adjoining wing element 308. Tethers 310 may be formed along with wing elements 308 or formed in other manners (e.g., through thermal bonding).

In some embodiments wing elements 308 may be configured to rotate or otherwise move relative to each other and/or a central axis 306 of device 300. For instance, in some embodiments, tethers 310 are flexible so as to allow wing elements 308 to rotate or otherwise move relative to each other. More particularly wing elements 308 may be connected together using tethers 310 that can act as hinges, pivots, inflection points, or other elements which flex or otherwise move or act to facilitate movement of wing elements 308. In some embodiments, wing elements 308 may pivot about ninety degrees. In other embodiments, wing elements 308 may pivot or otherwise move between from about five degrees to about one hundred thirty five degrees.

Figure 27A:
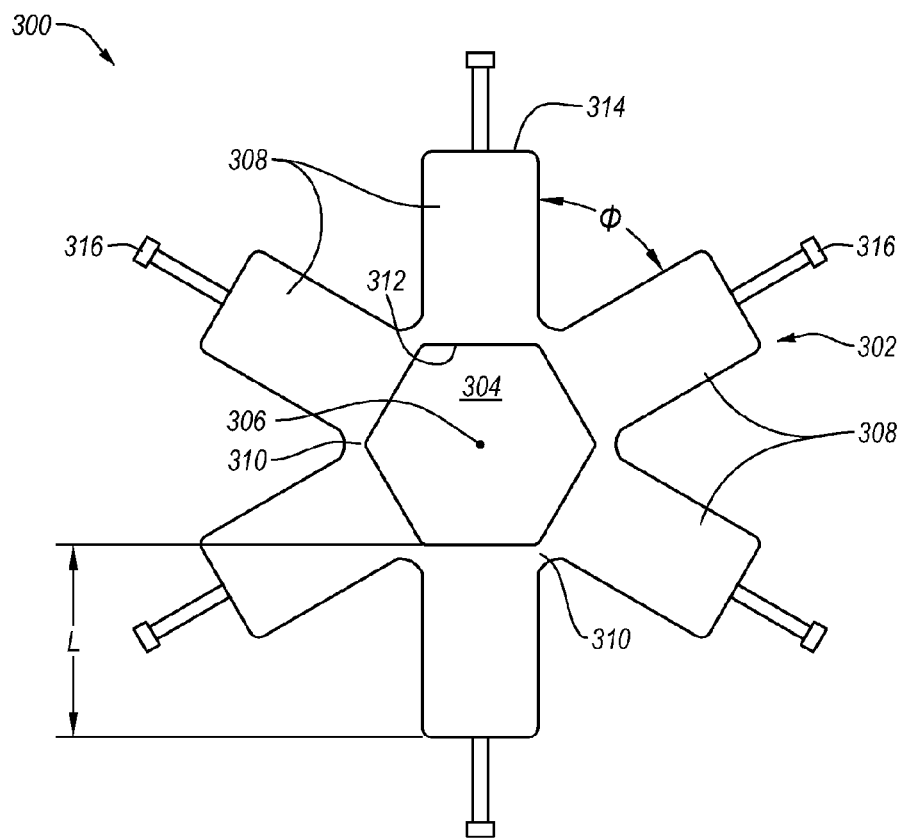
FIG. 27A illustrates a frontal view of an example vascular coupling device according to one embodiment of the disclosure, the vascular coupling device being in an unstressed state with drawn tissue engagement structures.
Figure 27B:
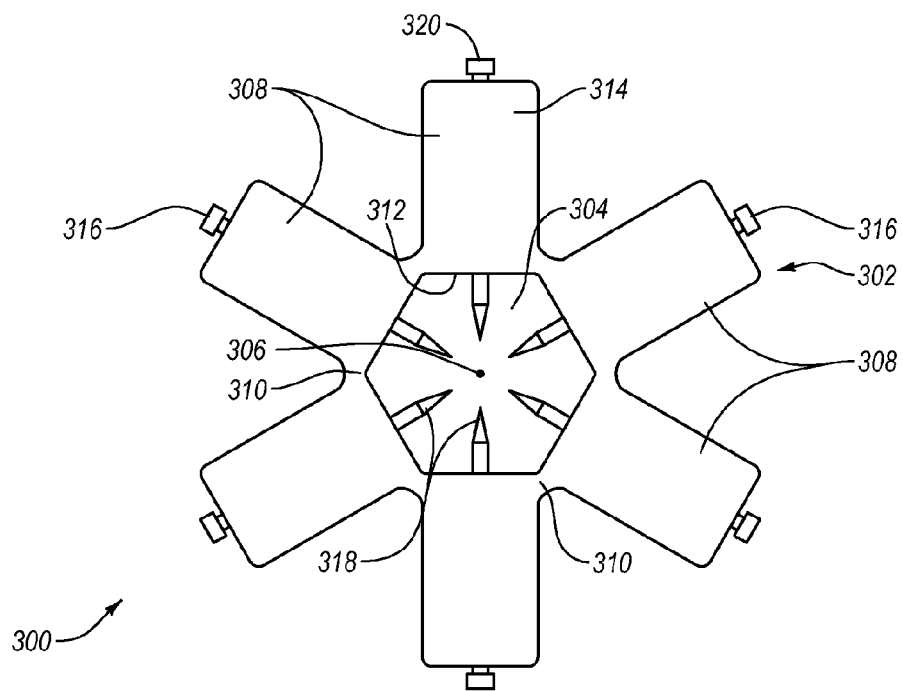
FIG. 27B illustrates a frontal view of the vascular coupling device of FIG. 27A, the vascular coupling device being in an unstressed state with depressed tissue engagement structures.
Figure 27C:
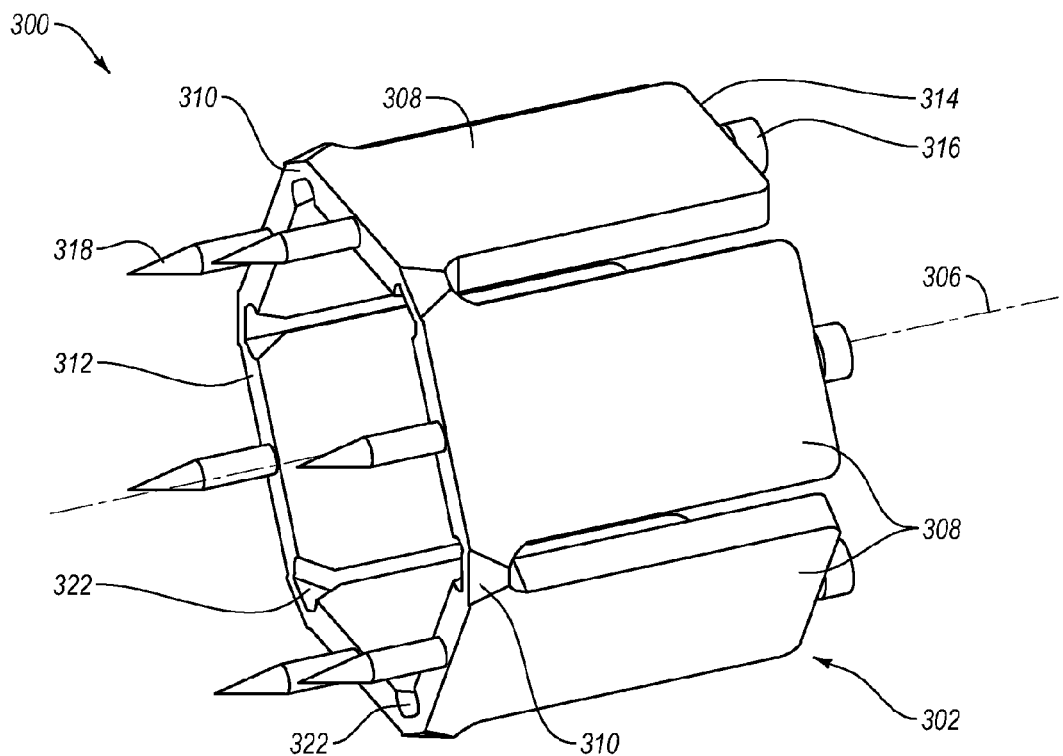
FIG. 27C illustrates a perspective view of the vascular coupling device of FIG. 27B, the vascular coupling device being in a stressed state.
Figure 27D:
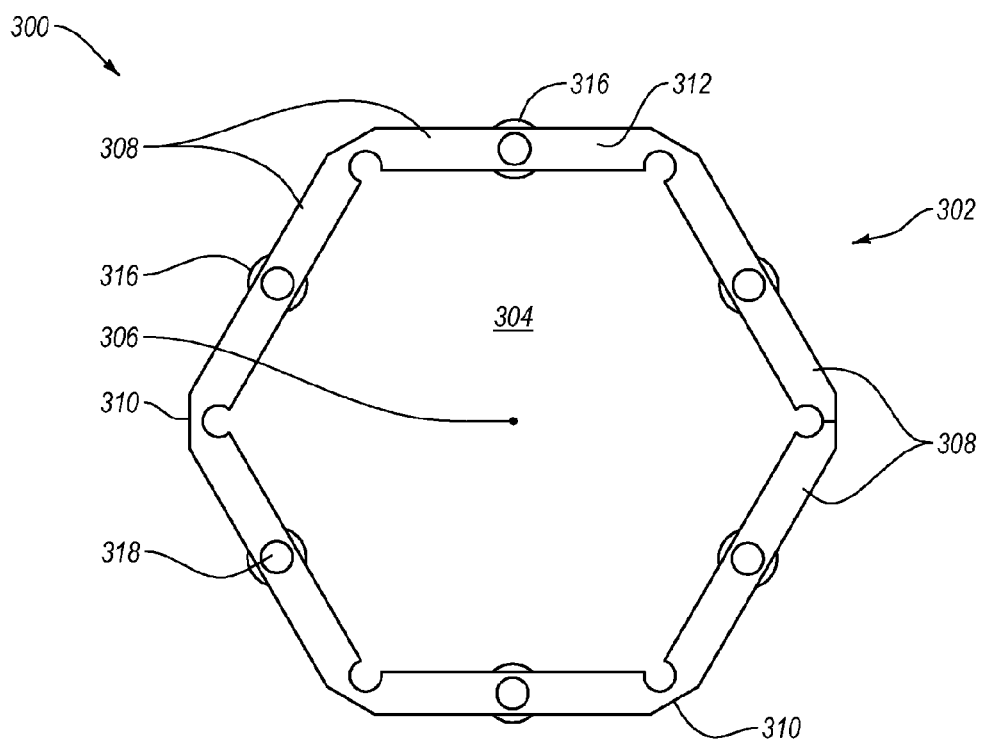
FIG. 27D illustrates a frontal view of the vascular coupling device of FIG. 27C.

In the present embodiment, there are six interconnected wing elements 308. As shown in FIGS. 27A and 27B, wing elements 308 may extend radially from central axis 306, such that each of wing elements 308 may be about perpendicular to central axis 306. As shown in FIGS. 27C and 27D, wing elements 308 may also extend longitudinally so as to be about parallel to the longitudinal, central axis 306. In some embodiments, tethers 310 may act as a living hinge such that at least some of wing elements 308 can be integrally formed.

The six wing elements 308 are also shown as being approximately equally angularly spaced at about sixty degree intervals around central axis 306. For instance, the angle ϕ may be about sixty degrees. In other embodiments, however, wing elements 308 may not be equally angularly spaced, may be about equally angularly spaced at other angular intervals, may be otherwise located relative central axis 306, may be otherwise structured, or any combination of the foregoing. For instance, in some embodiments, more or fewer than six wing elements 308 may comprise body 302, and/or the angular spacing between wing elements 308 may vary to be more or less than about sixty degrees.

As best shown in FIGS. 27A and 27B, each of wing elements 308 may have an approximate length L. The length L may generally correspond to a distance between an interior face 312 and an exterior face 314 of each wing element 308. Each wing element 308 may also have a thickness, which thickness may be substantially constant or vary across the length or width of wing elements 308. The thickness may, in some embodiments be small, and can be less than the width and/or the length of wing elements 308. For instance, device 300 shown in FIGS. 27A and 27B may have a small thickness, such that wing elements 308 collectively define an annular plate or disk-like structure.

Device 300 may also include a plurality of tissue engaging structures 316. Tissue engaging structures 316 of this embodiment may extend at least partially through wing elements 308, and in some embodiments are selectively moveable relative to wing elements 308. More particularly, as shown in FIG. 27A, tissue engaging structures 316 are shown in a withdrawn or retracted configuration. In a withdrawn or retracted configuration, tissue engaging structures 316 may be fully or partially withdrawn relative to wing elements 308 and/or radially withdrawn relative to central axis 306. For instance, tissue engaging structures 316 may be capable of being entirely withdrawn from wing elements 308. In FIG. 27A, tissue engaging structures 316 are partially withdrawn such that tissue engaging structures 316 remain at least partially within wing elements 308. Moreover, in the illustrated embodiment, tip portions 318 (FIG. 27B) of tissue engaging structures 316 are positioned within wing elements 308; however, in some embodiments, tip portions 318 may remain within lumen 304 while tissue engaging structures 316 are in a withdrawn state.

In FIG. 27B, the tissue engaging structures have been moved to a depressed, or interior configuration. More particularly, in this embodiment, tissue engaging structures 316 have been moved radially inward, towards central axis 306, such that tip portions 318 are drawn closer to central axis 306 and to each other. In some cases, the extent to which tissue engaging structures 316 can be depressed is limited. For instance, an oversized portion 320, such as a head, may be disposed on a radially outward portion of tissue engaging structures 316, and can engage exterior face 314 to prevent or reduce further radially inward movement.

Tissue engaging structures 316 may include a tip portion 318 having any number of configurations. For instance, tip portions 318 may be sharp, barbed, or otherwise configured. In at least some embodiments, tip portions 318 are used to engage and/or penetrate tissue. In the present embodiment, tip portions 318 may be sharp to facilitate engaging tissue. In some embodiments where tip portion 318 is sharp, tip portion 318 may not only engage tissue, but may also penetrate the tissue. For instance, if device 300 for performing a vascular anastomosis were used with an end of an artery or vein, tip portions 318 may fully penetrate through a side wall of the artery or vein, and into the lumen of the vessel; however, in other embodiments tip portions 318 may only partially penetrate such tissue.

As illustrated in FIGS. 27A-27D, tissue engaging structures 316 may take the form of spikes that extend through wing elements 308. To facilitate such connection, one or more apertures or openings may be formed in wing elements 308. For instance, an aperture may extend from exterior face 314, through wing element 308, and to interior face 312. In some embodiments, such an aperture may be centered within and/or extend substantially parallel to wing element 308. In other embodiments, such an aperture or mechanism for coupling the body 302 to tissue engaging structures 316 may take other forms. For instance, rather than having a plate-shaped wing element 308 with a central opening therethrough, a tube may be attached to a plate-shaped or other type of wing element 308. The tube may have an opening therein through which tissue engaging structure 316 may extend and in which tissue engaging structure 316 optionally can be selectively moved.

As illustrated in FIGS. 27A and 27B, the spiked tissue engaging structures 316 may be generally straight and can extend such that tip portions 318 are oriented generally towards central axis 306. Tissue engaging structures 316 may, however, take other forms. Tissue engaging structures 316 may instead have a curved, looped, L-shaped, or other configuration that may, for example, engage against and/or penetrate vascular tissue, a mating coupling device, or combinations thereof. Furthermore, one tissue engaging portion 316 may vary, for example, in size, shape, orientation, function, other characteristics, or combinations thereof, with respect to other tissue engaging structures 316 on the same device 300.

The vascular coupling device 300 may be configured to move between different positions, configurations or states. For instance, in accordance with at least one embodiment, vascular coupling device 300 may be moveable between withdrawn and depressed states as described above. More particularly, in a withdrawn state, tissue engaging structures 316 may be moved radially away from the central axis. In such a state, tip portions 318 optionally are withdrawn out of lumen 304 and/or out of wings 308. An example of device 300 in the withdrawn or retracted state is shown in FIG. 27A. As described herein, a device 300 in the withdrawn or retracted state may be provided to facilitate insertion of vasculature into lumen 304.

In a depressed state, device 300 may be configured to engage the vasculature within lumen 304. For instance, FIG. 27B illustrates an example device that may be in a depressed, or engagement state. In such a state, tip portions 318 of tissue engaging structures 316 may be positioned within lumen 304 so as to potentially engage and/or penetrate tissue within lumen 304.

In accordance with some embodiments, device 300 may also be movable between other or additional states. For instance, in at least one embodiment, device 300 can be selectively moved between stressed and unstressed states. In the unstressed state, for instance, device 300 may optionally be self-sustaining so as to remain at a particular shape and/or configuration. Indeed, in an unstressed state, device 300 may remain at a position or configuration without a need for added or external forces to maintain a desired shape. The plate or disk-like shape of device 300 can, in some embodiments, be a relaxed state. For instance, as described herein, wing elements 308 may be bent by the application of a force. However, if that force is released, wing elements 308 may revert to an unstressed position such as that shown in FIGS. 27A and 27B. The unstressed state may also correspond to a pre-installation state as device 300 may not yet be prepared for installation in a vascular anastomosis procedure. Vascular coupling device 300 may also be selectively placed in a stressed state that optionally corresponds to an installation state or configuration. FIGS. 27C and 27D illustrate an example vascular coupling device 300 that may be in a stressed or installation state.

To move vascular coupling device 300 from an unstressed to a stressed state, a surgeon, clinician, or other user may apply a force to each wing element 308, and in a direction that may be generally parallel to central axis 306, or which has a force component generally parallel to central axis 306. As the force is applied, wing elements 308 may be caused to bend or flex relative to each other. For instance, the movement of wing elements 308 from a radial to a longitudinal position may be obtained by stretching or otherwise using tethers 310 that exist between wing elements 308. Tethers 310 may, for instance, stretch to accommodate such movement of wing elements 308. In the stressed configuration, the user may continue to apply a force to wing elements 308 to maintain wing elements 308 in the desired position, although this is not necessary. For instance, in some embodiments, wing elements 308 may plastically deform so as to also be self-sustaining at the stressed position. In other embodiments, wing elements 308 may, if released, revert to an unstressed state similar to or different than that in FIGS. 27A and 27B.

As will be appreciated in view of the disclosure herein, a device 300 in the stressed or installation state may be adapted for use to couple a vessel or other bodily tissue to another portion of tissue. For instance, as shown in FIGS. 27B and 27C, the stressed state of the device corresponds to an elongated state or configuration of body 302. In this embodiment, body 302 extends generally longitudinally relative to central axis 306. A vessel or other tissue may then be extended through lumen 304. The length or other dimension of lumen 304 may change during the transition from an unstressed to a stressed state. For instance, in FIGS. 27A and 27B, lumen 304 may have a length generally corresponding to the thickness of wing elements 308 at interior face 312. In contrast, in FIGS. 27C and 27D, lumen 304 may have a length generally corresponding to the length L of wing elements 308. Lumen 304 may also be at least partially open in the stressed or unstressed configuration of body 302. For instance, in FIGS. 27C and 27D, tethers 310 are shown to extend only partially along the length L of wing elements 308. For instance, tethers 310 may have a length between about two to about fifty percent of the length L. In other embodiments however, tethers 310 or other connectors may have a larger or smaller length. In such embodiment, gaps may be formed between portions of adjacent wing elements 308, such that lumen 304 may be in fluid communication with the exterior of body 302.

As also shown in FIGS. 27C and 27D, at the stressed state of body 302, interior face 312 and/or exterior face 314 of wing element 308 may move or be re-oriented. By way of example, interior face 312 as shown in FIGS. 27A and 27B may generally face inward, towards central axis 306, and may have a length extending generally parallel to central axis 306. The length of face 312 may be about equal to the thickness of wing elements 308. Exterior face 314 may be similarly configured, but can extend away from central axis 306, such that the length of the face is about equal to the thickness of wing elements 308 and/or is about parallel to central axis 306. In such a configuration, a radial line drawn from central axis 306 may pass through the length L of a wing element 308.

When body 302 is positioned in the stressed state, however, faces 312, 314 may be otherwise oriented. For instance, interior face 312 may be rotated relative to central axis 306. In the embodiment illustrated in FIGS. 27C and 27D, for instance, interior face 312 has been rotated about ninety degrees such that interior faces 312 of all wing elements 308 form a face within a plane that is generally perpendicular to central axis 306. Exterior face 314 is similarly configured, such that all exterior faces may be aligned within a plane, or parallel to a plane, that is about perpendicular relative to central axis 306. A radial line may also be drawn from central axis 306 and pass through the thickness of wing elements 308.

According to some embodiments of the present disclosure, device 300 may also include one or more receiving portions 322. Receiving portions 322 may be structured, arranged, and/or configured to receive all or a portion of a second component (such as device 300b shown in FIGS. 30A and 30B). For instance, a second component may be similar to device 300 and can include a plurality of tissue engaging structures 316, prongs, locks, or other devices. In the illustrated embodiment, receiving portions 322 include openings at interior face 312 of body 302 and are approximately the same size and shape as a cross-sectional portion of tissue engaging structures 316, although receiving portions 322 may also be smaller or larger than tissue engaging structures 316, or otherwise shaped. As described herein, similarly arranged tissue engaging structures of a second component may be configured to fit into receiving portions 322 and/or facilitate coupling between device 300 and a mating device or component. Receiving portions 322 may include openings that align device 300 and a second component, may act to interlock device 300 and the second component, may provide any number of other functions, or any combination of the foregoing. For instance, in one embodiment, receiving portions 322 may have a diameter slightly less than the diameter of the tissue engaging structures of a mating component. When the corresponding tissue engaging structures engage receiving structures 322, an interference fit may be formed. In some embodiments, the walls of receiving portions 322 may be engaged by a barb or tip of the tissue engaging structures of a corresponding second component to secure device 300 to the mating component. In the illustrated embodiment, receiving portions 322 may be fully or partially defined by tethers 310. For instance, the tethers may have a curved or other profile. When tethers 310 are stretched or otherwise move as wing elements 308 change from a pre-installation configuration to an installation configuration, the curved profile may take the shape of receiving portions 322 and be aligned to be about a same distance from central axis 306 as tissue engaging structures 316. In the illustrated embodiment, receiving portions 322 are defined as partially open apertures that extend along a length of tethers 310 and are open at an interior side to be in fluid communication with lumen 304. Receiving portions 322 may also be configured in other manners.

While a mating component may be similar or about identical to device 300, other embodiments are contemplated in which a mating device is significantly different in at least some respects when compared to device 300. For instance, device 300 as described herein may be used in connection with an end-to-end anastomosis procedure in which two ends of an artery, vein, tissue, or other vessel are coupled together. In such a case, a mating device similar to device 300 may be used. The mating component may be similarly configured in size and/or shape, although this need not be the case. For instance, vessels of differing sizes may be coupled, such that at least portions of the mating devices may vary. Mating vascular coupling devices may also vary in terms of type, style, configuration, or combinations thereof. In another embodiment, device 300 may be used in other types of anastomosis procedures, including an end-to-side anastomosis procedure. One skilled in the art in view of the disclosure herein can appreciate that a mating device may include a side wall of a mating vessel and/or a mating coupling device that facilitates end-to-side anastomosis in lieu of end-to-end anastomosis.

According to some embodiments, device 300 may be maintained in the stressed configuration permanently or for only a period of time. For instance, the stressed configuration may correspond to a deployed configuration or installation configuration. In the installation configuration, wing elements 308 may be pressed inward to give the illustrated device 300 a generally cylindrical appearance. As discussed previously, one or more tissue engaging structures 316 may extend through or along wing elements 308. As wing elements 308 move into the installation configuration, the tissue engaging structures may also move in relation thereto. For instance, tissue engaging structures 316 may move from a radially oriented configuration in which the tissue engaging structures are about perpendicular to central axis 306 (see FIGS. 27A and 27B) to a longitudinally oriented configuration in which tissue engaging structures 316 are about parallel to central axis 306 (see FIGS. 27C and 27D). As discussed hereafter, movement of tissue engaging structures 316 in such a manner—and potentially combined with movement of the tissue engaging structures between retracted and depressed states—can potentially secure vascular coupling device 300 to joined tissue.

The shapes, sizes, configurations, number, other features of wing elements 308, or any combination of the foregoing, may also be suitably varied and still remain within the scope of the present disclosure as contemplated herein. As one illustrative example, device 300 includes six wing elements 308 that are oriented around a perimeter and at approximately sixty degree angular intervals, such that lumen 304 has a generally hexagonal shape. In other embodiments, however, there may be more or fewer than six wings 308. For example, there may be five or fewer wings, or there may be seven or more wings.

Wing elements 308 in the illustrated embodiment are also shown as having generally planar surfaces. In some embodiments, wing elements 308 may be otherwise configured, and can have curved or other profiles thereon. For instance, wing elements 308 may have a curved profile on at least one side thereof such that when wing elements 308 are placed in the engagement configuration, a curve profile of outer, longitudinal surfaces and/or interior, longitudinal surfaces of wing elements 308 collectively define a curved profile simulating an exterior or interior cylindrical surface. The illustrated and described shape of wing elements 308 is, however, only one possible configuration. In other embodiments, the surfaces of wing elements 308 may have different curvature radii, may have irregular shapes, may have a surface treatment applied thereto, may be otherwise varied, or a combination thereof.

The described embodiments of a device 300 for facilitating a vascular anastomosis may be manufactured using various manufacturing processes. In the embodiment illustrated in FIGS. 27A-27D, for instance, a micro-manufacturing process may shape wing elements 308 out of a biocompatible material. For instance, exemplary biocompatible materials may include organic materials, metals, alloys, polymers, composites, and combinations thereof. According to one example, wing elements 308 may be made from a biocompatible material such as silicone or high density polyethylene (HDPE). In other embodiments, biocompatible materials such as titanium, cobalt, platinum, nickel, stainless steel, other materials, alloys thereof, or combinations of the foregoing may also be utilized.

Body 302 may be designed to remain in the body indefinitely, or may degrade over time. For instance, wing elements 308 may be formed of a biodegradable, bioerodable, bioresorbable, or other degrading or resorbing material or combinations thereof. Examples of such materials that may be suitable for the manufacture of device 300 may include copolymers, such as a copolymer of L-lactic acid and glycolic acid.

Tissue engaging structures 316 may also be formed from any suitable material. Such materials may also be biocompatible and can include organic materials, metals, alloys, polymers, composites, or combinations thereof. Tissue engaging structures 316 may also be a biodegradable, bioerodable, bioresorbable, or other degrading or resorbing material or combinations thereof. For instance, in one embodiment, tissue engaging structures 316 may be formed from a polymer or a stainless steel alloy; however, in other embodiments, the tissue engaging structures may be formed from titanium, nickel, nickel-titanium alloy (e.g., NITINOL®), cobalt, chromium, platinum, or other materials, or combinations thereof. Furthermore, any or all portions of device 300 may, in some embodiments, be coated with other materials, such as biocompatible materials. For instance, the interior surfaces of wing elements 308 that define lumen 304 while body 302 is in the installation configuration may be coated with a friction reducing material that allows vasculature to easily slide therein.

Device 300 may also, in some embodiments, be configured to deliver drugs or beneficial agents to the vessel, a site proximate the vessel, another location, or combinations thereof. For instance, therapeutic agents, pharmaceuticals and/or radiation therapies may be provided or facilitated by device 300. Device 300 and/or a coating material may contain a beneficial agent, drug, or other agent that may improve the use of device 300, the success rate of a procedure in which device 300 is used, other health or other aspects of a patient, or combinations thereof. Any number of different types of drugs, beneficial agents, balms, or other elements or components, or combinations thereof may have delivery facilitated by device 300. Examples may include antiallergic substances, antiarrhythmics, antibiotics, anticoagulants, antifibrins, anti-inflammatories, antimitotics, antineoplastics, antioxidants, antiplatelet agents, antiproliferatives, antisense agents, antithrombotics, cell adhesion inhibitors, cell permutation enhancers, endothelial cell recovery promoting agents, gene-based agents, growth factor inhibitors, hemostatic agents, hyperplasia inhibitors, oligonucleotides, radiopaque agents, smooth muscle proliferation inhibitors, thrombolytics, and combinations thereof.

The size of devices 300 described herein may also be varied. For instance, in one embodiment, the devices may be sized to accommodate arteries, veins, tissue, or other vessels in the range of about one millimeter to about four millimeters. The vessels may, however, be larger or smaller. For instance, the embodiments described herein can also accommodate vessels larger than four millimeters (e.g., between about four millimeters to about 20 millimeters).

In at least one embodiment, body 302 is formed as an integral unit, with each of wing elements 308 integrally formed and joined with two adjacent wing elements 308. To form body 302 in such a manner, wing elements 308 and tethers 310 may be integrally formed in a machining, molding, casting, stamping, or other process. For instance, body 302 may be integrally formed in a single mold. In other embodiments, however, body 302 may be formed of two or more separate components that are thereafter permanently or temporarily coupled together.

Figure 28A:
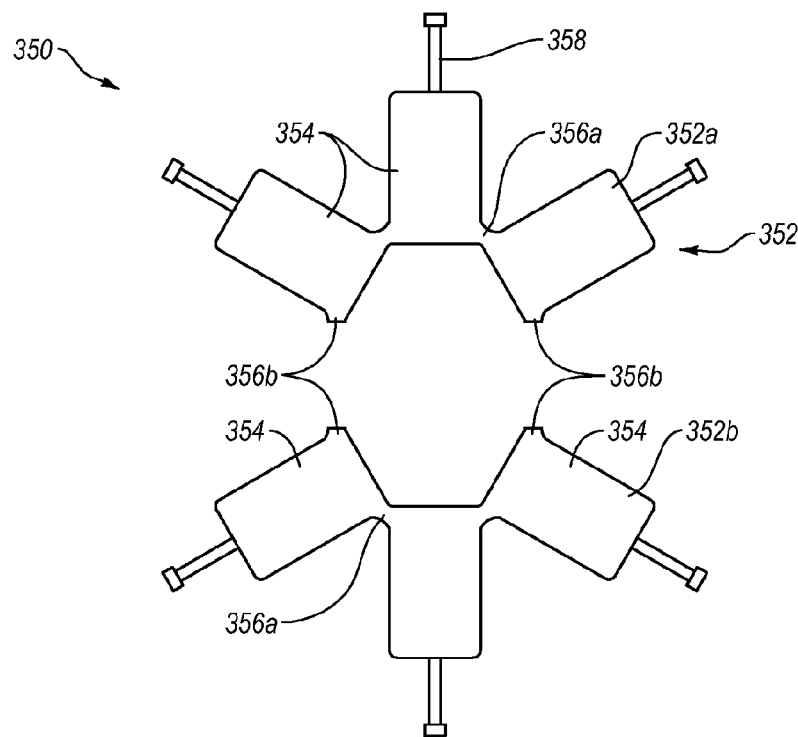
FIG. 28A illustrates a frontal view of an example vascular coupling device according to one embodiment of the disclosure, the vascular coupling device being in an unstressed state and partially assembled.
Figure 28B:
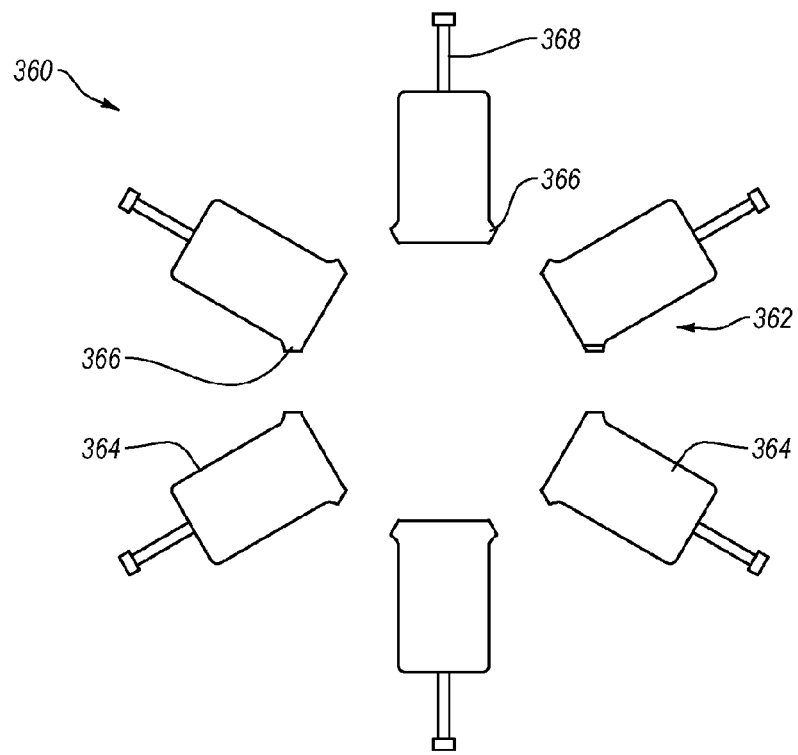
FIG. 28B illustrates a frontal view of an example vascular coupling device according to one embodiment of the disclosure, the vascular coupling device being in an unstressed state and being disassembled.

For instance, FIGS. 28A and 28B illustrate vascular coupling devices 350 and 360, respectively, in which the body of the device may be formed from at least two separate components. More particularly, FIG. 28A illustrates an embodiment in which a body 352 can be formed from mating first and second portions 352*a*, 352*b*. By way of illustration, first and second portions 352*a*, 352*b* may be halves of body 352 and may be substantially identical or similar. As shown in FIG. 28A, first and second body halves 352*a*, 352*b* can each be formed from multiple wing elements 354. In this embodiment, for instance, each of halves 352*a*, 352*b* is formed from three wing elements 354 joined together by two tethers 356*a* that can provide the interfaces connecting the three wing elements 354 together.

At the outermost two wing elements 354, there may also be tethers 356*b*. Tethers 356*b* may be configured to be selectively attached to an adjoining wing element 354 from a separate body portion 352*a*, 352*b*. For instance, first body portion 352*a*, may have outermost wings 354, each of which has a tether 356*b* attached thereto. Second body portion 352*b* may also have outermost wings 354 that each have a tether 356*b* attached thereto. To form body 352 in a manner that connects body portions 352*a*, 352*b* to provide a shape similar to that of body 302 of FIGS. 27A and 27B, tethers 356*b* of respective body halves 352*a*, 352*b* can be coupled together. Such a coupling can be made in any number of suitable manners. For instance, a welding, soldering, thermal bonding, or other process may be used. In other embodiments, an adhesive may be used to connect body halves 352*a*, 352*b* together. In still other embodiments, tethers 356*b* may be configured for use with a mechanical fastener. For instance, tethers 356*b* may collectively define an opening into which a pin may be placed to define a connection, although a lock fit or other mechanical fastening mechanism may also be used. Thus, in some embodiments, a vascular coupling kit may include two or more portions of a body (e.g., in the form of wing elements 354 and/or body halves 352*a*, 352*b*), a set of tissue engaging structures (e.g., structures 358), and optionally one or more materials or components for coupling two or more body portions together.

Although vascular coupling device 350 has been shown and described as comprising two body halves 352*a*, 352*b* that may be selectively attached to one another with tethers 356*b*, device 350 may be formed of a single body piece, similar to device 300. For instance, body halves 352*a*, 352*b* may be integrally formed by replacing at least some of tethers 356*b* with tethers 356*a* such that the two body halves 352*a*, 352*b* are formed as a single unit. In another example, body halves 352*a*, 352*b* may be separately formed, but connected on one side by tethers, such as tethers 356*a*, 356*b*. Nevertheless, the body 352 may include an opening in the side thereof between two adjoining wing elements 354, similar to FIG. 28A. The at least two adjoining wing elements 354 may include tethers 356*b* that allow the two adjoining wing elements 354 to be selectively attached to one another.

In use, device 350 may be able to expand to form a generally C-shape by spreading the two adjoining wing elements 354 apart when the two adjoining wing elements 354 are not attached to one another via tethers 356*b*. Spreading the adjoining wing elements 354 apart allows for device 350 to be passed over the side of a vessel rather than the end of the vessel. Once device 350 is positioned around the vessel, device 350 may be compressed so that the two adjoining wing elements 354 are positioned adjacent to one another. Tethers 356*b* may then be used to secure the two adjoining wing elements 354 together.

Device 350 may be formed to retain a generally circular shape even when the two adjoining wing elements 354 are not connected together via tethers 356*b*. Thus, once device 350 has been positioned around a vessel, tethers 356*b* may not be required to retain device 350 around the vessel. Additionally, when device 350 is connected to a corresponding device 350 positioned on the end of another portion of the vessel, as described herein, tissue engaging structures 358 may be received within receiving portions of the corresponding device 350 (similar to receiving portions 322 shown in FIG. 27C). Positioning tissue engaging structures 358 within the receiving portions of the corresponding device 350 may provide additional structure stability to device 350.

It should be appreciated in view of the disclosure herein that it is not necessary that the body of a vascular coupling device be formed as a single, integral unit, or as two halves that are subsequently joined. Indeed, in some embodiments, multiple portions of a body may be separately formed and later joined without the use of body halves. Thus, multiple body portions of any number may be separately formed and thereafter joined in a suitable manner.

For instance, FIG. 28B illustrates another example embodiment of a vascular coupling device 360 in which body 362 can be formed from more than two body portions. More particularly, in this embodiment, each wing portion 364 may be individually and/or independently formed or provided. Each wing portion 364 may have two tethers 366 on opposing sides thereof, although it is not necessary that the two tethers 366 on each wing portion 364 be identical or similar. Tethers 366 may be configured to attach to mating tethers 366 on adjacent wing elements 364. Such an attachment may occur in any suitable manner, such as those described previously, and can include the use of adhesives, mechanical fasteners, thermal bonding, laser welding, or any other suitable method or a combination of the foregoing. Device 360 may also be provided as a kit, and can include six separate wings 364, along with six corresponding tissue engaging structures 368, although more or fewer wings 364 and/or tissue engaging structures 368 may be provided. Further, in any kit described herein, components may be provided for two or more vascular coupling devices so as to provide mating components for a vascular anastomosis or other procedure.

Figure 29A:
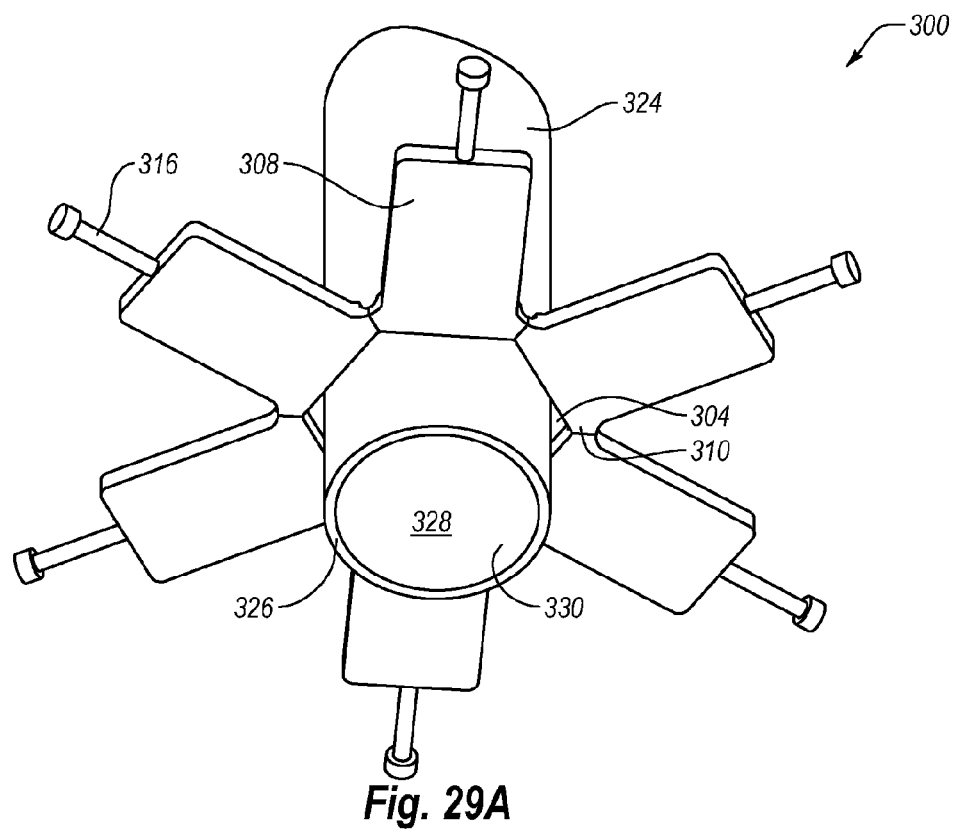
FIGS. 29A-29C illustrate exemplary steps of a method for attaching a vascular coupling device to vasculature.
Figure 29B:
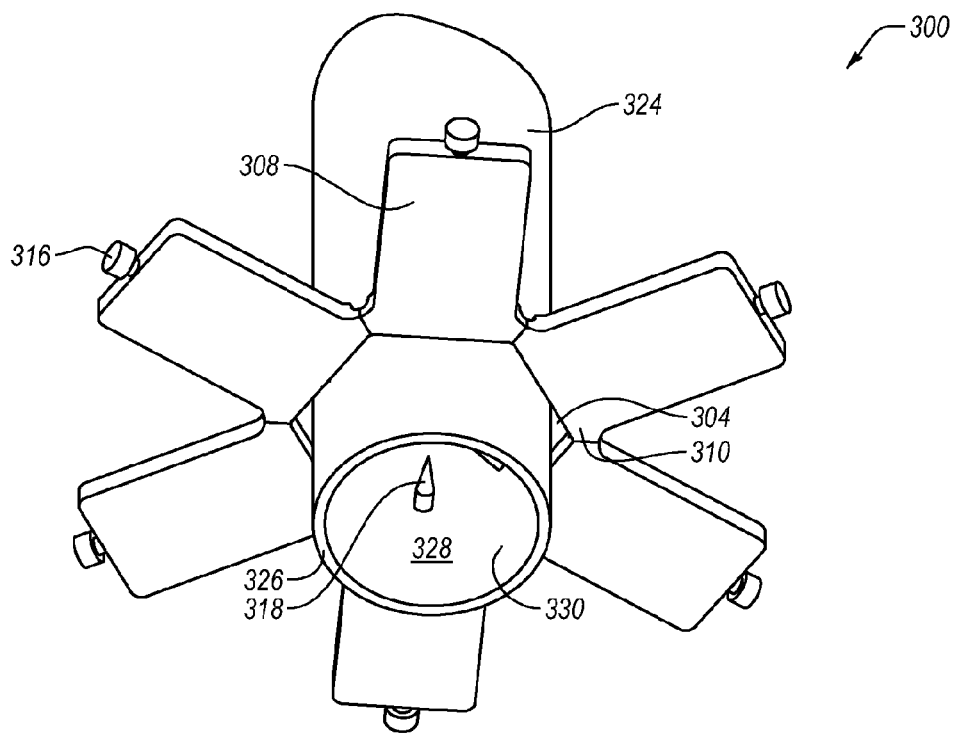
Figure 29C:
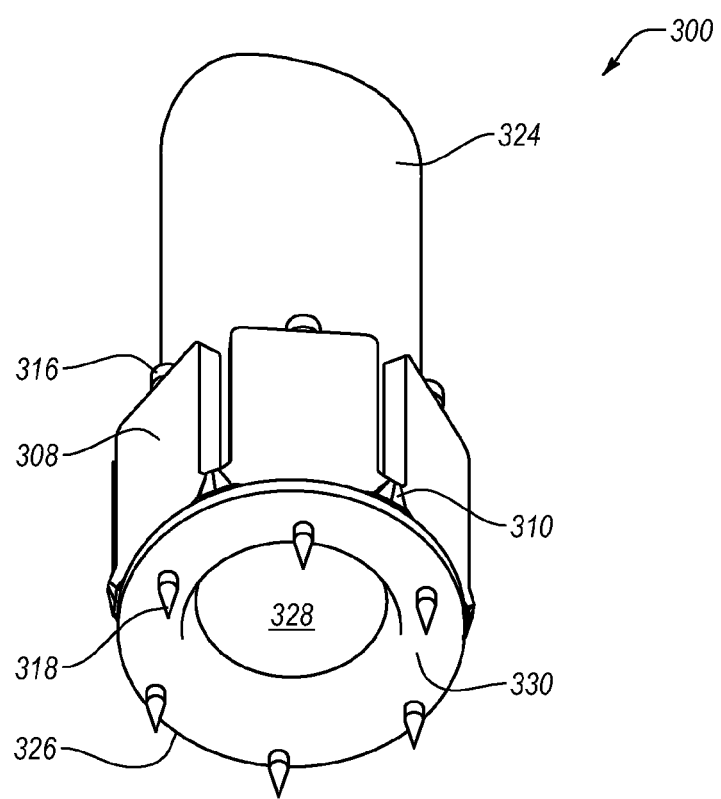

Reference will now be made to an exemplary method for using device 300 of FIGS. 27A-27D in performing an end-to-end vascular anastomosis according to one embodiment of the present disclosure. The described method is generally illustrated with respect to FIGS. 29A-30B. In particular, FIGS. 29A-29C illustrate an exemplary method for engaging or attaching a vascular coupling device 300 to a vessel, while FIGS. 30A and 30B illustrate a method for coupling mating vascular coupling devices to also couple two ends of vessels together. It will be appreciated that other methods and/or devices may be used in accordance with embodiments of this disclosure. As discussed above, embodiments of the present disclosure may also be used in side-to-end anastomosis procedures, and/or other procedures.

As shown in FIG. 29A, a vessel 324 has been cut or otherwise separated, such that a free end 326 is exposed. According to one method for performing a vascular anastomosis, free end 326 of vessel 324 is associated with a corresponding vascular coupling device 300. For example, the free end 326 may be inserted through a central opening in the vascular coupling device 300. In another example, the vascular coupling device 300 may be configured such that the vessel 324 is positioned through an opening in the side of the vascular coupling device. Vessel 324 may be a blood vessel such as a vein or an artery, although the method is not so limited, and may be used in connection with other body vessels and/or organs.

In FIG. 29A, vessel 324 has been associated with vascular coupling device 300 by passing free end 326 of vessel 324 through a lumen 304 within device 300. In some embodiments, the size of lumen 304 may correspond generally to the size of vessel 324. For instance, prior to inserting vessel 324 through lumen 304, calipers, a measuring gage, or another measuring device may be used to determine an approximate diameter or other size of vessel 324. For instance, a surgeon or other person participating in the vascular anastomosis treatment may select a device 300 that has a lumen diameter approximately matching the external diameter of vessel 324. Device 300 may be available in a number of different sizes, and optionally may be color coded so that a particular color of a device or packaging corresponds to a particular size of lumen 304. Accordingly, within the described method, a measurement of vessel 324 and a selection of a particular size of device 300 may be performed.

As vessel 324 is positioned within lumen 304 of device 300, free end 326 of vessel 324 may pass fully through the body defined by multiple wing elements 308 and/or tethers 310 of device 300. In passing vessel 324 through device 300 in this manner, device 300 may have tissue engaging structures 316 in a fully or partially withdrawn state such that vessel 324 can pass through lumen 304 in a substantially unobstructed manner.

One aspect of tissue engaging structures 316 is that they may be adapted to engage the wall of vessel 324, and optionally pass fully or partially through a wall thickness of vessel 324. In FIG. 29B, for instance, tissue engaging structures 316 may pass through the full wall thickness and enter into lumen 328 of vessel 324. In other embodiments tissue engaging structures 316 may pass only partially through the wall thickness of vessel 324.

Tissue engaging structures 316 may be caused to engage and optionally penetrate the wall of vessel 324 in any suitable manner. In one embodiment, for instance, tissue engaging structures 316 can be moved radially inward relative to wing elements 308 of device 300. Tissue engaging structures 316 may thus optionally be moved independent of wing elements 308 and depressed inward relative to a central axis of device 300. By depressing tissue engaging members 316 in this manner, tip portion 318 of tissue engaging structures 316 may move radially inward relative to central axis 306. As tip portion 318 moves a sufficient distance radially, tip portion 318 can pass fully or partially through a wall of vessel 324.

Once vessel 324 is in a position similar to that illustrated in FIG. 29B, wing elements 308 may be moved or otherwise manipulated. For instance, wing elements 308 may be biased to remain in an unstressed state; however, upon applying a force to wing elements 308, wing elements 308 move and optionally rotate relative to vessel 324. More particularly, wing elements 308 may rotate so as to transition to a stressed or engagement configuration such as that illustrated in FIG. 29C. In FIG. 29C, wing elements 308 have been rotated to extend longitudinally in a direction generally parallel to vessel 324, rather than perpendicular thereto as shown in FIGS. 29A and 29B.

As wing elements 308 are rotated or otherwise moved relative to vessel 324, the distance between tip portions 318 of tissue engaging structures 316 may also change. For instance, in some embodiments, tip portions 318 may move radially outward as wing elements 308 are moved to a stressed state. Optionally, tissue engaging structures 316 may also change orientation during such movement. For instance, tissue engaging structures 316 may transition from being positioned radially relative to vessel 324 as shown in FIG. 29B, to a substantially parallel orientation as shown in FIG. 29C. The previously described manner for causing tissue engaging structures 316 to engage vessel 324 is merely one example. For instance, wing elements 308 may begin in a stressed configuration and then be allowed to revert to an unstressed configuration.

As wing elements 308 and/or tissue engaging structures 316 move radially outward to the configuration illustrated in FIG. 29C, tissue engaging structures 316 may remain engaged with vessel 324. In some cases, tips 318 of tissue engaging structures 316 may have penetrated at least a portion of vessel 324. In the illustrated embodiment, for instance, six tissue engaging structures 316 have each penetrated the exterior wall of vessel 324. The six tissue engaging structures 316 may further grip or otherwise maintain such engagement and/or penetration with vessel 324 as tissue engaging structures 316 are moved.

When tissue engaging structures 316 move while maintaining engagement with vessel 324, the wall of vessel 324 may be expanded. For instance, in FIG. 29C, free end 326 of the wall of vessel 324 is expanded by tissue engaging structures 316 to increase the overall diameter of vessel 324. Expansion of vessel 324 may result in interior, intimal surface 330 of vessel 324 being everted, such that interior surface 330 is at least partially exposed at free end 326 of device 300. Thus, in embodiments being used in connection with vascular applications, everting interior surface 330 may include everting the intimal layer of the vessel.

With wing elements 308 depressed or otherwise in the illustrated position, device 300 may be may be in a stressed and/or installation configuration. If wing elements 308 are released, wing elements 308 optionally return to an unstressed, relaxed or pre-installation configuration; however, in some embodiments, a locking mechanism may cause wing elements 308 to remain in the deployed configuration permanently, or until the locking mechanism is selectively released. Any suitable locking mechanism may be used, and one such mechanism is described hereafter with reference to FIG. 31.

Now referring to FIGS. 30A and 30B, a method for performing a vascular anastomosis may also cause wing elements 308a, 308b to be locked in stressed position by coupling a vascular coupling device 300a, 300b with a mating component. For instance, device 300a of the illustrated embodiment may be coupled to a first vessel portion 324a and can include tissue engaging structures 316a alternately disposed around the periphery of device 300a along with receiving portions 322a. Receiving portions 322a may be holes or openings angularly spaced around device 300a.

A mating second device 300b may be connected to a second vessel portion 324b in a manner similar to that of first device 300a and first vessel portion 324a. Second device 300b may be rotated relative to first device 300a, such that tissue engaging structures 316b of second device 300b are generally aligned with receiving portions 322a of first device 300a. Corresponding alignment between tissue engaging structures 316a of first device 300a may also be made with receiving portions 322b of second device 300b.

Receiving portions 322a, 322b illustrated in FIG. 30A may be holes, and may have a generally circular cross-sectional shape along all or a portion of the length thereof. Receiving portions 322a, 322b may, however, have any number of other configurations, sizes, shapes, other features, or combinations thereof. For instance, a receiving portion may be a slot, a male or female connector, a twist lock feature, some other feature, or a combination thereof. Further, one or more of receiving portions 322a, 322b may have a shape, size, configuration, other feature, or combination thereof, that varies with respect to other receiving portions 322a, 322b its respective device 300a, 300b.

When corresponding tissue engaging structures 316a and receiving portions 322b are aligned, first and second devices 300a, 300b may be drawn together as shown in FIG. 30B. As first and second devices 300a, 300b move towards each other, tissue engaging structures 316a may enter the receiving portions 322b, and tissue engaging structures 316b may enter receiving portions 322a. Further advancement of first and second devices 300a, 300b towards each other may also cause the exposed ends of first and second vessel portions 324a, 324b to engage. As noted previously, the interior surfaces of first and second vessel portions 324a, 324b may have been exposed at the respective free ends thereof. Consequently, when the free ends are drawn into contact, an intima-to-intima contact may be formed, which may achieve a substantially tight seal at the interface between first and second vessel portions 324a, 324b.

As discussed herein, first and second devices 300a, 300b may be maintained in their deployed and coupled state for an indefinite period of time to facilitate sealing between first and second vessel portions 324a, 324b, and to effectively couple first and second vessel portions 324a, 324b in an end-to-end vascular anastomosis. For instance, tissue engaging structures 316a, 316b may form an interference fit with corresponding receiving portions 322a, 322b such that first and second devices 300a, 300b are maintained in the coupled state.

While the illustrated embodiment generally illustrates substantially identical first and second devices 300a, 300b, it should be appreciated that this is merely one example in which devices and methods of the present disclosure may be used. For example, in other embodiments, first and second devices 300a, 300b may have different sizes, be differently shaped, have varying configurations, or a combination thereof. By way of illustration, it is not necessary that the end-to-end anastomosis be performed by coupling first and second vessel portions 324a, 324b of the same size. One vessel portion may be of a smaller size than the other, such that the interior lumen of one of devices 300a, 300b may be a different size than that of the other of devices 300a, 300b.

In still other embodiments, devices 300a, 300b may have other coupling mechanisms. For instance, the devices may facilitate a male/female connection, with one of the devices having a male connector and the other device including a female connector. In other embodiments, the tissue engaging structures may have a different configuration. For instance, the tissue engaging structures may include a hook. The hook may in turn be received within a receiving slot in a mating device. Upon thereafter advancing (e.g., rotating) the coupling devices relative to each other, the hook may travel within a channel connected to the device, such that the two mating couplers are securely attached to each other in a manner that facilitates sealing between the two ends of the joined vessel.

Figure 31:
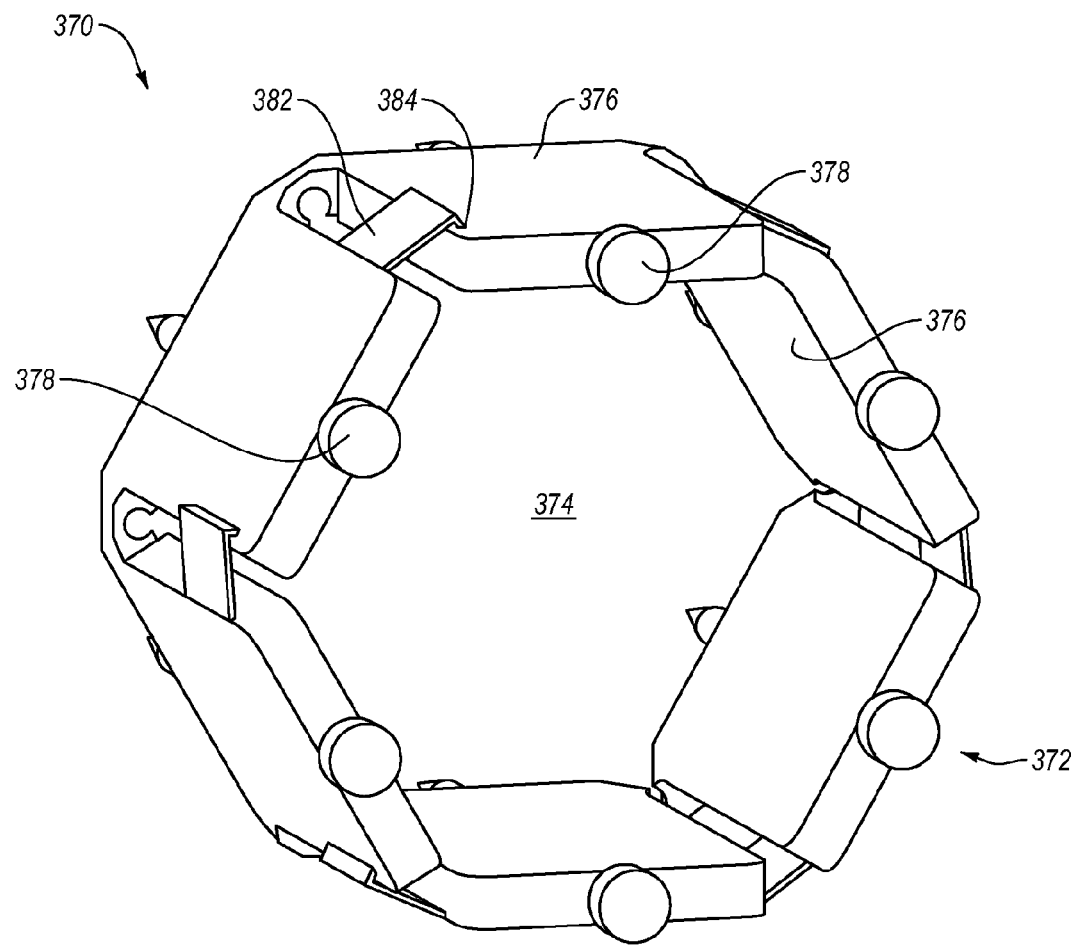
FIG. 31 illustrates a rear perspective view of another example vascular coupling device according to one embodiment of the present disclosure.

In addition to, or as an alternate for, devices 300a, 300b remaining in the stressed state by an engagement between tissue engaging structures 316a, 316b and receiving portions 322a, 322b, additional or other locking or engagement mechanisms may also be employed. Any suitable mechanism may be used and can facilitate causing devices 300a, 300b to remain in stressed or installation states even after a user ceases applying a pressure to wing elements 308a, 308b. As shown in FIG. 31, for instance, a vascular coupling device 370 may include one or more locking mechanisms 382. Locking mechanism 382 may act to restrain wings 376 with respect to a particular location relative to body 372. In FIG. 31, for instance, locking mechanism 382 includes a side locking tab extending from the side of a respective wing 376. The distal locking tab may be flexible to provide a snap-lock fit with a corresponding structure 384 of an adjacent wing 376. For instance, a hole, aperture, channel, or other structure may be included on the adjacent wing 376 to receive the end of the locking tab. The opening and locking tab may be structured such that as the adjacent wings 376 tend to pull away from each other, the engagement of locking tab 382 with structure 384 can counteract the biasing or other force that would tend to cause body 372 to revert to its unstressed position. Typically, the locking tabs may be placed in corresponding structures 384 after a vessel has been inserted through lumen 374, and after tissue engaging structures 378 have been placed in a depressed state so as to engage and potentially expand or stretch a free end of the vessel. In other embodiments, the locking mechanisms may be positioned before depressing tissue engaging structures 378 and/or before passing a vessel through lumen 374.

The illustrated locking tabs are merely one example of a suitable mechanism for causing body 372 to remain in a stressed state or in an installation state. In other embodiments, for instance, a ring clamp may be placed around body 372 to counteract a biasing force that could revert body 372 back to an unstressed state. Still other mechanisms may include snap fits at the exterior faces of the wings, plastic deformation of wings 376 and/or corresponding tethers, or other mechanisms, or any combination thereof.

The foregoing detailed description makes reference to specific exemplary embodiments. However, it will be appreciated that various modifications and changes can be made without departing from the scope contemplated herein and as set forth in the appended claims. For example, various coupling devices and components may have different combinations of sizes, shapes, configurations, features, and the like. Such differences described herein are provided primarily to illustrate that there exist a number of different manners in which coupling devices may be used, made, and modified within the scope of this disclosure. Different features have also been combined in some embodiments to reduce the illustrations required, and are not intended to indicate that certain features are only compatible with other features. Thus, unless a feature is expressly indicated to be used only in connection with one or more other features, such features can be used interchangeably on any embodiment disclosed herein or modified in accordance with the scope of the present disclosure. The detailed description and accompanying drawings are thus to be regarded as merely illustrative, rather than as restrictive, and all such modifications or changes, if any, are intended to fall within the scope of this disclosure.

More specifically, while illustrative exemplary embodiments in this disclosure have been more particularly described, the present disclosure is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based on the language employed in the claims and not limited to examples described in the foregoing detailed description, which examples are to be construed as non-exclusive. Moreover, any steps recited in any method or process claims may be executed in any order and are not limited to the order presented in the claims, unless otherwise stated in the claims. Accordingly, the scope of the invention should be determined solely by the appended claims and their legal equivalents, rather than by the descriptions and examples given above.

What is claimed is:

1. A vascular coupling device, comprising:
a body defining an interior lumen in both a pre-installation configuration and an installation configuration, the interior lumen having a central axis;
a plurality of tissue engaging structures disposed at one end of said body and in the pre-installation configuration in which said plurality of tissue engaging structures extend away from said body at a non-parallel angle relative to said central axis; and
a plurality of receiving structures disposed at said one end of said body and in an alternating pattern relative to said plurality of tissue engaging structures,
wherein said plurality of tissue engaging structures are plastically deformable to the installation configuration in which said plurality of tissue engaging structures extend away from said body in a manner that is substantially parallel to said central axis.

2. The vascular coupling device recited in claim 1, wherein the plurality of tissue engaging structures each include at least two portions.

3. The vascular coupling device recited in claim 2, wherein at least two portions of a tissue engaging structure include an interior portion within said body and which extends into said body in a manner substantially parallel to said central axis, and an exterior portion extending in said pre-installation configuration.

4. The vascular coupling device recited in claim 2, wherein said plurality of tissue engaging structures includes at least five tissue engaging structures and said plurality of receiving structures includes at least five receiving structures.

5. The vascular coupling device recited in claim 1, wherein said body is formed of a flexible material.

6. A vascular coupling device, comprising:
a body, wherein said body is substantially defined by a plurality of wing elements, said plurality of wing elements being movable from a pre-installation configuration towards an installation configuration; and
a plurality of tissue engaging structures independently movably disposed relative to said plurality of wing elements, wherein said body and said plurality of wing elements are in an unstressed state and the plurality of tissue engaging structures are retracted;
a first state in which the plurality of wing elements are in an unstressed state and the plurality of tissue engaging structures are retracted;
a second state in which the plurality of wing elements are in an unstressed state and the plurality of tissue engaging structures are depressed, and in which the plurality of tissue engaging structures have interior tips separated by a first distance;
a third state in which the plurality of wing elements are in a stressed state, and the plurality of tissue engaging structures are depressed, and in which said plurality of tissue engaging structures have said interior tips separated by a second distance, said second distance being greater larger than said first distance.

7. The vascular coupling device recited in claim 6, wherein said plurality of tissue engaging structures are slideably disposed relative to said plurality of wing elements.

8. The vascular coupling device recited in claim 7, wherein said plurality of wings define a plurality of corresponding apertures therein, and wherein said plurality of tissue engaging structures are selectively moveable within said plurality of apertures.

9. The vascular coupling device recited in claim 6, wherein each of said plurality of tissue engaging structures are oriented to be substantially parallel to a corresponding one of said plurality of wing elements.

10. The vascular coupling device recited in claim 6, wherein said body defines a plurality of receiving portions.

11. The vascular coupling device recited in claim 6, wherein in said pre-installation configuration, said body is substantially disk-shaped.

12. The vascular coupling device recited in claim 6, wherein in said installation configuration, said body has an elongated shape.

13. The vascular coupling device recited in claim 6, wherein in said pre-installation configuration, said plurality of tissue engaging structures are radially moveable relative to a central axis of said body.

14. The vascular coupling device recited in claim 6, wherein in said installation configuration, said plurality of tissue engaging structures are moveable longitudinally relative to a central axis of said body.

15. The vascular coupling device recited in claim 6, wherein in said pre-installation configuration, said plurality wing elements each have an interior face having a thickness dimension, said thickness dimension being about parallel to a central axis of said body.

16. The vascular coupling device recited in claim 6, wherein in said installation configuration, said plurality of wing elements have an interior face having a thickness dimension, said thickness dimension being about perpendicular to a central axis of said body.

17. The vascular coupling device recited in claim 6, wherein said body further comprises a set of tethers disposed between the plurality of wing elements.

18. The vascular coupling device recited in claim 17, wherein said set of tethers extend along a partial length of said plurality of wing elements.

19. The vascular coupling device recited in claim 17, wherein said set of tethers are flexible to facilitate movement of said plurality of wings between pre-installation and installation configurations.

20. The vascular coupling device recited in claim 17, wherein said set of tethers define receiving portions configured to receive corresponding tissue engaging structures of a mating vascular coupling device.

21. The vascular coupling device recited in claim 20, wherein said receiving members define openings.

22. The vascular coupling device recited in claim 21, wherein said openings defined by said receiving members are at least partially open to a lumen of said body.

23. The vascular coupling device recited in claim 6, wherein said body is wholly, integrally formed.

24. The vascular coupling device recited in claim 6, wherein said body is formed as at least two portions thereafter joined together.

25. The vascular coupling device recited in claim 6, further comprising a locking mechanism configured to maintain said body in one or more of said pre-installation or said installation configuration.

26. The vascular coupling device recited in claim 6, wherein in said installation configuration, a gap is formed between adjacent wing elements, and along at least half a length of said plurality of wing elements.

27. The vascular coupling device recited in claim 6, wherein a lumen of said body has a length corresponding to a thickness of said plurality of wing elements when said body is in said pre-installation configuration, and corresponding to a length of said plurality of wing elements when said body is in said installation configuration.

\* \* \* \* \*